United States Patent
Jiang et al.

(10) Patent No.: US 10,031,138 B2
(45) Date of Patent: Jul. 24, 2018

(54) HIERARCHICAL FILMS HAVING ULTRA LOW FOULING AND HIGH RECOGNITION ELEMENT LOADING PROPERTIES

(71) Applicant: University of Washington through its Center for Commercialization, Seattle, WA (US)

(72) Inventors: Shaoyi Jiang, Redmond, WA (US); Norman David Brault, Jr., Seattle, WA (US); Harihara S. Sundaram, Seattle, WA (US); Chun-Jen Huang, Changhua (TW); Qiuming Yu, Redmond, WA (US); Yuting Li, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 290 days.

(21) Appl. No.: 13/747,290

(22) Filed: Jan. 22, 2013

(65) Prior Publication Data

US 2013/0244249 A1    Sep. 19, 2013

Related U.S. Application Data

(60) Provisional application No. 61/588,785, filed on Jan. 20, 2012.

(51) Int. Cl.
  *G01N 33/543* (2006.01)
  *G01N 21/552* (2014.01)

(52) U.S. Cl.
  CPC ..... *G01N 33/54393* (2013.01); *G01N 21/553* (2013.01)

(58) Field of Classification Search
  CPC ................ G01N 21/553; G01N 33/54393
  See application file for complete search history.

(56) References Cited

U.S. PATENT DOCUMENTS

| | | |
|---|---|---|
| 3,671,502 A | 6/1972 | Samour |
| 4,075,183 A | 2/1978 | Kawakami |
| 4,138,446 A | 2/1979 | Kawakami |
| 4,415,388 A | 11/1983 | Korpman |
| 4,493,926 A | 1/1985 | Williams, Jr. |
| 4,921,915 A | 5/1990 | Dengler |
| 4,985,023 A | 1/1991 | Blank |
| 5,204,060 A | 4/1993 | Allenmark |
| 5,233,453 A | 8/1993 | Sivarajan et al. |
| 5,633,724 A | 5/1997 | King et al. |
| 5,638,396 A | 6/1997 | Klimek |
| 5,714,360 A | 2/1998 | Swan |
| 5,776,711 A | 7/1998 | Vyas et al. |
| 5,781,284 A | 7/1998 | Infante |
| 5,804,453 A | 9/1998 | Chen |
| 5,838,870 A | 11/1998 | Soref |
| 5,919,523 A | 7/1999 | Sundberg |
| 5,952,035 A | 9/1999 | Erb et al. |
| 5,986,042 A | 11/1999 | Irizato |
| 6,330,388 B1 | 12/2001 | Bendett et al. |
| 6,361,768 B1 | 3/2002 | Galleguillos |
| 6,370,406 B1 | 4/2002 | Wach et al. |
| 6,486,333 B1 | 11/2002 | Murayama |
| 6,488,896 B2 | 12/2002 | Weigl et al. |
| 6,558,626 B1 | 5/2003 | Aker et al. |
| 6,570,893 B1 | 5/2003 | Libatique et al. |
| 6,661,950 B1 | 12/2003 | Strecker |
| 6,781,696 B1 | 8/2004 | Rosenberger et al. |
| 6,782,205 B2 | 8/2004 | Trisnadi et al. |
| 6,831,938 B1 | 12/2004 | Gunn, III |
| 6,834,152 B2 | 12/2004 | Gunn, III et al. |
| 6,839,488 B2 | 1/2005 | Gunn, III |
| 6,853,756 B2 | 2/2005 | Gerlach et al. |
| 6,888,973 B2 | 5/2005 | Kolodziejski et al. |
| 6,897,263 B2 | 5/2005 | Hell |
| 6,917,727 B2 | 7/2005 | Gunn, III et al. |
| 6,920,272 B2 | 7/2005 | Wang |
| 7,008,559 B2 | 3/2006 | Chen |
| 7,027,476 B2 | 4/2006 | Taghavi-Larigani et al. |
| 7,056,532 B1 | 6/2006 | Kabanov |
| 7,067,072 B2 | 6/2006 | Chen |
| 7,067,342 B2 | 6/2006 | Zia et al. |
| 7,075,954 B2 | 7/2006 | Ledentsov et al. |
| 7,082,235 B2 | 7/2006 | Gunn, III |
| 7,095,010 B2 | 8/2006 | Scherer et al. |
| 7,120,338 B2 | 10/2006 | Gunn, III |

(Continued)

FOREIGN PATENT DOCUMENTS

DE     10 2006 004 111 A1     8/2007
EP          0 354 984 A2      2/1990

(Continued)

OTHER PUBLICATIONS

Kastantin et al., "Helix Formation in the Polymer Brush," Macromolecules, 2011, vol. 44, No. 12, pp. 4977-4987; Publication Date (Web): Jun. 2, 2011.*
Tao Wu, "Formation and properties of surface-anchored polymer assemblies with tunable physico-chemical characteristics," Dissertation, Raleigh, 2003, published on Internet on Mar. 15, 2003.*
Zhang et al., "Multilayered Gold-Nanoparticle/Polyimide Composite Thin Film through Layer-by-Layer Assembly," Langmuir, 2007, vol. 23, No. 20, pp. 10102-10108.*
Vaisocherová et al., "Ultralow Fouling and Functionalizable Surface Chemistry Based on a Zwitterionic Polymer Enabling Sensitive and Specific Protein Detection in Undiluted Blood Plasma," Anal. Chem., 2008, vol. 80, No. 20, pp. 7894-7901; Publication Date (Web): Sep. 23, 2008.*
Cruse et al., Atlas of Immunology, Third Edition, 2010, p. 835.*
Kaur et al., "Characterizing monoclonal antibody structure by carboxyl group footprinting," mABS, 2015, vol. 7, No. 3, pp. 540-552.*

(Continued)

*Primary Examiner* — Galina Yakovleva
(74) *Attorney, Agent, or Firm* — Christensen O'Connor Johnson Kindness PLLC

(57) ABSTRACT

Hierarchical films with structurally regulated functionalities through the integration of two-dimensional and three-dimensional structures to achieve ultra low nonspecific binding and high loading of molecular recognition elements, and methods for making and using the films.

17 Claims, 15 Drawing Sheets

(56) References Cited

U.S. PATENT DOCUMENTS

| | | |
|---|---|---|
| 7,126,136 B2 | 10/2006 | Chen |
| 7,127,147 B2 | 10/2006 | Gunn, III et al. |
| 7,139,459 B2 | 11/2006 | Kochergin et al. |
| 7,145,165 B2 | 12/2006 | Cox et al. |
| 7,164,821 B2 | 1/2007 | Gunn, III |
| 7,167,606 B2 | 1/2007 | Gunn, III et al. |
| 7,167,615 B1 | 1/2007 | Wawro et al. |
| 7,177,492 B2 | 2/2007 | Strecker |
| 7,212,701 B2 | 5/2007 | Strecker |
| 7,228,016 B2 | 6/2007 | Beausoleil |
| 7,244,926 B2 | 7/2007 | Ja et al. |
| 7,266,271 B2 | 9/2007 | Strecker et al. |
| 7,291,427 B2 | 11/2007 | Kawamura |
| 7,306,625 B1 | 12/2007 | Stratford |
| 7,307,719 B2 | 12/2007 | Wang et al. |
| 7,309,628 B2 | 12/2007 | Zia et al. |
| 7,315,679 B2 | 1/2008 | Hochberg et al. |
| 7,324,199 B2 | 1/2008 | Ja et al. |
| 7,335,248 B2 | 2/2008 | Abou-Nemeh |
| 7,336,859 B2 | 2/2008 | Sanders |
| 7,361,501 B2 | 4/2008 | Koo et al. |
| 7,368,281 B2 | 5/2008 | Mozdy et al. |
| 7,397,043 B2 | 7/2008 | Ja |
| 7,400,399 B2 | 7/2008 | Wawro et al. |
| 7,419,636 B2 | 9/2008 | Aker et al. |
| 7,419,638 B2 | 9/2008 | Saltsman et al. |
| 7,435,944 B2 | 10/2008 | Ja et al. |
| 7,462,325 B2 | 12/2008 | Hancock et al. |
| 7,488,930 B2 | 2/2009 | Ajgaonkar et al. |
| 7,497,992 B2 | 3/2009 | Cunningham et al. |
| 7,501,092 B2 | 3/2009 | Chen |
| 7,508,849 B2 | 3/2009 | Tanaka et al. |
| 7,519,257 B2 | 4/2009 | Lipson et al. |
| 7,528,403 B1 | 5/2009 | Borselli et al. |
| 7,538,329 B2 | 5/2009 | Chen et al. |
| 7,539,369 B2 | 5/2009 | Yamazaki |
| 7,616,850 B1 | 11/2009 | Watts et al. |
| 7,634,165 B2 | 12/2009 | Wang |
| 7,639,723 B2 | 12/2009 | Yamazaki |
| 7,643,710 B1 | 1/2010 | Liu |
| 7,648,835 B2 | 1/2010 | Breidford et al. |
| 7,664,157 B2 | 2/2010 | Yamazaki |
| 7,693,369 B2 | 4/2010 | Fan et al. |
| 7,713,689 B2 | 5/2010 | Chilkoti |
| 7,737,224 B2 | 6/2010 | Willis |
| 7,738,527 B2 | 6/2010 | He |
| 7,763,453 B2 | 7/2010 | Clemmens et al. |
| 7,773,642 B2 | 8/2010 | Yamazaki |
| 7,778,499 B2 | 8/2010 | Janz et al. |
| 7,783,144 B2 | 8/2010 | Chigrinov et al. |
| RE41,643 E | 9/2010 | Boutos |
| 7,796,262 B1 | 9/2010 | Wang et al. |
| 7,799,573 B2 | 9/2010 | Deans et al. |
| 7,815,922 B2 | 10/2010 | Chaney |
| 7,825,380 B2 | 11/2010 | Puscasu et al. |
| 7,826,688 B1 | 11/2010 | Sadagopan et al. |
| 7,831,123 B2 | 11/2010 | Sparacin et al. |
| 7,831,298 B1 | 11/2010 | Wang et al. |
| 7,835,006 B2 | 11/2010 | Ja |
| 7,853,108 B2 | 12/2010 | Popovic et al. |
| 7,879,444 B2 | 2/2011 | Jiang |
| 7,903,909 B2 | 3/2011 | Popovic |
| 7,936,463 B2 | 5/2011 | Kiesel et al. |
| 7,955,836 B2 | 6/2011 | Clemmens et al. |
| 7,961,988 B2 | 6/2011 | Krug et al. |
| 7,968,848 B2 | 6/2011 | Johnson et al. |
| 7,970,244 B2 | 6/2011 | Krug et al. |
| 7,973,696 B2 | 7/2011 | Puscasu et al. |
| 7,982,878 B1 | 7/2011 | Ja |
| 7,983,517 B1 | 7/2011 | Watts et al. |
| 7,999,938 B2 | 8/2011 | Wang |
| 8,000,565 B2 | 8/2011 | Liu |
| 8,019,185 B2 | 9/2011 | Yap |
| 8,045,834 B2 | 10/2011 | Painter et al. |
| 8,064,490 B2 | 11/2011 | Okayama |
| 8,068,706 B2 | 11/2011 | Popovic et al. |
| 8,076,090 B2 | 12/2011 | Fang et al. |
| 8,094,987 B2 | 1/2012 | Martin Armani |
| 8,111,401 B2 | 2/2012 | Magnusson et al. |
| 8,111,402 B2 | 2/2012 | Le et al. |
| 8,116,603 B2 | 2/2012 | Popovic |
| 8,120,782 B2 | 2/2012 | Kiesel et al. |
| 8,139,904 B2 | 3/2012 | Green et al. |
| 8,195,011 B2 | 6/2012 | Goldring et al. |
| 8,195,014 B2 | 6/2012 | Heideman et al. |
| 8,213,751 B1 | 7/2012 | Ho et al. |
| 8,244,077 B1 | 8/2012 | Yap |
| 8,263,986 B2 | 9/2012 | Hajj-Hassan et al. |
| 8,270,789 B2 | 9/2012 | Ogawa et al. |
| 8,270,790 B2 | 9/2012 | Ogawa et al. |
| 8,288,157 B2 | 10/2012 | Duer |
| 8,295,315 B2 | 10/2012 | Ward et al. |
| 8,307,724 B1 | 11/2012 | Wichert et al. |
| 8,447,145 B2 | 5/2013 | Goldring et al. |
| 8,467,858 B2 | 6/2013 | Vertikov et al. |
| 8,493,560 B2 | 7/2013 | Shopova et al. |
| 8,544,506 B2 | 10/2013 | Auriol |
| 8,617,592 B2 | 12/2013 | Jiang et al. |
| 8,835,144 B2 | 9/2014 | Jiang |
| 2002/0127236 A1 | 9/2002 | Rodkey et al. |
| 2002/0128234 A1* | 9/2002 | Hubbell et al. ............... 514/100 |
| 2003/0059853 A1 | 3/2003 | Lockhart |
| 2003/0143580 A1 | 7/2003 | Straus |
| 2004/0063587 A1 | 4/2004 | Horton et al. |
| 2004/0063881 A1 | 4/2004 | Lewis |
| 2004/0067503 A1 | 4/2004 | Tan et al. |
| 2004/0086543 A1 | 5/2004 | Keogh et al. |
| 2004/0121337 A1 | 6/2004 | Deans et al. |
| 2005/0054908 A1 | 3/2005 | Blank et al. |
| 2005/0058689 A1 | 3/2005 | McDaniel |
| 2005/0208428 A1 | 9/2005 | Kawamura et al. |
| 2005/0220880 A1 | 10/2005 | Lewis et al. |
| 2006/0116562 A1 | 6/2006 | Acosta et al. |
| 2006/0140240 A1 | 6/2006 | Chen |
| 2006/0183863 A1 | 8/2006 | Huang |
| 2006/0193550 A1 | 8/2006 | Wawro et al. |
| 2006/0194008 A1 | 8/2006 | Schwartz et al. |
| 2006/0196253 A1 | 9/2006 | Crawley et al. |
| 2006/0240072 A1 | 10/2006 | Chudzik |
| 2006/0255292 A1 | 11/2006 | Ja |
| 2006/0270064 A1 | 11/2006 | Gordon et al. |
| 2007/0036479 A1 | 2/2007 | Beausoleil |
| 2007/0042198 A1 | 2/2007 | Schonemyr |
| 2007/0104654 A1 | 5/2007 | Hsieh |
| 2007/0111321 A1 | 5/2007 | Deans et al. |
| 2007/0133001 A1 | 6/2007 | Cox et al. |
| 2007/0224652 A1 | 9/2007 | Holgersson et al. |
| 2008/0130393 A1 | 6/2008 | Yeung |
| 2008/0131939 A1 | 6/2008 | Roper |
| 2008/0160600 A1 | 7/2008 | Zuccato et al. |
| 2008/0181861 A1 | 7/2008 | Jiang |
| 2008/0193076 A1 | 8/2008 | Witzens et al. |
| 2008/0248578 A1 | 10/2008 | Deans et al. |
| 2008/0299177 A1 | 12/2008 | Hardy |
| 2008/0316485 A1 | 12/2008 | Wawro et al. |
| 2009/0017455 A1 | 1/2009 | Kwong et al. |
| 2009/0068668 A1 | 3/2009 | Duer |
| 2009/0068726 A1 | 3/2009 | Magnin et al. |
| 2009/0156460 A1 | 6/2009 | Jiang et al. |
| 2009/0197791 A1 | 8/2009 | Balastre |
| 2009/0259015 A1 | 10/2009 | Jiang |
| 2009/0325211 A1 | 12/2009 | Fang et al. |
| 2010/0099160 A1 | 4/2010 | Jiang |
| 2010/0247614 A1 | 9/2010 | Jiang et al. |
| 2010/0248391 A1 | 9/2010 | Garcia Tello |
| 2010/0249267 A1 | 9/2010 | Jiang et al. |
| 2011/0039717 A1 | 2/2011 | Kwong et al. |
| 2011/0039730 A1 | 2/2011 | Erickson et al. |
| 2011/0045472 A1 | 2/2011 | Gunn, III |
| 2011/0097277 A1 | 4/2011 | Jiang et al. |
| 2011/0105712 A1 | 5/2011 | Jiang et al. |
| 2011/0116093 A1 | 5/2011 | Liu et al. |
| 2011/0129846 A1 | 6/2011 | Huh et al. |
| 2011/0133063 A1 | 6/2011 | Ji et al. |

(56) References Cited

U.S. PATENT DOCUMENTS

| | | |
|---|---|---|
| 2011/0142396 A1 | 6/2011 | Okamoto |
| 2011/0158582 A1 | 6/2011 | Su et al. |
| 2011/0195104 A1 | 8/2011 | Jiang et al. |
| 2011/0282005 A1 | 11/2011 | Jiang et al. |
| 2012/0069331 A1 | 3/2012 | Shopova et al. |
| 2012/0092650 A1 | 4/2012 | Gunn, III et al. |
| 2012/0107946 A1 | 5/2012 | Deans et al. |
| 2012/0195332 A1 | 8/2012 | Yoffe et al. |
| 2012/0225474 A1 | 9/2012 | Wagner et al. |
| 2012/0225475 A1 | 9/2012 | Wagner et al. |
| 2012/0258549 A1 | 10/2012 | Lu et al. |
| 2012/0276549 A1 | 11/2012 | Cunningham et al. |
| 2013/0071061 A1 | 3/2013 | Tu et al. |
| 2013/0083815 A1 | 4/2013 | Fang et al. |
| 2013/0109941 A1 | 5/2013 | Li et al. |
| 2013/0144148 A1 | 6/2013 | Li et al. |
| 2013/0244249 A1 | 9/2013 | Jiang et al. |
| 2013/0288387 A1 | 10/2013 | Blancher et al. |
| 2014/0135760 A1 | 5/2014 | Cadouri et al. |
| 2014/0221577 A1 | 8/2014 | Jiang et al. |
| 2014/0315760 A1* | 10/2014 | Ratner et al. .......... 506/18 |
| 2014/0370567 A1 | 12/2014 | Jiang |

FOREIGN PATENT DOCUMENTS

| | | |
|---|---|---|
| EP | 0 419 654 A1 | 4/1991 |
| EP | 0 479 245 A2 | 4/1992 |
| EP | 1263533 B1 | 3/2010 |
| EP | 1773481 B1 | 8/2010 |
| EP | 2229583 A2 | 9/2010 |
| EP | 2347247 A2 | 7/2011 |
| EP | 2 496 614 A2 | 9/2012 |
| JP | 63-39909 A | 2/1988 |
| JP | 63-234007 A | 9/1988 |
| JP | 3-110473 A | 5/1991 |
| JP | 10-132732 A | 5/1998 |
| JP | 2004-510851 A | 4/2004 |
| JP | 2005-521052 A | 7/2005 |
| JP | 2007-130194 A | 5/2007 |
| JP | 2010-530955 A | 9/2010 |
| JP | 4733331 B2 | 7/2011 |
| JP | 4758891 B2 | 2/2012 |
| JP | 4885852 B2 | 2/2012 |
| JP | 2013-510229 A | 3/2013 |
| SU | 1780673 A1 | 12/1992 |
| WO | 98/16831 A1 | 4/1998 |
| WO | 00/39176 A1 | 7/2000 |
| WO | 02/28929 A1 | 4/2002 |
| WO | 2003/023474 A1 | 3/2003 |
| WO | 2003/023824 A2 | 3/2003 |
| WO | 03/036290 A1 | 5/2003 |
| WO | 2003/081230 A1 | 10/2003 |
| WO | 2004/058837 A2 | 7/2004 |
| WO | 2004/100666 A1 | 11/2004 |
| WO | 2007/024393 A2 | 3/2007 |
| WO | 2007/024933 A2 | 3/2007 |
| WO | 2007/068744 A1 | 6/2007 |
| WO | 2007/099239 A2 | 9/2007 |
| WO | 2007/127512 A2 | 11/2007 |
| WO | 2008/019381 A1 | 2/2008 |
| WO | 2008/061223 A3 | 5/2008 |
| WO | 2008/083390 A2 | 7/2008 |
| WO | 2008/122793 A2 | 10/2008 |
| WO | 2009/014553 A1 | 1/2009 |
| WO | 2009/025680 A1 | 2/2009 |
| WO | 2009/067562 A1 | 5/2009 |
| WO | 2009/067565 A2 | 5/2009 |
| WO | 2009/067566 A1 | 5/2009 |
| WO | 2009/076323 A3 | 6/2009 |
| WO | 2009/099126 A1 | 8/2009 |
| WO | 2009/136869 A1 | 11/2009 |
| WO | 2010/030251 A2 | 3/2010 |
| WO | 2010/033435 A2 | 3/2010 |
| WO | 2010/062627 A2 | 6/2010 |
| WO | 2010/120293 A1 | 10/2010 |
| WO | 2011/057219 A2 | 5/2011 |
| WO | 2011/057224 A2 | 5/2011 |
| WO | 2011/057225 A2 | 5/2011 |
| WO | 2011/088247 A1 | 7/2011 |
| WO | 2011/133670 A2 | 10/2011 |
| WO | 2011/152747 A1 | 12/2011 |
| WO | 2012/061778 A2 | 5/2012 |
| WO | 2012/149497 A2 | 11/2012 |

OTHER PUBLICATIONS

Brault et al., "Dry Film Refractive Index as an Important Parameter for Ultra-Low Fouling Surface Coatings," Biomacromolecules, 2012, vol. 13, No. 3, pp. 589-593; Publication Date (Web): Feb. 21, 2012.*

Berge, S.M., et al., "Pharmaceutical Salts," Journal of Pharmaceutical Sciences 66(1):1-19, Jan. 1977.

Chang, Y., et al., "Highly Protein-Resistant Coatings From Well-Defined Diblock Copolymers Containing Sulfobetaines," Langmuir 22(5):2222-2226, Feb. 2006.

Chen, S., et al., "Controlling Antibody Orientation on Charged Self-Assembled Monolayers," Langmuir 19(7):2859-2864, Apr. 2003.

Chen, S., et al., "Strong Resistance of Oligo(phosphorylcholine) Self-Assembled Monolayers to Protein Adsorption," Langmuir 22(6):2418-2421, Mar. 2006.

Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.

Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.

Feng, W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Lowe, A.B., et al., "Well-Defined Sulfobetaine-Based Statistical Copolymers as Potential Antibioadherent Coatings," Journal of Biomedical Materials Research 52(1):88-94, Jul. 2000.

West, S.L., et al., "The Biocompatibility of Crosslinkable Copolymer Coatings Containing Sulfobetaines and Phosphobetaines," Biomaterials 25:1195-1204, Apr. 2004.

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53 (1):121-126, Jan. 2004.

(56) References Cited

OTHER PUBLICATIONS

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.
Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.
Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.
Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.
Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.
Zhang, Z., et al., "Superflow Fouling Sulfobetaine and Carboxybetaine Polymers on Glass Slides," Langmuir 22(24):10072-10077, Nov. 2006.
Zhang, Z., "Surface Grafted Sulfobetaine Polymers Via Atom Transfer Radical Polymerization as Superlow Fouling Coatings," Journal of Physical Chemistry B 110(22):10799-10804, Jun. 2006.
Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.
Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.
Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.
"Betaine," Wikipedia, The Free Encyclopedia, <http://en.wikipedia.org/wiki/Betaine> [retrieved Jul. 31, 2011], 1 page.
"Bromide," Wikipedia, The Free Encyclopedia, <http://en.wikipedia.org/wiki/Bromide> [retrieved Jul. 27, 2011], 3 pages.
International Preliminary Report on Patentability dated May 8, 2012, issued in related International Application No. PCT/US2010/055887, filed Nov. 8, 2010, 8 pages.
International Search Report and Written Opinion dated Jul. 28, 2011, issued in related International Application No. PCT/US2010/055887, filed Nov. 8, 2010, 12 pages.
"Nail Infections," Health911, <http://www.health911.com/nail-infections> [retrieved Aug. 29, 2011], 3 pages.
Anderson, J.M., "Inflammation, Wound Healing, and the Foreign-Body Response," in B.D. Ratner et al. (eds.), "Biomaterials Science," 2nd ed., Elsevier Academic Press, Amsterdam, Chap. 4.2, pp. 296-304, 2004.
Aspnes, D.E., "Optical Properties of Thin Films," Thin Solid Films 89(3):249-262, Mar. 1982.
Azzaroni, O., et al., "UCST Wetting Transitions of Polyzwitterionic Brushes Driven by Self-Association," Angewandte Chemie International Edition 45(11):1770-1774, Mar. 2006.
Brault, N.D., et al., "Ultra-Low Fouling and Functionalizable Zwitterionic Coatings Grafted Onto $SiO_2$ via a Biomimetic Adhesive Group for Sensing and Detection in Complex Media," Biosensors and Bioelectronics 25(10):2276-2282, Jun. 2010.
Braunecker, W.A., and K. Matyjaszewski, "Controlled/Living Radical Polymerization: Features, Developments, and Perspectives," Progress in Polymer Science 32(1):93-146, Jan. 2007.
Callow, J.A., and M.E. Callow, "Trends in the Development of Environmentally Friendly Fouling-Resistant Marine Coatings," Nature: Communications 2:244, Mar. 2011, 10 pages.
Calvo, K.R., et al., "Clinical Proteomics: From Biomarker Discovery and Cell Signaling Profiles to Individualized Personal Therapy," Bioscience Reports 25(1-2):107-125, Feb.-Apr. 2005.
Cheng, N., et al., "The Effect of [Cu(I)]/[Cu(II)] Ratio on the Kinetics and Conformation of Polyelectrolyte Brushes by Atom Transfer Radical Polymerization," Macromolecular Rapid Communications 27(19):1632-1636, Oct. 2006.
De Boer, B., et al., "'Living' Free Radical Photopolymerization Initiated From Surface-Grafted Iniferter Monolayers," Macromolecules 33(2):349-356, Jan. 2000.
Deng, J., et al., "Developments and New Applications of UV-Induced Surface Graft Polymerizations," Progress in Polymer Science 34(2):156-193, Feb. 2009.
Dostálek, J., et al., "Surface Plasmon Resonance Biosensor Based on Integrated Optical Waveguide," Sensors and Actuators B 76(1-3):8-12, Jun. 2001.
Edmondson, S., et al., "Surface Polymerization From Planar Surfaces by Atom Transfer Radical Polymerization Using Polyelectrolytic Macroinitiators," Macromolecules 40(15):5271-5278, Jul. 2007.
Eisenstein, M., "Protein Arrays: Growing Pains," Nature 444(7121):959-962, Dec. 2006.
Eskin, S.G., et al., "Some Background Concepts," in B.D. Ratner et al. (eds.), "Biomaterials Science," 2nd ed., Elsevier Academic Press, Amsterdam, 2004, Chap. 3, pp. 237-246.
Farokhzad, O.C., and R. Langer, "Impact of Nanotechnology on Drug Delivery," ACS Nano 3(1):16-20, Jan. 2009.
Figeys, D., "Adapting Arrays and Lab-on-a-Chip Technology for Proteomics," Proteomics 2(4):373-382, Apr. 2002.
Goda, T., et al., "Biomimetic Phosphorylcholine Polymer Grafting From Polydimethylsiloxane Surface Using Photo-Induced Polymerization," Biomaterials 27(30):5151-5160, Oct. 2006.
Harder, P., et al., "Molecular Conformation in Oligo(ethylene glycol)-Terminated Self-Assembled Monolayers on Gold and Silver Surfaces Determines Their Ability to Resist Protein Adsorption," Journal of Physical Chemistry B 102(2):426-436, Jan. 1998.
He, Y., et al., "Molecular Simulation Studies of Protein Interactions With Zwitterionic Phosphorylcholine Self-Assembled Monolayers in the Presence of Water," Langmuir 24(18):10358-10364, Sep. 2008.
Herold, D.A., et al., "Oxidation of Polyethylene Glycols by Alcohol Dehydrogenase," Biochemical Pharmacology 38(1):73-76, Jan. 1989.
Holmlin, R.E, et al., "Zwitterionic SAMs That Resist Nonspecific Adsorption of Protein From Aqueous Buffer," Langmuir 17(9):2841-2850, May 2001.
Homola, J., "Electromagnetic Theory of Surface Plasmons," in O.S. Wolfbeis (ed.), "Surface Plasmon Resonance Based Sensors," Springer-Verlag, Berlin, 2006, vol. 4, pp. 3-44.
Homola, J., "On the Sensitivity of Surface Plasmon Resonance Sensors With Spectral Interrogation," Sensors and Actuators B 41(1-3):207-211, Jun. 1997.
Homola, J., and M. Piliarik, "Surface Plasmon Resonance (SPR) Sensors," in O.S. Wolfbeis (ed.), "Surface Plasmon Resonance Based Sensors," Springer-Verlag, Berlin, 2006, vol. 4, pp. 45-67.
Homola, J., et al., "A Novel Multichannel Surface Plasmon Resonance Biosensor," Sensors and Actuators B 76(1-3):403-410, Jun. 2001.
Homola, J., et al., "Spectral Surface Plasmon Resonance Biosensor for Detection of Staphylococcal Enterotoxin B in Milk," International Journal of Food Microbiology 75(1-2):61-69, May 2002.
Hoyle, C.E., and C.N. Bowman, "Thiol—Ene Click Chemistry," Angewandte Chemie International Edition 49(9):1540-1573, Feb. 2010.
Huang, C.-J., et al., "Long-Range Surface Plasmon-Enhanced Fluorescence Spectroscopy Biosensor for Ultrasensitive Detection of *E coli* 0157:H7," Analytical Chemistry 83(3):674-677, Feb. 2011.
Huang, N.-P., et al., "Poly(L-lysine)-g-poly(ethylene glycol) Layers on Metal Oxide Surfaces: Surface-Analytical Characterization and Resistance to Serum and Fibrinogen Adsorption," Langmuir 17(2):489-498, Jan. 2001.
Huang, R.-P., "Protein Arrays, an Excellent Tool in Biomedical Research," Frontiers in Bioscience 8:d559-d576, May 2003.
Huang, W., et al., "Functionalization of Surfaces by Water-Accelerated Atom-Transfer Radical Polymerization of Hydroxyethyl Methacrylate and Subsequent Derivatization," Macromolecules 35(4):1175-1179, Feb. 2002.

(56) References Cited

OTHER PUBLICATIONS

Hucknall, A., et al., "In Pursuit of Zero: Polymer Brushes That Resist the Adsorption of Proteins," Advanced Materials 21(23):2441-2446, Jun. 2009.
Ishihara, K., et al., "Inhibition of Fibroblast Cell Adhesion on Substrate by Coating With 2-methacryloyloxyethyl Phosphorylcholine Polymers," Journal of Biomaterials Science: Polymer Edition 10(10):1047-1061, Oct. 1999.
Ishihara, K. et al., "Protein Adsorption From Human Plasma Is Reduced on Phospholipid Polymers," Journal of Biomedical Materials Research 25(11)1397-1407, Nov. 1991.
Jiang, S., et al., "Cationic Polycarboxybetaine Esters," U.S. Appl. No. 60/989,073, filed Nov. 19,2007.
Jiang, S., and Z.Cao, "Ultralow-Fouling, Functionalizable, and Hydrolyzable Zwitterionic Materials and Their Derivatives for Biological Applications," Advanced Materials 22(9):920-932, Mar. 2010.
Johnsson, B., et al., "Comparison of Methods for Immobilization to Carboxymethyl Dextran Sensor Surfaces by Analysis of the Specific Activity of Monoclonal Antibodies," Journal of Molecular Recognition 8(1-2):125-131, Jan.-Apr. 1995.
Johnsson, B., et al., "Immobilization of Proteins to a Carboxymethyldextran-Modified Gold Surface for Biospecific Interaction Analysis in Surface Plasmon Resonance Sensors," Analytical Biochemistry 198(2):268-277, Nov. 1991.
Jones, D.M., et al., "Surface-Initiated Polymerizations in Aqueous Media: Effect of Initiator Density," Langmuir 18(4):1265-1269, Feb. 2002.
Jogs, T.O., et al., "A Microarray Enzyme-Linked Immunosorbent Assay for Autoimmune Diagnostics," Electrophoresis 21(13):2641-2650, Jul. 2000.
Kim, B.-S., et al., "All-Star Polymer Multilayers as pH-Responsive Nanofilms," Macromolecules 42(1):368-375, Jan. 2009.
Kitano, H., et al., "Correlation Between the Structure of Water in the Vicinity of Carboxybetaine Polymers and Their Blood-Compatibility," Langmuir 21(25):11932-11940, Dec. 2005.
Kizhakkedathu, J.N., et al., "Poly(oligo(ethylene glycol)acrylamide) Brushes by Surface Initiated Polymerization: Effect of Macromonomer Chain Length on Brush Growth and Protein Adsorption From Blood Plasma," Langmuir 25(6):3794-3801, Mar. 2009.
Kolb, H.C., et al., "Click Chemistry: Diverse Chemical Function From a Few Good Reactions," Angewandte Chemie International Edition 40(11):2004-2021, Jun. 2001.
Krause, J.E., et al., "Photoiniferter-Mediated Polymerization of Zwitterionic Carboxybetaine Monomers for Low-Fouling and Functionalizable Surface Coatings," Macromolecules 44(23):9213-9220, Dec. 2011.
Ladd, J., et al., "Zwitterionic Polymers Exhibiting High Resistance to Nonspecific Protein Adsorption From Human Serum and Plasma," Biomacromolecules 9(5):1357-1361, May 2008.
Langer, R., "Drugs on Target," Science 293(5527):58-59, Jul. 2001.
Lee, B.S., et al., "Surface-Initiated, Atom Transfer Radical Polymerization of Oligo(ethylene glycol) Methyl Ether Methacrylate and Subsequent Click Chemistry for Bioconjugation," Biomacromolecules 8(2):744-749, Feb. 2007.
Lewis, A.L., "Phosphorylcholine-Based Polymers and Their Use in the Prevention of Biofouling," Colloids and Surfaces B: Biointerfaces 18(3-4):261-275, Oct. 2000.
Li, L., et al., "Protein Interactions With Oligo(ethylene glycol) (OEG) Self-Assembled Monolayers: OEG Stability, Surface Packing Density and Protein Adsorption," Journal of Biomaterials Science: Polymer Edition 18(11):1415-1427, 2007.
Liaw, D.-J., et al., "Synthesis and Characteristics of the Poly(carboxybetaine)s and the Corresponding Cationic Polymers," Journal of Polymer Science Part A: Polymer Chemistry 35(16):3527-3536, Nov. 1997.
Liedberg, B., and I. Lundström, "Principles of Biosensing With an Extended Coupling Matrix and Surface Plasmon Resonance," Sensors and Actuators B 11(1-3):63-72, Mar. 1993.
Liotta, L.A., et al., "Protein Microarrays: Meeting Analytical Challenges for Clinical Applications," Cancer Cell 3(4):317-325, Apr. 2003.
Löfås, S., et al., "Methods for Site Controlled Coupling to Carboxymethyldextran Surfaces in Surface Plasmon Resonance Sensors," Biosensors and Bioelectronics 10(9-10):813-822, 1995.
Löfås, S., and B. Johnsson, "A Novel Hydrogel Matrix on Gold Surfaces in Surface Plasmon Resonance Sensors for Fast and Efficient Covalent Immobilization of Ligands," Journal of the Chemical Society, Chemical Communications 21:1526-1528, 1990.
Lowe, A.B., and C.L. McCormick, "Synthesis and Solution Properties of Zwitterionic Polymers," Chemical Reviews 102(11):4177-4189, Nov. 2002.
Luo, N., et al., "A Methacrylated Photoiniferter as a Chemical Basis for Microlithography: Micropatterning Based on Photografting Polymerization," Macromolecules 36(18):6739-6745, Sep. 2003.
Ma, H., et al., "'Non-Fouling' Oligo(ethylene glycol)-Functionalized Polymer Brushes Synthesized by Surface-Initiated Atom Transfer Radical Polymerization," Advanced Materials 16(4):338-341, Feb. 2004.
Malmqvist, M., "Biospecific Interaction Analysis Using Biosensor Technology," Nature 361(6408):186-187, Jan. 1993.
Masson, J.-F., et al., "Biocompatible Polymers for Antibody Support on Gold Surfaces," Talanta 67(5):918-925, Oct. 2005.
Masson, J.-F., et al., "Preparation of Analyte-Sensitive Polymeric Supports for Biochemical Sensors," Talanta 64(3):716-725, Oct. 2004.
Matsuda, T., "Photoiniferter-Driven Precision Surface Graft Microarchitectures for Biomedical Applications," in R. Jordan (ed.), "Surface-Initiated Polymerization," Springer, Berlin, 2006, vol. 197, pp. 67-106.
Matyjaszewski, K., and N.V. Tsarevsky, "Nanostructured Functional Materials Prepared by Atom Transfer Radical Polymerization," Nature: Chemistry 1(4):276-288, Jul. 2009.
Matyjaszewski, K, et al., "Polymers at Interfaces: Using Atom Transfer Radical Polymerization in the Controlled Growth of Homopolymers and Block Copolymers From Silicon Surfaces in the Absence of Untethered Sacrificial Initiator," Macromolecules 32(26):8716-8724, Dec. 1999.
Mendelsohn, J.D., et al., "Fabrication of Microporous Thin Films From Polyelectrolyte Multilayers," Langmuir 16(11):5017-5023, May 2000.
Ostuni, E., et al., "Self-Assembled Monolayers That Resist the Adsorption of Proteins and the Adhesion of Bacterial and Mammalian Cells," Langmuir 17(20):6336-6343, Oct. 2001.
Ostuni, E., et al., "A Survey of Structure-Property Relationships of Surfaces That Resist the Adsorption of Protein," Langmuir 17(18):5605-5620, Sep. 2001.
Otsu, T., "Iniferter Concept and Living Radical Polymerization," Journal of Polymer Science Part A: Polymer Chemistry 38(12):2121-2136, Jun. 2000.
Otsu, T., and M. Yoshida, "Role of Initiator-Transfer Agent-Terminator (Iniferter) in Radical Polymerizations: Polymer Design by Organic Disulfides as Iniferters," Die Makromolekulare Chemie, Rapid Communications 3(2)127-132, Feb. 1982.
Otsuka, et al., "PEGylated Nanoparticles for Biological and Pharmaceutical Applications," Advanced Drug Delivery Reviews 55(3):403-419, Feb. 2003.
Prime, K.L., and G.M. Whitesides, "Self-Assembled Organic Monolayers: Model Systems for Studying Adsorption of Proteins at Surfaces," Science 252(5009):1164-1167, May 1991.
Pyun, J., et al., "Synthesis of Polymer Brushes Using Atom Transfer Radical Polymerization," Macromolecular Rapid Communations 24(18):1043-1059, Dec. 2003.
Rahane, S.B., et al., "Impact of Added Tetraethylthiuram Disulfide Deactivator on the Kinetics of Growth and Reinitiation of Poly(methyl methacrylate) Brushes Made by Surface-Initiated Photoiniferter-Mediated Photopolymerization," Macromolecules 39(26):8987-8991, Dec. 2006.
Rahane, S.B., et al., "Kinetic Modeling of Surface-Initiated Photoiniferter-Mediated Photopolymerization in Presence of Tetraethylthiuram Disulfide," Macromolecules 41(24):9612-9618, Dec. 2008.

(56) References Cited

OTHER PUBLICATIONS

Rahane, S.B., et al., "Kinetics of Surface-Initiated Photoiniferter-Mediated Photopolymerization," Macromolecules 38(20):8202-8210, Oct. 2005.
Ratner, B.D., and S.J. Bryant, "Biomaterials: Where We Have Been and Where We Are Going," Annual Review of Biomedical Engineering 6:41-75, Aug. 2004.
Rodriguez-Emmenegger, C., et al., "Polymer Brushes Showing Non-Fouling in Blood Plasma Challenge the Currently Accepted Design of Protein Resistant Surfaces," Macromolecular Rapid Communications 32(13):952-957, Jul. 2011.
Schoen, F.J., and A.S. Hoffman, "Implant and Device Failure," in B.D. Ratner et al. (eds.), "Biomaterials Science," 2nd ed., Elsevier Academic Press, Amsterdam, 2004, Chap. 9.3, pp. 760-765.
Shapiro, M.G., et al., "Directed Evolution of a Magnetic Resonance Imaging Contrast Agent for Noninvasive Imaging of Dopamine," Nature: Biotechnology 28(3):264-270, Mar. 2010.
Singh, N., et al., "The Role of Independently Variable Grafting Density and Layer Thickness of Polymer Nanolayers on Peptide Adsorption and Cell Adhesion," Biomaterials 28(5):763-761, Feb. 2007.
Spisak, S., et al., "Protein Microchips in Biomedicine and Biomarker Discovery," Electrophoresis 28(23):4261-4273, Dec. 2007.
Toomey, R., and M. Tirrell, "Functional Polymer Brushes in Aqueous Media From Self-Assembled and Surface-Initiated Polymers," Annual Review of Physical Chemistry 59:493-517, May 2008.
Tsai, W.-B., et al., "Human Plasma Fibrinogen Adsorption and Platelet Adhesion to Polystyrene," Journal of Biomedical Materials Research 44(2):130-139, Feb. 1999.
Turgman-Cohen, S., and J. Genzer, "Computer Simulation of Controlled Radical Polymerization: Effect of Chain Confinement Due to Initiator Grafting Density and Solvent Quality in 'Grafting From' Method," Macromolecules 43(22):9567-9577, Nov. 2010.
Vaisocherová, H., et al., "Functionalizable Surface Platform With Reduced Nonspecific Protein Adsorption From Full Blood Plasma—Material Selection and Protein Immobilization Optimization," Biosensors and Siolectronics 24(7):1924-1930, Mar. 2009.
Voros, J., "The Density and Refractive Index of Adsorbing Protein Layers," Biophysical Journal 87(1):553-561, Jul. 2004.
Wang, X., et al., "Length Scale Heterogeneity in Lateral Gradients of Poly(N-isopropylacrylamide) Polymer Brushes Prepared by Surface-Initiated Atom Transfer Radical Polymerization Coupled With In-Plane Electrochemical Potential Gradients," Langmuir 22(2):817-823, Jan. 2006.
Yancey, P.H., et al., "Living With Water Stress: Evolution of Osmolyte Systems," Science 217(4566):1214-1222, Sep. 1982.
Yang, W., et al., "Pursuing 'Zero' Protein Adsorption of Poly(carboxybetaine) From Undiluted Blood Serum and Plasma," Langmuir 25(19):11911-11916, Oct. 2009.
Yu, Q., et al., "Detection of Low-Molecular-Weight Domoic Acid Using Surface Plasmon Resonance Sensor," Sensors and Actuators B 107(1):193-201, May 2005.
Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.
Zhang, Z., et al., "Nonfouling Behavior of Polycarboxybetaine-Grafted Surfaces: Structural and Environmental Effects," Biomacromolecules 9(10):2686-2692, Oct. 2008.
Zhao, C., et al., "Effect of Film Thickness on the Antifouling Performance of Poly(hydroxy-functional methacrylates) Grafted Surfaces," Langmuir 27(8):4906-4913, Apr. 2011.
Cao, A., et al., "Nanoparticles for Drug Delivery Prepared From Amphiphilic PLGA Zwitterionic Block Copolymers With Sharp Contrast in Polarity Between Two Blocks," Angewandte Chemie International Edition 49(22):3771-3776, May 2010.
Cheng, J., et al., "Formulation of Functionalized PLGA-PEG Nanoparticles for in Vivo Targeted Drug Delivery," Biomaterials 28(5):869-876, Feb. 2007.

Decision of Rejection, mailed Mar. 24, 2015, for Application No. JP 2012-538071, 6 pages.
Dimitrov, I., et al., "Thermosensitive Water-Soluble Copolymers With Doubly Responsive Reversibly Interacting Entities," Progress in Polymer Science 32(11):1275-1343, Nov. 2007.
Extended European Search Report dated Jan. 29, 2014, for Application No. EP 10829256.6, 10 pages.
First Japanese Office Action, dated Apr. 22, 2014, for Application No. JP 2012-538071, 9 pages.
Harris, J.M., "Introduction to Biotechnical and Biomedical Applications of Poly(Ethylene Glycol)," in J.M. Harris (ed.), "Poly(ethylene glycol) Chemistry," Plenum, New York, 1992, Chap. 1, pp. 1-14.
Hoffman, A.S., and B.D. Ratner, "2.13 Nonfouling Surfaces," in B.D. Ratner et al. (eds.), "Biomaterials Science: An Introduction to Materials in Medicine," 2nd ed., Elsevier, Amsterdam, 2004, pp. 197-201.
International Search Report and Written Opinion dated Aug. 12, 2008, for International Application No. PCT/US2007/089236, filed Dec. 31, 2007, 9 pages.
Juo, P.-S., "Concise Dictionary of Biomedicine and Molecular Biology," 2nd ed., CRC Press LLC, Boca Raton, Fla., 2002, p. 173.
Notification of the First Office Action, dated Aug. 21, 2013, for Application No. CN 201080055964.6, filed Nov. 8, 2010, 8 pages.
Tuzar, Z., et al., "Micelles of Hydrophilic-Hydrophobic Poly(Sulfobetaine)-Based Block Copolymers," Macromolecules 30(8)2509-2512, Apr. 1997.
Zhang, L.M., et al., "New Water-Soluble Ampholylic Polysaccharides for Oilfield Drilling Treatment: A Preliminary Study," Carbohydrate Polymers 44(3):255-260, Mar. 2001.
First Japanese Office Action, dated May 2, 2012, for Application No. JP 2009-544325, 4 pages.
Adams, E.W., et al., "Oligosaccharide and Glycoprotein Microarrays as Tools in HIV-Glycobiology: A Detailed Analysis of Glycan Dependent gp120/Protein Interactions," Chemistry & Biology 11(6):875-881, Jun. 2004.
Adden, N., et al., "Phosphonic Acid Monolayers for Binding of Bioactive Molecules to Titanium Surfaces," Langmuir 22(19):8197-8204, Aug. 2006.
Almeida, V.R., et al., "Guiding and Confining Light in Void Nanostructure," Optics Letters 29(11):1209-1211, Jun. 2004.
Almeida, V.R., et al., "Nanotaper for Compact Mode Conversion," Optics Letters 28(15):1302-1304, Aug. 2003.
Aprikian, P., et al., "Interdomain Interaction in the FimH Adhesin of *Escherichia coil* Regulates the Affinity to Mannose," Journal of Biological Chemistry 282(32):23437-23446, Aug. 2007.
Armani, A.M., et al., "Label-Free, Single-Molecule Detection With Optical Microcavities," Science 317(5839)183-787, Aug. 2007.
Baehr-Jones, T., et al., "High-Q Ring Resonators in Thin Silicon-on-Insulator," Applied Physics Letters 85(16):3346-3347, Oct. 2004.
Baehr-Jones, T., et al., "Nonlinear Polymer-Clad Silicon Slot Waveguide Modulator With a Half Wave Voltage of 0.25 V," Applied Physics Letters 92(16):163303-1-163303-3, Apr. 2008.
Baehr-Jones, T., et al., "Optical Modulation and Detection in Slotted Silicon Waveguides," Optics Express 13(14):5216-5226, Jul. 2005.
Boyraz, O., and B. Jalali, "Demonstration of a Silicon Raman Laser," Optics Express 12(21):5269-5273, Oct. 2004.
Browne, M.M., "Protein Adsorption Onto Polystyrene Surfaces Studied by XPS and AFM," Surface Science 553(1-3):155-167, Mar. 2004.
Canadian Office Action and Examination Search Report, dated Dec. 12, 2014, issued in Canadian Application No. 2.872.378, filed Jul. 20, 2012, 3 pages.
Castner, D.G., and B.D. Ratner, "Biomedical Surface Science: Foundations to Frontiers," Surface Science 500(1-3):28-60, Mar. 2002.
Cattani-Scholz, A., et al., "Organophosphonate-Based PNA-Functionalization of Silicon Nanowires for Label-Free DNA Detection," ACS Nano 2(8):1653-1660, Jul. 2008.
Chao, C.-Y., et al., "Polymer Microring Resonators for Biochemical Sensing Applications," IEEE Journal of Selected Topics in Quantum Electronics 12(1)134-142, Jan.-Feb. 2006.

(56) References Cited

OTHER PUBLICATIONS

Coen, M.C., et al., "Adsorption and Bioactivity of Protein A on Silicon Surfaces Studied by AFM and XPS," Journal of Colloid and Interface Science 233(2):180-189, Jan. 2001.
Communication Pursuant to Article 94(3) EPC dated Nov. 20, 2015, issued in corresponding European Application No. 12 814 998.6, filed Jul. 20, 2012, 7 pages.
Cook, A.D., et al., "Characterization and Development of RGD-Peptide-Modified Poly(lactic acid-co-lysine) as an Interactive, Resorbable Biomaterial," Journal of Biomedical Materials Research 35(4):513-523, Jun. 1997.
Crocker, P. R., et al., "Siglecs and Their Roles in the Immune System," Nature Reviews Immunology 7(4):255-266, Apr. 2007.
Davis, S.J., and J.F. Watts, "Interfacial Chemistry of Adhesive Joint Failure: An Investigation by Small Area XPS, Imaging XPS and TOF-SIMS," Journal of Materials Chemistry 6(3):479-493, Mar. 1996.
De Vos, K., et al., "Silicon-on-Insulator Microring Resonator for Sensitive and Label-Free Biosensing," Optics Express 15(12):7610-7615, Jun. 2007.
Dhayal, M., and D.M. Ratner, "XPS and SPR Analysis of Glycoarray Surface Density," Langmuir 25(4):2181-2187, Jan. 2009.
Disney, M.D., and P.H. Seeberger, "Aminoglycoside Microarrays To Explore Interactions of Antibiotics With RNAs and Proteins," Chemistry 10(13):3308-3314, Jul. 2004.
Disney, M.D., and P.H. Seeberger, "The Use of Carbohydrate Microarrays to Study Carbohydrate-Cell Interactions and to Detect Pathogens," Chemistry & Biology 11(12):1701-1707, Dec. 2004.
Dufrêne, Y.F., et al., "X-Ray Photoelectron Spectroscopy Analysis of Whole Cells and Isolated Cell Walls of Gram-Positive Bacteria: Comparison With Biochemical Analysis," Journal of Bacteriology 179(4):1023-1028, Feb. 1997.
European Search Report dated Feb. 12, 2015, issued in European Application No. 12814998.6, filed Jul. 20, 2012, 10 pages.
Kirk, J.T., et al., "Serologic and Phenotypic Analysis of Blood Types via Silicon Nanophotonics," Blood 124(21):1565-1565, Dec. 2014.
Fan, X., et al., "Overview of Novel Integrated Optical Ring Resonator Bio/Chemical Sensors," Proceedings of SPIE 6452:64520M-1-64520M-20, Feb. 2007.
Fang, A.W., et al., "Electrically Pumped Hybrid AlGaInAs-Silicon Evanescent Laser," Optics Express 14(20):9203-9210, Oct. 2006.
Fathpour, S., et al., "Energy Harvesting in Silicon Raman Amplifiers," Applied Physics Letters 89:061109-1-061109-3, Aug. 2006.
Karlsson, K.-A., "Bacterium-Host Protein-Carbohydrate Interactions and Pathogenicity," Biochemical Society Transactions 27(4):471-474, Aug. 1999.
Foster, M.A., et al., "Broad-Band Optical Parametric Gain on a Silicon Photonic Chip," Nature 441(7096):960-963, Jun. 2006.
Fukui, S., et al., "Oligosaccharide Microarrays for High-Throughput Detection and Specificity Assignments of Carbohydrate-Protein Interactions," Nature Biotechnology 20(10):1011-1017, Oct. 2002.
Gawalt, E.S., et al., "Bonding Organics to Ti Alloys: Facilitating Human Osteoblast Attachment and Spreading on Surgical Implant Materials," Langmuir 19(1):200-204, Jan. 2003.
Gohring, J.T., and X. Fan, "Label Free Detection of CD4+ and COB+ T Cells Using the Optofluidic Ring Resonator," Sensors 10(6):5798-5808, Jun. 2010.
Gong, P., et al., "Hybridization Behavior of Mixed DNA/Alkylthiol Monolayers on Gold: Characterization by Surface Plasmon Resonance and $^{32}$P Radiometric Assay," Analytical Chemistry 78(10):3326-3334, May 2006.
Gunn, C., "CMOS Photonics™ Technology: Enabling Optical Interconnects," Luxtera, Inc., Jan. 2012, <http://www.hotchips.org/archives/hc17/2_Mon/HC17.S3/HC17.S3T1.pdf> [retrieved Sep. 2015], 26 pages.
Guo, Y., et al., "Structural Basis for Distinct Ligand-Binding and Targeting Properties of the Receptors DC-SIGN and DC-SIGNR," Nature Structural & Molecular Biology 11(7):591-598, Jul. 2004.

Hanson, E.L., et al., "Bonding Self-Assembled, Compact Organophosphonate Monolayers to the Native Oxide Surface of Silicon," Journal of the American Chemical Society 125(51):16074-16080, Nov. 2003.
Herne, T.M., and M.J. Tarlov, "Characterization of Probe Immobilized on Gold Surface," Journal of the American Chemical Society 119(38):8916-8920, Sep. 1997.
Hess, J.R., and J.B. Holcomb, "Transfusion Practice in Military Trauma," Transfusion Medicine 18(3):143-150, Jun. 2008.
Hochberg, M., et al., "Terahertz All-Optical Modulation in a Silicon-Polymer Hybrid System," Nature Materials 5(9):703-709, Sep. 2006.
Holcomb, J.B., "Optimal Use of Blood Products in Severely Injured Trauma Patients," Hematology 2010(1):465-469, Dec. 2010.
Hölzl, M., et al., "Protein-Resistant Self-Assembled Monolayers on Gold With Latent Aldehyde Functions," Langmuir 23(10):5571-5577, May 2007.
Houseman, B.T., and M. Mrksich, "Carbohydrate Arrays for the Evaluation of Protein Binding and Enzymatic Modification," Chemistry & Biology 9(4):443-454, Apr. 2002.
Houseman, B.T., et al., "Maleimide-Functionalized Self-Assembled Monolayers for the Preparation of Peptide and carbohydrate Biochips," Langmuir 19(5):1522-1531, Mar. 2003.
International Search Report and Written Opinion dated Jan. 30, 2013, issued in corresponding International Application No. PCT/US2012/047745, filed Jul. 20, 2012, 8 pages.
Kansas, G.S., "Selectins and Their Ligands: Current Concepts and Controversies," Blood 88(9):3259-3287, Nov. 1996.
Ksendozov, A., and Y. Lin, "Integrated Optics Ring-Resonator Sensors for Protein Detection," Optics Letters 30(24):3344-3346, Dec. 2005.
Kumari, K., et al., "Receptor Binding Specificity of Recent Human H3N2 Influenza Viruses," Virology Journal 4:42, May 2007, 12 pages.
Lenigk, R., et al., "Surface Characterization of a Silicon-Chip-Based DNA Microarray," Langmuir 17(8):2497-2501, Mar. 2001.
Léonard, D., et al., "ToF-SIMS and XPS Study of Photoactivatable Reagents Designed for Surface Glycoengineering. Part III. 5-Carboxamidopentyl-N-[m-[3-(trifluoromethyl)diazirin-3-yl]phenyl-β-D-galactopyranosyl]-(1->4 )-1-thio-β-D-glucopyranoside (Lactose Aryl Diazirine) on Diamond," Surface and Interface Analysis 31(6):457-464, Jun. 2001.
Li, L., et al., "Harnessing Optical Forces in Integrated Photonic Circuits," Nature 456(7221):480-484, Nov. 2008.
Limpoco, F.T., and R.C. Bailey, "Real-Time Monitoring of Surface-Initiated Atom Transfer Radical Polymerization Using Silicon Photonic Microring Resonators: Implications for Combinatorial Screening of Polymer Brush Growth Conditions," Journal of the American Chemical Society 133(38):14864-14867, Sep. 2011.
Liu, A., et al., "A High-Speed Silicon Optical Modulator Based on a Metal-Oxide-Semiconductor Capacitor," Nature 427(6975):615-618, Feb. 2004.
Liu, A., et al., "Optical Amplification and Lasing by Stimulated Raman Scattering in Silicon Waveguides," IEEE Journal of Lightwave Technology 24(3):1440-1455, Mar. 2006.
Liu, J., et al., "Design of Monolithically Integrated GeSi Electroabsorption Modulators and Photodetectors on an SOI Platform," Optics Express 15(2):623-628, Jan. 2007.
Midwood, K.S., et al., "Easy and Efficient Bonding of Biomolecules to an Oxide Surface of Silicon," Langmuir 20(13):5501-5505, May 2004.
Non-Final Office Action dated Jul. 13, 2017, for U.S. Appl. No. 15/436,585, 7 pages.
Non-Final Office Action dated Sep. 29, 2017, for U.S. Appl. No. 15/396,128, 8 pages.
Noto, M., et al., "Detection of Protein Orientation on the Silica Microsphere Surface Using Transverse Electric/Transverse Magnetic Whispering Gallery Modes," Biophysical Journal 92(12):4466-4472, Jun. 2007.
Quan, Q., et al., "Photonic Crystal Nanobeam Cavity Strongly Coupled to the Feeding Waveguide," Applied Physics Letters 96(20):203102-1-203102-3, May 2010.

(56) References Cited

OTHER PUBLICATIONS

Ramachandran, A., et al., "A Universal Biosensing Platform Based on Optical Micro-Ring Resonators," Biosensors and Bioelectronics 23(7):939-944, Feb. 2008.
Ratner, D.M., et al., "Probing Protein-Carbohydrate Interactions With Microarrays of Synthetic Oligosaccharides," ChemBioChem 5(3):379-383, Mar. 2004.
Ratner, D.M., et al., "Tools for Glycomics: Mapping Interactions of Carbohydrates in Biological Systems," ChemBioChem 5(10):1375-1383, Oct. 2004.
Roelkens, G., et al., "Efficient Silicon-on-Insulator Fiber Coupler Fabricated Using 248-nm-Deep UV Lithography," IEEE Photonics Technology Letters 17(12):2613-2615, Dec. 2005.
Roelkens, G., et al., "High Efficiency Grating Coupler Between Silicon-on-Insulator Waveguides and Perfectly Vertical Optical Fibers," Optics Letters 32(11):1495-1497, Jun. 2007.
Rong, H., et al., "An All-Silicon Raman Laser," Nature 433(7023):292-294, Jan. 2005.
Sabbatini, L., and P.G. Zambonin, "XPS and SIMS Surface Chemical Analysis of Some Important Classes of Polymeric Biomaterials," Journal of Electron Spectroscopy and Related Phenomena 81(3):285-301, Sep. 1996.
Sacchettini, J.C., et al., "Multivalent Protein-Carbohydrate Interactions. A New Paradigm for Supermolecular Assembly and Signal Transduction," Biochemistry 40(10):3009-3015, Mar. 2001.
Salminen, A., et al., "Inhibition of P-Fimbriated *Escherichia coli* Adhesion by Multivalent Galabiose Derivatives Studied by a Live-Bacteria Application of Surface Plasmon Resonance," Journal of Antimicrobial Chemotherapy 60(3):495-501, Sep. 2007.
Sauer, U., et al., "Evaluation of Substrate Performance for a Microbial Diagnostic Microarray Using a Four Parameter Ranking," Analytica Chimica Acta 632(2):240-246, Jan. 2009.
Schmidt, B., et al., "Optical Trapping Platform Based on Highly Confining Silicon Waveguiding Structures With Microfluidics," Conference on Lasers and Electro-Optics and Conference on Quantum Electronics and Laser Science (CLEO/QELS), San Jose, Calif., May 4-9, 2008, OSA Technical Digest (CD), Optical Society of America, Paper CThQ3, 2 pages.
Sherwood-Droz, N., et al., "Optical 4x4 Hitless Silicon Router for Optical Networks-on-Chip (NoC)," Optics Express 16(20):15915-15922, Sep. 2008.
Silverman, B.M., et al., "Comparative Properties of Siloxane vs. Phosphonate Monolayers on a Key Titanium Alloy," Langmuir 21(1):225-228, Jan. 2005.
Summons to Attend Oral Proceedings dated Jun. 27, 2016, issued in corresponding European Application No. 12 814 998.6, filed Jul. 20, 2012, 8 pages.
Sun, R., et al., "Horizontal Single and Multiple Slot Waveguides: Optical Transmission at $\lambda$=1550 nm," Optics Express 15(26):17967-17972, Dec. 2007.
Tanabe, T., et al., "Trapping and Delaying Photons for One Nanosecond in an Ultrasmall High-Q Photonic-Crystal Nanocavity," Nature Photonics 1(1):49-52, Jan. 2007.
Thomas, W., "Catch Bonds in Adhesion," Annual Review of Biomedical Engineering 10:39-57, Aug. 2008.
Vollmer, F. et al., "Multiplexed DNA Quantification by Spectroscopic Shill of Two Microsphere Cavities,". Biophysical Journal 85(3):1974-1979, Sep. 2003.
Vollmer, F., et al., "Protein Detection by Optical Shift of a Resonant Microcavity," Applied Physics Letters 80(21):4057-4059, May 2002.
Von Muhlen, M.G., et al., "Label-Free Biomarker Sensing in Undiluted Serum With Suspended Microchannel Resonators," Analytical Chemistry 82(5):1905-1910, Mar. 2010.
Wang, D., et al., "Carbohydrate Microarrays for the Recognition of Cross-Reactive Molecular Markers of Microbes and Host Cells," Nature Biotechnology 20(3):275-281, Mar. 2002.
Wang, H., et al., "Probing the Orientation of Surface-Immobilized Immunoglobulin G by Time-of-Flight Secondary Ion Mass Spectrometry." Langmuir 20(5):1877-1887, Jan. 2004.
Wang, Y., and M. Lieberman, "Growth of Ultrasmooth Octadecyltrichlorosilane Self-Assembled Monolayers on $SiO_2$," Langmuir 19(4):1159-1167, Jan. 2003.
Washburn, A.L., and R.C. Bailey, "Photonics-on-a-Chip: Recent Advances in Integrated Waveguides as Enabling Detection Elements for Real-World, Lab-on-a-Chip Biosensing Applications," Analyst 136(2):227-236, Jan. 2011.
Xiao, S.-J., et al., "Covalent Attachment of Cell-Adhesive Peptides Containing (Arg-Gly-Asp) Sequences to Titanium Surfaces," Langmuir 14(19):5507-5516, Aug. 1998.
Xu, Q., and M. Lipson, "All-Optical Logic Based on Silicon Micro-Ring Resonators," Optics Express 15(3):924-929, Feb. 2007.
Xu, Q., et al., "Breaking the Delay-Bandwidth Limit in a Photonic Structure," Nature Physics 3(6):406-410, Apr. 2007.
Xu, Q., et al., "Experimental Demonstration of Guiding and Confining Light in Nanometer-Size Low-Refractive-Index Material," Optics Letters 29(14):1626-1628, Jul. 2004.
Yonzon, C.R., et al., "A Comparative Analysis of Localized and Propagating Surface Plasmon Resonance Sensors: The Binding of Concanavalin A to a Monosaccharide Functionalized Self-Assembled Monolayer," Journal of the American Chemical Society 126(39):12669-12676, Sep. 2004.
Yoshida, Y., et al., "Evidence of Chemical Bonding at Biomaterial-Hard Tissue Interfaces," Journal of Dental Research 79(2):709-714, Feb. 2000.
Yu, R.K., and M. Yanagisawa, "Glycobiology of Neural Stem Cells," CNS & Neurological Disorders Drug Targets 5(4):415-423, Aug. 2006.
Zhao, Y.-D., et al., "DNA-Modified Electrodes. Part 4: Optimization of Covalent Immobilization of DNA on Self-Assembled Monolayers," Talanta 49(4):751-756, Jul. 1999.
Zhu, H., et al., "Opto-Fluidic Micro-Ring Resonator for Sensitive Label-Free Viral Detection," Analyst 133(3):356-360, Mar. 2008.

* cited by examiner

HIERARCHICAL FILMS HAVING ULTRA LOW FOULING AND HIGH RECOGNITION ELEMENT LOADING PROPERTIES

CROSS-REFERENCE TO RELATED APPLICATION

This application claims the benefit of U.S. Provisional Application No. 61/588,785, filed Jan. 20, 2012, expressly incorporated herein by reference in its entirety.

STATEMENT OF GOVERNMENT LICENSE RIGHTS

This invention was made with Government support under HDTRA1-10-1-0074 awarded by the Defense Threat Reduction Agency and under N000140910137 awarded by the Office of Naval Research. The Government has certain rights in the invention.

BACKGROUND OF THE INVENTION

Surface chemistries for biosensors, implantable medical devices, targeted drug/gene delivery carriers, tissue scaffolds, and targeted molecular imaging probes in complex media remain a great challenge due to high nonspecific adsorption and low binding capacity of molecular recognition elements. Currently, few materials have been developed to reduce nonspecific protein adsorption, including poly(ethylene glycol) (PEG), mannitol tetraglyme, and zwitterionic polymers. The effectiveness of protein resistant materials relies on their high surface packing densities. Unfortunately, highly dense two-dimensional (2D) polymer films elicit the limitation of a low ligand-binding capacity. At the same time, a three-dimensional (3D) carboxymethylated dextran-based hydrogel binding matrix was previously developed, enabling very high protein loading due to an open polymer structure. However, this open structure only provides weak surface resistance to nonspecific protein adsorption, particularly in complex media such as blood.

Despite the advances in the development polymer films noted above, there is a need for polymer films with precisely controlled architecture for achieving advantageous properties for a variety of applications. The present invention seeks to fulfill this need and provides further related advantages.

SUMMARY OF THE INVENTION

In one aspect, the invention provides hierarchical films.

In one embodiment, the film comprises a first layer having a first layer density, wherein the first layer is attached to a substrate; and a second layer having a second layer density, wherein the second layer is attached to the first layer, wherein the first layer density is greater than the second layer density.

In another embodiment, the film comprises a first nonfouling layer (low level of fibrinogen or lysozyme nonspecific binding), wherein the first layer is attached to a substrate; and a second layer that can be functionalized to include recognition elements, wherein the second layer is attached to the first layer.

In certain embodiments, the second layer of the films of the invention further comprises a plurality of recognition elements. Representative recognition elements include peptides, proteins, nucleic acids, and small molecules. In certain embodiments, the recognition element is an antibody or antibody fragment, or a DNA or an RNA.

In certain embodiments, the first layer comprises a plurality of polymers. In one embodiment, the first layer is a polymer brush. In certain embodiments, the first layer is a nonfouling layer. In certain embodiments, the first layer has a fibrinogen binding level less than about 30 ng/cm$^2$. In other embodiments, the first layer has a lysozyme binding level less than about 30 ng/cm$^2$. In certain embodiments, the first layer comprises a first polymer layer having a first polymer density, and the first polymer layer comprises a plurality of first polymers, each of the first polymers having a first end and a second end, wherein each first polymer is attached to a substrate through its first end. In certain embodiments, the first polymers are grafted from the substrate. In other embodiments, the first polymers are grafted to the substrate.

In certain embodiments, the second layer comprises a plurality of polymers. In certain of these embodiments, the second layer is a crosslinked layer (e.g., a hydrogel). In certain embodiments, the second layer comprises a second polymer layer having a second polymer density, wherein the second polymer layer comprises a plurality of second polymers, each of the second polymers having a first end and a second end, wherein each second polymer is attached to a first polymer through its first end. In certain embodiments, the second polymers are grafted from the first polymers. In other embodiments, the second polymers are grafted to the first polymers.

The first or second polymers are independently selected from charged polymers and copolymers and non-charged polymers and copolymers. Representative charged polymers and copolymers include zwitterionic polymers and copolymers and mixed charge copolymers. Representative zwitterionic polymers include polysulfobetaines, polycarboxybetaines, polyphosphobetaines, peptides, and peptoids. Representative non-charged polymers include alkylene oxide polymers and copolymers (e.g., PEGs), polysaccharide polymers and copolymers (e.g., dextrans), acrylamide polymers and copolymers (e.g., acrylamide and methacrylamide polymers and copolymers), and hydroxy-terminal polymers and copolymers (e.g., HEMA and HPMA).

In certain embodiments, the films of the invention include one or more additional layers attached to the second layer.

In the films of the invention, the first layer is attached to a substrate surface. Suitable surfaces include metal and metal oxide surfaces, ceramic surfaces, synthetic and natural polymeric surfaces, glass surfaces, fiber glass surfaces, silicon/silica surfaces, carbon-based material surfaces, cell surfaces, and macromolecule surfaces (e.g., protein, DNAs, lipids). Representative substrates include diagnostic devices, medical devices, separation devices, targeting delivery carriers, tissue scaffolds, and marine devices.

In another aspect, methods for making the films of the invention are provided. In one embodiment, the method includes forming a first layer having a first layer density on a substrate; and forming a second layer on the first layer, the second layer having a second density, wherein the first layer density is greater than the second layer density. In certain embodiments, the method further comprises attaching a plurality of recognition elements to the second layer. In other embodiments, the method further comprises attaching one or more additional layers to the second layer.

In certain embodiments, forming the first layer comprises grafting first polymers from the substrate. In other embodiments, forming the first layer comprises grafting first polymers to the substrate.

In certain embodiments, forming the second layer comprises grafting the second polymers from the first polymers.

In other embodiments, forming the second layer comprises grafting the second polymers to the first polymers.

In a further aspect, the invention provides methods for determining the presence of an analyte in a sample. In one embodiment, the method comprises contacting a sample with a film of the invention comprising one or more recognition elements, wherein the recognition element has a specific binding affinity for the analyte, and interrogating the film to determine whether the analyte has bound to the film.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 5A illustrates a single layer 2D pCB platform having excellent nonfouling properties, but low antibody loading (left panel) and a commercial dextran platform having high antibody loading, but poor nonfouling properties (right panel). FIG. 5B is a schematic illustration of a representative two-layer film of the invention having a first dense pCB layer to resist nonspecific adsorption and a second loose (less dense) pCB layer to achieve high antibody loading.

DETAILED DESCRIPTION OF THE INVENTION

Figure 1:
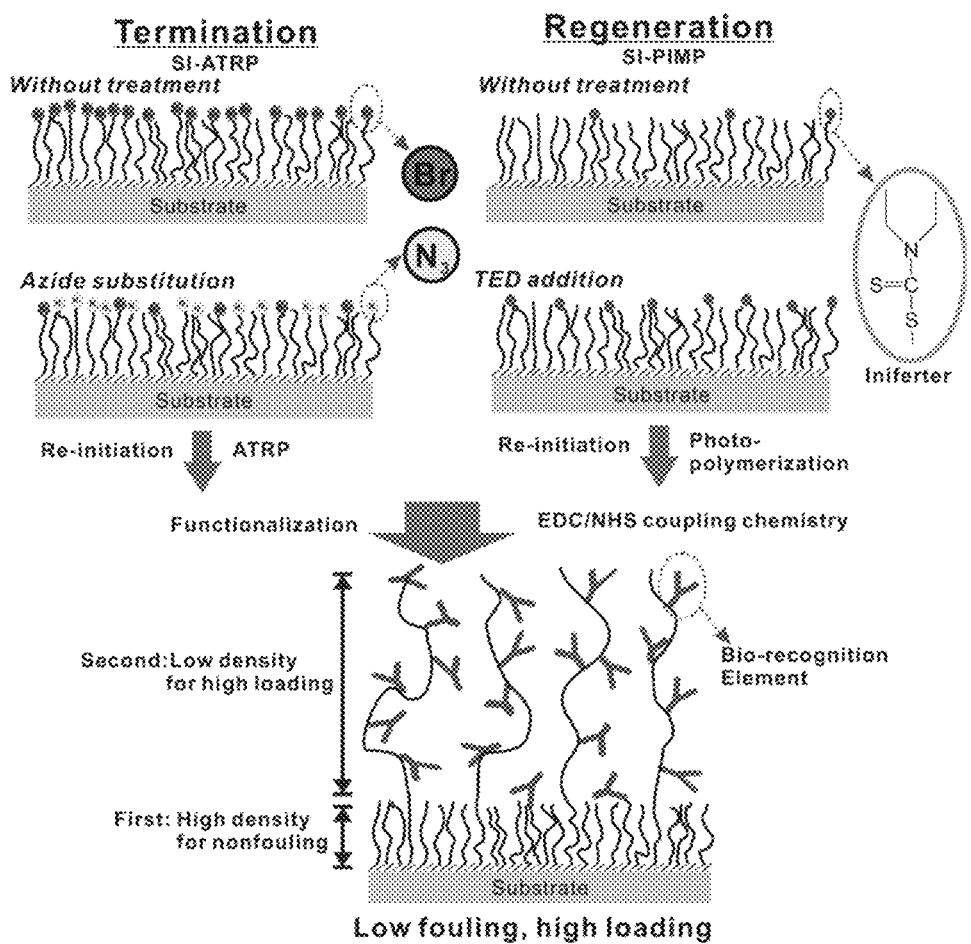
FIG. 1 is a schematic illustration of a representative polymer film of the invention having an ultra low fouling first layer and high-loading second layer.

The present invention provides hierarchical films with structurally regulated functionalities through the integration of two-dimensional and three-dimensional structures to achieve ultra low nonspecific binding and high loading of molecular recognition elements. Methods for making and using the films are also provided.

As used herein, the term "hierarchical" refers to the layered architecture of the films, where the individual layers have specific functions and properties.

The present invention provides dual-functional nonfouling films, methods for making dual-functional nonfouling films, and devices that include dual-functional nonfouling films. The dual-functional films of the invention are films that are nonfouling (e.g., ultra low-fouling) surfaces that resist non-specific protein adsorption and cell adhesion. The dual-functional films of the invention also include covalently coupled recognition elements (e.g., target binding partners) that impart specific binding activity to the surfaces. Because the dual-functional films of the invention are non-fouling and include immobilized recognition elements, these films are useful in any method or device that requires sensitive specific binding or specific binding measurement and at the same time requires resistance to non-specific protein binding and cell adhesion. The dual-functional films of the invention are useful in medical diagnostic applications, biomaterials and tissue engineering, and drug delivery.

Dual-Functional Films

In one aspect, the invention provides a film that includes two layers: a first layer having a first layer density and attached to a substrate; and a second layer having second density and attached to the first layer. In certain embodiments, the density of the first layer is greater than the density of the second layer. In other embodiments, the film comprises a first nonfouling layer (low level of fibrinogen or lysozyme non-specific binding as described below), wherein the first layer is attached to a substrate; and a second layer that can be functionalized to include recognition elements, wherein the second layer is attached to the first layer. In preferred embodiments, the second layer of the films of the invention includes a plurality of recognition elements.

The terms "film," "coating," and "surface coating" are used interchangeably and refer the constructs of the invention having two layers as described above.

In certain embodiments, the first layer is a nonfouling layer. As used herein, the terms "nonfouling" and "ultra low fouling" refers to layers and films of the invention that resist or prevent non-specific protein adsorption and cell adhesion. Non-specific protein adsorption can be measured by determining the level of protein (e.g., fibrinogen or lysozyme) adsorption that adsorbs to the surface per unit area.

The first layer of the films of the invention adsorb less than about 30 ng/cm$^2$ fibrinogen or lysozyme. In one embodiment, the first layer has a fibrinogen or lysozyme adsorption less than about 10 ng/cm$^2$; in one embodiment, the fibrinogen or lysozyme adsorption is less than about 5 ng/cm$^2$; in one embodiment, the fibrinogen or lysozyme adsorption is less than about 3 ng/cm$^2$; and in one embodiment, the fibrinogen or lysozyme adsorption is less than about 0.3 ng/cm$^2$.

The nonfouling function of the film is imparted to the first layer by the materials of the first layer coupled to the surface. These materials include zwitterionic materials. Suitable materials useful in making the surfaces include the polymers and copolymers described in U.S. Pat. No. 7,879,444 (Superlow-Fouling Sulfobetaine and Carboxybetaine Materials and Related Methods) and US 20090259015 (Mixed Charge Copolymers and Hydrogels), each expressly incorporated herein by reference in its entirety. Methods for measuring protein adsorption (fibrinogen) are described in U.S. Pat. No. 7,879,444, expressly incorporated herein by reference.

The thickness of the first layer of the film of the invention can vary depending on the intended use of the film. In certain embodiments, the first layer has a thickness from about 1 to about 100 nm. In certain other embodiments, the first layer has a thickness from about 1 to about 20 nm.

The second layer of the films of the invention is attached to the film's first layer and has a density less than the density of the first layer. In certain embodiments, recognition elements are attached to the second layer to render the films dual-functional films. In these embodiments, the second layer includes materials having a functional group or groups suitably reactive to immobilize recognition elements (e.g., proteins such as antibodies). Representative functional groups for these dual-functional materials include carboxylic acid groups and amino groups, among others. As described in detail below, in one embodiment, the dual-functional materials are zwitterionic materials that can be attached (e.g., covalently coupled) to a surface and that have terminal carboxylic acid groups. These terminal carboxylic acid groups can be activated for coupling to one or more amino groups present in a biomolecule. In this embodiment, the carboxylic acid groups may be converted to active esters (e.g., N-hydroxysuccinimide esters) and then reacted with one or more amino groups (e.g., amino group of a lysine residue of a protein) to form an amide bond thereby immobilizing the protein to the surface to provide a dual-functional film of the invention.

Figure 10A:
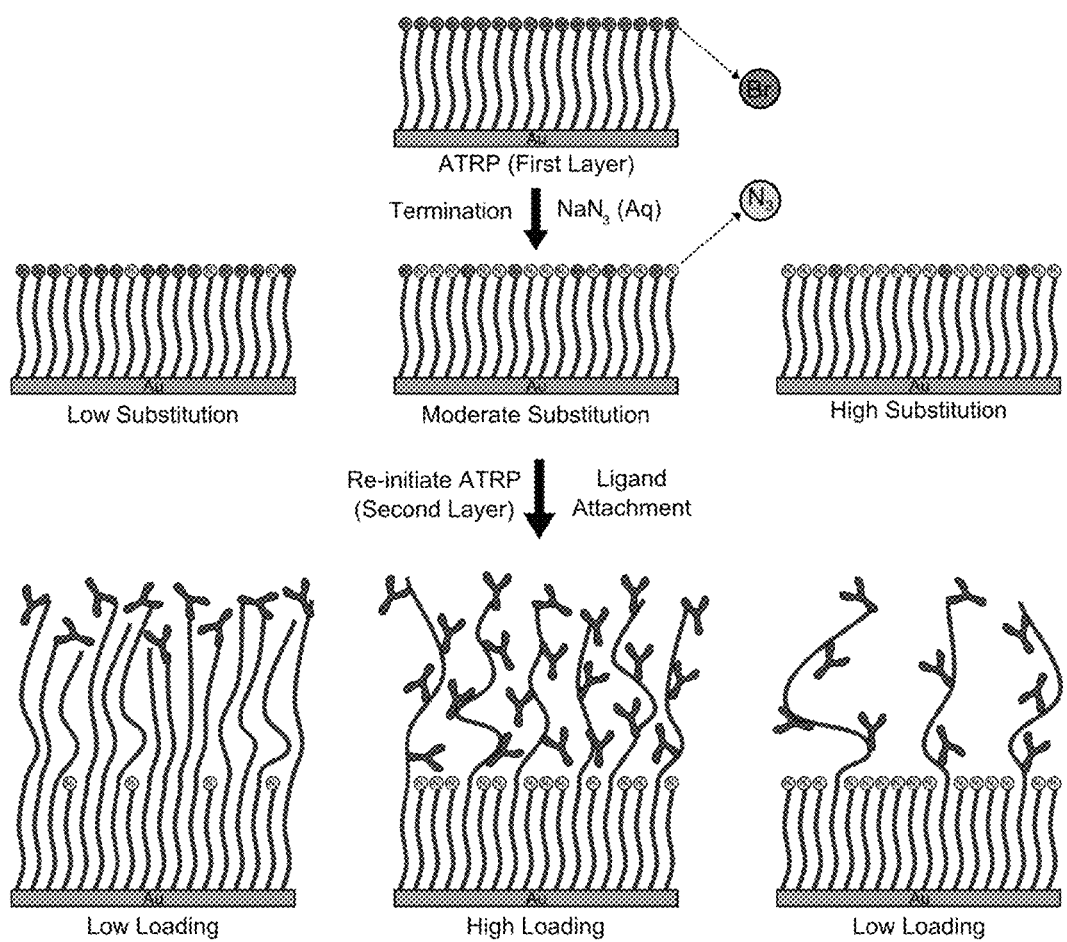
FIG. 10A is a schematic illustration of the preparation of representative films of the invention for sensing and detection in undiluted complex media using a two-layer architecture integrated with zwitterionic dual-functional pCB.
Figure 10B:
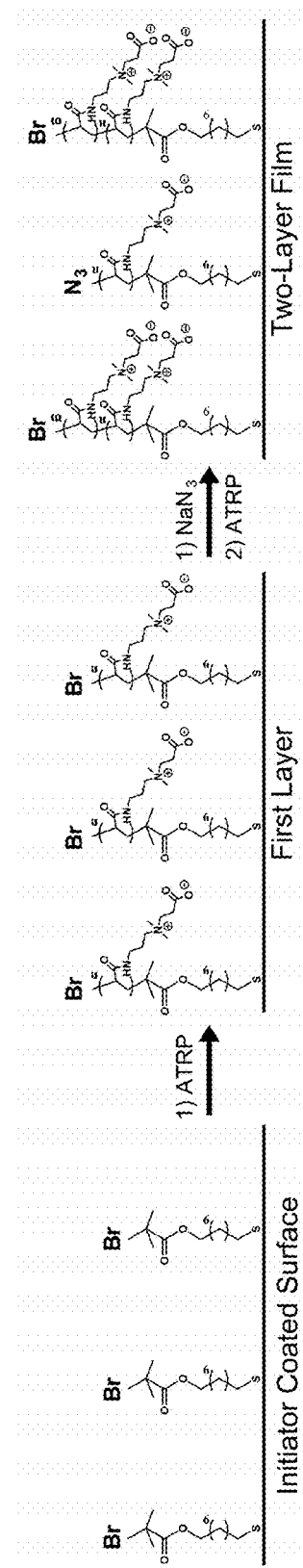
FIG. 10B is a schematic illustration of the preparation of representative films of the invention.

In the second layer, the materials can include carboxylic acid groups and certain of these carboxylic acid groups are available for further chemical reaction, specifically the immobilization of recognition elements (i.e., target binding partners) to the materials and, therefore, the film. In certain embodiments, recognition elements having available amino groups (—NH$_2$) can be covalently coupled to the materials' available carboxylic acid groups to immobilize the recognition element through stable amide linkages (—CONH—). In the practice of the invention, a portion of the materials having available carboxylic acid groups are activated for coupling and then covalently coupled to the recognition elements to provide immobilized recognition elements. The extent of recognition elements immobilized to the films of the invention can be readily controlled through the reaction conditions (e.g., extent of carboxyl group activation and concentration and amount of recognition elements exposed to the activated layer for immobilization. Schematic illustrations of representative nonfouling films of the invention having immobilized recognition elements are shown in FIGS. 1, 10A, and 10B. It will be appreciated that in certain circumstances, due to the difference in densities between the second and first layers and the nature of the first layer, recognition elements may be attached to the first layer.

The thickness of the second layer of the film of the invention can also vary depending on the intended use of the film. In certain embodiments, the second layer has a thickness from about 10 nm to about 300 μm. In certain other embodiments, the second layer has a thickness from about 100 nm to about 100 μm.

It will be appreciated that films with additional layers (e.g., third, fourth, fifth layers) are within the scope of the invention. The additional layers can be formed on the two-layer film described herein. For example, the third layer can be formed on the second layer (e.g., by "graft from" or "graft to" techniques). Subsequent layers can be similarly formed.

Polymer Films

Representative films of the invention include polymer films. As used herein, the term "polymer film" refers to a film of the invention in which the first layer is a polymer layer, the second layer is a polymer layer, or the first and second layers are polymer layers.

In certain embodiments, the first layer comprises a plurality of polymers. For these embodiments, the first layer is a polymer layer. Suitable polymers layers include polymer brushes. As used herein, the term "polymer brush" refers to an assembly of polymer chains in which an end of each polymer chain is attached to a substrate surface.

The second layer may also comprise a plurality of polymers. For these embodiments, the second layer is a polymer layer. In certain of these embodiments, the second layer is a crosslinked polymer layer and, in certain of these embodiments, the second layer is a hydrogel.

As noted above, in certain embodiments, the films of the invention, the density of the first layer is greater than the density of the second layer.

As noted above, in certain embodiments, the first layer of the films of the invention have a density greater than the density of the second layer. As used herein, the term "density" has its common meaning: mass per unit volume. The greater density of the first layer of films of the invention is readily apparent from the schematic illustrations of representative films in FIG. 10A. Referring to FIG. 10A, because not every first polymer in the first layer is attached to a second polymer in the second layer, the density of the second layer is necessarily less than the density of the first layer.

The density of layers can be determined by refractive index or swelling ratio as described herein. Representative films of the invention have a dry film refractive index from about 1.40 to about 1.57 RIU. In one embodiment, the dry film refractive index is greater than about 1.45 RIU. In another embodiment, the dry film refractive index is greater than about 1.48 RIU. In a further embodiment, the dry film refractive index is greater than about 1.50 RIU. Dry film refractive index is measured as described in Example 4. See also FIG. 16. Representative films of the invention have a swelling ratio from about 1 to about 5. In one embodiment, the swelling ratio is less than about 4. In another embodiment, the swelling ratio is less than about 3. In a further embodiment, the swelling ratio is less than about 2.5. Swelling ratio is measured as described in Example 5. See FIGS. 15A and 15B.

In other embodiments, the film comprises a first nonfouling layer (low level of fibrinogen or lysozyme non-specific binding), wherein the first layer is attached to a substrate; and a second layer that can be functionalized to include recognition elements, wherein the second layer is attached to the first layer. In this embodiment, the first layer need not have a density that is greater than the second layer.

For certain polymer films of the invention, the first layer comprises a first polymer layer having a first polymer density, and the first polymer layer comprises a plurality of first polymers, each of the first polymers having a first end and a second end, wherein each first polymer is attached to a substrate through its first end.

Similarly, for certain polymer films of the invention, the second layer comprises a second polymer layer having a second polymer density, and the second polymer layer comprises a plurality of second polymers, each of the second polymers having a first end and a second end, wherein each second polymer is attached to a first polymer's second end through the second polymer's first end.

In certain embodiments, the polymer film of the invention includes a first layer comprising a first polymer layer having a first polymer density, the first polymer layer comprising a plurality of first polymers, each of the first polymers having a first end and a second end, wherein each first polymer is attached to a substrate through its first end; and a second layer comprising a second polymer layer having a second polymer density, wherein the second polymer layer comprises a plurality of second polymers, each of the second polymers having a first end and a second end, wherein each second polymer is attached to a first polymer's second end through the second polymer's first end.

As described above, the polymers are attached end to end (first polymer first end attached to the substrate, and first polymer second end attached to second polymer first end), it will be appreciated that the polymers need not be attached end to end. In certain embodiments the polymers can be attached through attachment sites that are not at the polymer end (terminus). The attachment sites can be near the polymer end or, for example, near the middle of the polymer.

In certain embodiments, the first polymers are grafted from the substrate surface. As used herein, the term "grafted from" refers to an attachment method in which the polymer is formed from the substrate. In this embodiment, each of the first polymers are formed by polymerization from the substrate. Suitable polymerization methods include free radical polymerization, atom transfer radical polymerization (ATRP), reverse addition fragment transfer (RAFT), photoiniferter-mediated polymerization (PIMP), and condensation/ring opening polymerization.

In other embodiments, the first polymers are grafted to the substrate surface. As used herein, the term "grafted to" refers to an attachment method in which the first polymer is attached to the substrate surface. In this embodiment, each of the first polymers are first formed and then attached to the substrate surface. The nature of the attachment of the first polymer to the substrate surface is not critical; the attachment site of each of the first polymer and substrate is suitably reactive to the other. In certain embodiments, the first polymer is attached to the substrate surface by click chemistry. See, for example, http://onlinelibrary.wiley.com/doi/10.1002/1521-3773(20010601)40:11%3C2004::AID-ANIE2004%3E3.0.CO;2-5/full. In other embodiments, the first polymer is attached to the substrate surface by thiol-ene chemistry. See, for example, http://onlinelibrary.wiley.com/doi/10.1002/anie.200903924/full. In certain embodiments, non-covalent association (e.g., ionic, hydrophobic, hydrogen bonding, or mechanical methods such as entanglement) are effective graft to methods.

In certain embodiments, the second polymers are grafted from the first polymers. This refers to an attachment method in which the second polymer is formed from the first polymer. In this embodiment, each of the second polymers are formed by polymerization from a first polymer. Suitable polymerization methods include free radical polymerization, atom transfer radical polymerization (ATRP), reverse addition fragment transfer (RAFT), photoiniferter-mediated polymerization (PIMP), and condensation/ring opening polymerization.

In other embodiments, the second polymers are grafted to the first polymers. This refers to an attachment method in which the second polymer is attached to the first polymer. In this embodiment, each of the second polymers are first formed and then attached to a first polymer. The nature of the attachment of the second polymer to the first polymer is not critical; the attachment site of each of the first and second polymers is suitably reactive to the other. In certain embodiments, the second polymer is attached to the first polymer by click chemistry. In other embodiments, the second polymer is attached to the first polymer by thiol-ene chemistry. As noted above, in certain embodiments, non-covalent association (e.g., ionic, hydrophobic, hydrogen bonding, or mechanical methods such as entanglement) are effective graft to methods.

In the above methods, the second polymer may be attached to the first polymer by covalent coupling the second polymer to the first polymer.

Graft from ATRP and PIMP methods for making films of the invention are described below and in Examples 1-3.

The specific polymers making up the first and second layers is not critical so long as the properties of each layer are maintained as described above. Suitable first and second polymers include charged polymers and copolymers and non-charged polymers and copolymers. Suitable charged polymers include zwitterionic polymers and copolymers and mixed charge copolymers. Suitable non-charged polymers and copolymers include alkylene oxide polymers and copolymers, polysaccharide polymers and copolymers (dextrans), acrylamide polymers and copolymers, and hydroxyterminal polymers and copolymers (HEMA). Representative zwitterionic polymers useful in the first and second layers include polysulfobetaines, polycarboxybetaines, polyphosphobetaines, peptides, and peptoids. Representative zwitterionic polymers useful in the second layer include polycarboxybetaines and mixed charge peptides.

In some embodiments, the first polymers are selected from polysulfobetaines, polycarboxybetaines, polyphosphobetaines, and peptides, and the second polymers are selected from polycarboxybetaines and peptides. In other embodiments, the first polymers are polycarboxybetaines and the second polymers are polycarboxybetaines.

In certain embodiments, the first and/or second polymers of the first and second layers of the polymer film of the invention are zwitterionic polymers. In the practice of the invention, these polymers may be prepared by polymerization of a zwitterionic (or latent zwitterionic) monomer.

Representative zwitterionic first or second polymers have the formula:

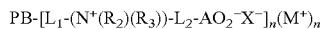

wherein

PB is the polymer backbone having n pendant zwitterionic groups;

$R_2$ and $R_3$ are independently selected from the group consisting of hydrogen, alkyl, and aryl, or taken together with the nitrogen to which they are attached form a cationic center;

$L_1$ is a linker that covalently couples the cationic center $[N^+(R_5)(R_6)]$ to the polymer backbone;

$L_2$ is a linker that covalently couples the anionic center $[A(=O)-O^-]$ to the cationic center;

A is C, S, SO, P, or PO;

$M^+$ is an optional counter ion associated with the $(A=O)O^-$ anionic center;

$X^-$ is an optional counter ion associated with the cationic center; and n is an integer from 1 to about 10,000.

Representative zwitterionic first or second polymers comprise a plurality of repeating units, each repeating unit having the formula:

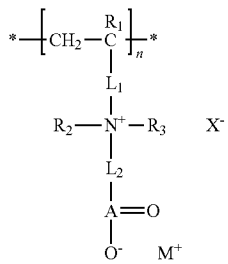

wherein $R_1$ is selected from the group consisting of hydrogen, fluorine, trifluoromethyl, C1-C6 alkyl, and C6-C12 aryl groups;

$R_2$ and $R_3$ are independently selected from the group consisting of hydrogen, alkyl, and aryl, or taken together with the nitrogen to which they are attached form a cationic center;

$L_1$ is a linker that covalently couples the cationic center $[N^+(R_5)(R_6)]$ to the polymer backbone $[-(CH_2-CR_4)_n-]$;

$L_2$ is a linker that covalently couples the anionic center $[A(=O)-O^-]$ to the cationic center;

A is C, S, SO, P, or PO;

$M^+$ is an optional counter ion associated with the $(A=O)-O^-$ anionic center;

$X^-$ is an optional counter ion associated with the cationic center; and n is an integer from 1 to about 10,000.

In one embodiment, the polymer is a polycarboxybetaine. Suitable polycarboxybetaines can be prepared from one or more monomers selected from the group consisting of carboxybetaine acrylates, carboxybetaine acrylamides, carboxybetaine vinyl compounds, carboxybetaine epoxides, and mixtures thereof. In one embodiment, the monomer is carboxybetaine methacrylate. Representative monomers for making carboxybetaine polymers useful in the invention include carboxybetaine methacrylates, such as 2-carboxy-N,N-dimethyl-N-(2'-methacryloyloxyethyl) ethanaminium inner salt; carboxybetaine acrylates; carboxybetaine acrylamides; carboxybetaine vinyl compounds; carboxybetaine epoxides; and other carboxybetaine compounds with hydroxyl, isocyanates, amino, or carboxylic acid groups. In one embodiment, the polymer is a poly(carboxybetaine methacrylate) (poly(CBMA)). In another embodiment, the polymer is a poly(carboxybetaine acrylate) (poly(CBAA)).

In other embodiments, the first and/or second polymers of the first and second layers of the polymer film of the invention are mixed charge copolymers.

As used herein, the term "mixed charge copolymer" refers to a copolymer having a polymer backbone, a plurality of positively charged repeating units, and a plurality of negatively charged repeating units.

The mixed charge copolymer includes a plurality of positively charged repeating units, and a plurality of negatively charged repeating units. In one embodiment, the mixed charge copolymer is substantially electronically neutral. As used herein, the term "substantially electronically neutral" refers to a copolymer that imparts advantageous nonfouling properties to the copolymer. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9. In the practice of the invention, these copolymers may be prepared by polymerization of an ion-pair comonomer.

In one embodiment, the copolymers are prepared by copolymerization of suitable polymerizable ion pair comonomers.

Representative ion-pair comonomers useful in the invention have the formulas:

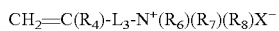

Representative mixed charge first or second polymers have the formula:

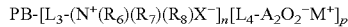

$PB-[L_3-(N^+(R_6)(R_7)(R_8)X^-]_n[L_4-A_2O_2^-M^+]_p$ wherein

PB is the polymer backbone having n pendant cationic groups and p pendant anionic groups;

$R_6$, $R_7$, and $R_8$ are independently selected from hydrogen, alkyl, and aryl, or taken together with the nitrogen to which they are attached form a cationic center;

A(=O)—OM) is an anionic center, wherein A is C, S, SO, P, or PO, and $M^+$ is an optional counter ion;

$L_3$ is a linker that covalently couples the cationic center $[N^+(R_6)(R_7)(R_8)]$ to the polymer backbone;

$L_4$ is a linker that covalently couples the anionic center [A(=O)—OM] to the polymer backbone;

$X^-$ is an optional counter ion associated with the cationic center;

n is an integer from 1 to about 10,000; and p is an integer from 1 to about 10,000.

Representative mixed charge first or second polymers comprise a plurality of repeating units, the copolymer having the formula:

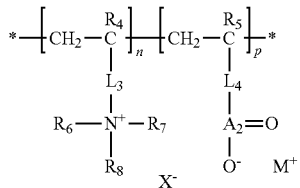

wherein $R_4$ and $R_5$ are independently selected from hydrogen, fluorine, trifluoromethyl, C1-C6 alkyl, and C6-C12 aryl groups;

$R_6$, $R_7$, and $R_8$ are independently selected from hydrogen, alkyl, and aryl, or taken together with the nitrogen to which they are attached form a cationic center;

A(=O)—OM) is an anionic center, wherein A is C, S, SO, P, or PO, and $M^+$ is an optional counterion;

$L_3$ is a linker that covalently couples the cationic center $[N^+(R_6)(R_7)(R_8)]$ to the polymer backbone;

$L_4$ is a linker that covalently couples the anionic center [A(=O)—OM] to the polymer backbone;

$X^-$ is an optional counter ion associated with the cationic center;

n is an integer from 1 to about 10,000; and p is an integer from 1 to about 10,000.

As noted above, in certain embodiments, $M^+$ and $X^-$ are optional as the cationic center and the anionic center provide an inner salt.

For the above formulas illustrating polymer repeating units, * represents the point at which each repeating unit is covalently linked to the next.

In the above formulas, the polymer backbone (PB) may be any one of a variety of backbones known to those of skill in the art (e.g., acrylic acid, alkylacrylic acid, such as methacrylic acid; acrylamide, alkylacrylamide such as methacrylamide). The nature of the polymer backbone is not critical. Suitable backbones include vinyl backbones (i.e., —C(R')(R'')—C(R''')(R'''')—, where R', R'', R''', and R'''' are independently selected from hydrogen, alkyl, and aryl) derived from vinyl monomers (e.g., acrylate, methacrylate, acrylamide, methacrylamide, styrene). Other suitable backbones include polyamide backbones, such as poly(amino acid) backbones.

In the above formulas, $N^+$ is the cationic center. In certain embodiments, the cationic center is a quaternary ammonium (e.g., N bonded to $L_1$, $R_2$, $R_3$, and $L_2$). In addition to ammonium, other useful cationic centers (e.g., $R_2$ and $R_3$ taken together with N) include imidazolium, triazaolium, pyridinium, morpholinium, oxazolidinium, pyrazinium, pyridazinium, pyrimidinium, piperazinium, and pyrrolidinium.

$R_1$-$R_8$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_2$ and $R_3$, and $R_6$, $R_7$, and $R_8$, are methyl. In one embodiment, $R_1$-$R_8$ are methyl. Representative aryl groups include C6-C12 aryl groups including, for example, phenyl. For certain embodiments of the above formulas, $R_2$ and $R_3$, and/or $R_6$, $R_7$, and $R_8$ are taken together with $N^+$ form the cationic center. In one embodiment, $R_7$ and $R_8$ are C1-C3 alkyl. In another embodiment, $R_6$, $R_7$, and $R_8$ are C1-C3 alkyl.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomers). In addition to the functional group, $L_1$ can include an C1-C20 alkylene chain. Representative $L_1$ groups include —C(=O)O—$(CH_2)_n$— and —C(=O)NH—$(CH_2)_n$—, where n is 1-20 (e.g., n=2).

$L_2$ is a linker that covalently couples the cationic center to the anionic group. $L_2$ can be a C1-C20 alkylene chain. Representative $L_2$ groups include —$(CH_2)_n$—, where n is 1-20 (e.g., 1, 3, or 5).

$L_3$ is a linker that covalently couples the cationic center to the polymer backbone. In certain embodiments, $L_3$ includes a functional group (e.g., ester or amide) that couples the remainder of $L_3$ to the polymer backbone (or polymerizable moiety for the monomers). In addition to the functional group, $L_3$ can include an C1-C20 alkylene chain. Representative $L_3$ groups include —C(=O)O—$(CH_2)_n$— and —C(=O)NH—$(CH_2)_n$—, where n is 1-20 (e.g., n=2). In certain embodiments, $L_3$ is —C(=O)O—$(CH_2)_n$—, wherein n is 1-6.

$L_4$ is a linker that covalently couples the anionic group to the polymer backbone. In certain embodiments, $L_4$ is a C1-C20 alkylene chain. Representative $L_4$ groups include —$(CH_2)_n$—, where n is 1-20 (e.g., 1, 3, or 5).

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl).

Representative aryl groups include C6-C12 aryl groups including, for example, phenyl including substituted phenyl groups (e.g., benzoic acid).

$X^-$ is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19);

salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions include salicylic acid (2-hydroxybenzoic acid), benzoate, and lactate.

In certain embodiments, A is C or SO.

In certain embodiments, n is an integer from 5 to about 5,000.

In one embodiment, $R_4$, $R_5$, $R_6$, $R_7$, and $R_8$ are methyl, $L_3$ is —C(=O)O—$(CH_2)_2$—, and $L_4$ is —$CH_2$—, $A_1$ is C or SO, and n is an integer from 5 to about 5,000.

For the zwitterionic polymers and mixed charge copolymers useful in the invention, the degree of polymerization (DP or n), number average molecular weight ($M_n$), and the ratio of weight average and number average molecular weights ($M_w/M_n$), also known as polydispersity index, can vary. In one embodiment, the polymers have a degree of polymerization (n) from 1 to about 10,000. In one embodiment, n is from about 10 to about 5,000. In another embodiment, n is from about 100 to about 3,500. In one embodiment, the polymers have a number average molecular weight ($M_n$) of from about 200 to about 2,000,000 Da. In one embodiment, $M_n$ is from about 2,000 to about 100,000 Da. In another embodiment, $M_n$ is from about 20,000 to about 80,000 Da. In one embodiment, the polymers have a ratio of weight average and number average molecular weight ($M_w/M_n$) of from about 1.0 to about 2.0. In one embodiment, $M_w/M_n$ is from about 1.1 to about 1.5. In another embodiment, $M_w/M_n$ is from about 1.2 to about 2.0.

Recognition Elements

As noted above, in the films of the invention, the second layer includes a plurality of recognition elements. The terms "recognition elements" and "target binding partners" are used interchangeably.

The binding affinity of a target molecule toward to the surface results from the target binding partners immobilized on the surface. The target binding partner and the target molecule, each termed a binding pair member, form a binding pair. Each binding pair member is a molecule that specifically binds the other member. In one embodiment, the target binding partner has affinity to a target molecule with $K_d$ less than about $10^{-8}$.

A binding pair member can be any suitable molecule including, without limitation, proteins, peptides, proteins, poly- or oligo-saccharides, glycoproteins, lipids and lipoproteins, and nucleic acids, as well as synthetic organic or inorganic molecules having a defined bioactivity, such as an antibiotic, anti-inflammatory agent, an enzyme substrate, or a cell adhesion mediator (i.e., a small molecule).

Examples of proteins that can be immobilized on the surfaces of the present invention include ligand-binding proteins, lectins, hormones, receptors, and enzymes. Representative proteins include antibodies (monoclonal, polyclonal, chimeric, single-chain or other recombinant forms) and fragments thereof, their protein/peptide antigens, protein-peptide hormones, streptavidin, avidin, protein A, proteins G, growth factors and their respective receptors, DNA-binding proteins, cell membrane receptors, endosomal membrane receptors, nuclear membrane receptors, neuron receptors, visual receptors, and muscle cell receptors. Representative oligonucleotides that can be immobilized on the surfaces of the present invention include DNA (genomic or cDNA), RNA, antisense, ribozymes, and external guide sequences for RNAase P, and can range in size from short oligonucleotide primers up to entire genes.

Other target binding partners that bind specifically to a target compound include poly- or oligosaccharides on glycoproteins that bind to receptors, for example, the carbohydrate on the ligand for the inflammatory mediators P-selectin and E-selectin, and nucleic acid sequences that bind to complementary sequences, such as ribozymes, antisense, external guide sequences for RNAase P, and aptamers.

In one embodiment, the target binding partner is an antibody, and the target molecule is an antigen against the antibody. In this embodiment, the surface of the invention specifically binds to the antigen and resists non-specific protein adsorption. In one embodiment, the target binding partner is a protein capable of promoting cell adhesion, and the target molecule is a cell. In this embodiment, the surface of the invention specifically binds to the cell and resists non-specific protein adsorption and non-specific cell adhesion.

In certain embodiments, the second layer has a recognition element binding level of about 200 to about 1500 $ng/cm^2$.

Film Substrates

A variety of substrate surfaces can be rendered dual-functional using the materials and methods described herein. Representative surfaces that can be rendered dual-functional include metal and metal oxide surfaces, ceramic surfaces, synthetic and natural polymeric surfaces, glass surfaces, fiber glass surface, silicon/silica surfaces, carbon-based material surfaces, protein-based material surfaces, and cell surfaces. Representative natural polymeric surfaces include collagen, fibrins, and other carbohydrate surfaces suitable for the use of tissue engineering. Representative carbon-based material surfaces include carbon fiber, nanotube, and bulky ball surfaces.

Suitable substrates include those substrates useful in medical diagnostic applications such as biosensors, bioprobes, and biomedical devices including in vivo devices; biomaterials and tissue engineering applications, such as membranes for bioprocesses or bioseparation, implantable devices, prosthetics, and tissue scaffolds; and drug delivery applications, such as particles and nanoparticles.

In one embodiment, the present invention provides a SPR sensor comprising a film of the invention.

It will be appreciated that the films of the invention have been described as including (i.e., the film comprises) the stated components. It will be appreciated that in certain embodiments, the films of the invention described above include the stated components as well as other components that do not alter the novel and material characteristics properties of the film (i.e., the film consists essentially of). Components that alter the novel and material characteristics of the film include components that adversely affect the films ultra low fouling or the ability of the film to capture target molecules through its recognition elements. It will also be appreciated that in certain embodiments, the films of the invention described above include only the stated components (i.e., the film consists of).

Methods for Making Films

In another aspect of the invention, methods for making the films of the invention are provided. In one embodiment, the method includes forming a first layer having a first layer density on a substrate; and forming a second layer on the first layer, the second layer having a second density, wherein the first layer density is greater than the second layer density. In certain embodiments, further includes a plurality of recognition elements to the second layer.

As noted above, in certain embodiments, the film is a polymer film in which the first, second, or first and second layers comprise a plurality of polymers. In certain embodiments, the first layer is a nonfouling layer and the second layer is effective to specifically bind target agents. In certain embodiments, the first layer comprises a first polymer layer having a first polymer density, and the first polymer layer comprises a plurality of first polymers, wherein each first polymer is attached to a substrate; and the second layer comprises a second polymer layer having a second polymer density, wherein the second polymer layer comprises a plurality of second polymers, wherein each second polymer is attached to a first polymer.

The first layer can be formed by grafting first polymers from the substrate. Grafting the first polymers from the substrate can be accomplished by any one of a variety polymerization methods (e.g., free radical polymerization, atom transfer radical polymerization (ATRP), reverse addition fragment transfer (RAFT), photoiniferter-mediated polymerization (PIMP), condensation/ring opening polymerization).

Alternatively, the first layer can be formed by grafting first polymers to the substrate. In these methods, the first polymer can be attached to the substrate by any one of a variety of coupling techniques. In one embodiment, the first polymers are covalently coupled to the substrate by click chemistry. In another embodiment, the first polymers are covalently coupled to the substrate by thiol-ene. It will be appreciated that any coupling technique requires suitably reactive second polymers and first layer components.

For embodiments in which the film is a polymer film, the first polymer may be coupled to the substrate surface through alkylene linkers. The grafting of the polymers onto the surface of the substrate through the alkylene linkers may be via any one of a variety of polymerization methods as described herein. SAMs on substrate surfaces are an excellent platform for surface polymerization. In one embodiment, a radical initiator-terminated self-assembly monolayer (SAM) comprising the alkylene linkers can be formed onto the substrate surface, and the polymers are grafted onto the surface through the radical initiator-terminated self-assembly monolayer. In this method, the substrate surface can be coated with the SAMs terminated with radical initiator, wherein the radical initiators are tethered to the surface through alkylene linkers. The alkylene linkers can be any substituted or unsubstituted alkylene. In one embodiment, the alkylene linker is a C2-C30 alkylene. Polymers are then formed onto the SAMs to provide a layer of nonfouling polymeric coating on the substrate surface. Atom transfer radical polymerization is initiated by the radical initiator at the SAMs terminus.

In one embodiment, a hydroxyl-terminated monolayer having alkylene linkers can be formed onto the substrate surface, which is subsequently converted to a radical initiator terminated monolayer.

Materials and methods for making a single layer polycarboxybetaine film having nonfouling properties and the ability to specifically bind target agents is described in US 2010/0099160 (Dual-Functional Nonfouling Surfaces and Materials), expressly incorporated herein by reference in its entirety.

The second layer can be formed by grafting second polymers from the first layer. Grafting the second polymers from the first polymers can also be accomplished by any one of a variety polymerization methods (e.g., free radical polymerization, atom transfer radical polymerization (ATRP), reverse addition fragment transfer (RAFT), photoiniferter-mediated polymerization (PIMP), condensation/ring opening polymerization). A schematic illustration of representative methods for grafting second polymers to the first layer is shown in FIG. 1.

Alternatively, the second layer can be formed by grafting second polymers to the first layer. In these methods, the second polymer can be attached to the first layer by any one of a variety of coupling techniques. In one embodiment, the second polymers are covalently coupled to the first layer by click chemistry. In another embodiment, the second polymers are covalently coupled to the first layer by thiol-ene. It will be appreciated that any coupling technique requires suitably reactive second polymers and first layer components.

It will be appreciated that films with additional layers (e.g., third, fourth, or fifth layers) are within the scope of the invention. The additional layers can be formed on the two-layer film described herein. For example, the third layer can be formed on the second layer (e.g., by "graft from" or "graft to" techniques). Subsequent layers can be similarly formed.

The present invention provides methods for modifying the second layer to provide a surface having affinity toward a target molecule. In one embodiment, the method for modifying a surface, includes covalently coupling a plurality of target binding partners (i.e., recognition elements) to the second layer. In certain embodiments, an amide linkage is formed between the polymers and the target binding partners. For polymer films that include carboxylic acid groups (e.g., polycarboxybetaines), covalently coupling the plurality of target binding partners to the plurality of polymers includes converting a portion of carboxylic acid groups to activated esters and reacting the activated esters with target binding partners having amino groups. For polymers that have been modified to include available amino groups, covalently coupling the plurality of target binding partners to the plurality of polymers includes converting a portion of carboxylic acid groups of the target binding partners to activated esters and reacting the activated esters with the polymers of the surface having available amino groups. In one embodiment, the activated esters are N-hydroxysuccinimide esters. Suitable target binding partners include those described in detail above with regard to the films of the invention.

As noted above, the carboxylic acid groups of the polymers may be activated by forming activated intermediate groups for further coupling with the amino groups of the biomolecule. Any activated form of carboxylic acid groups may be used in the present invention. The representative activated intermediate groups include carbodiimides, carbonyldiimidazoles, uranium salts, isothiocyanates, isocyanates, acyl azides, N-succinimidyl esters (NHS esters), sulfonyl chloride, aldehydes, epoxides arylating groups, imido esters, and anhydrides. In one embodiment, O—(N-succinimidyl)-N,N,N',N'-tetramethyluronium tetrafluoroborate (TSTU) is used to convert the carboxylic acid groups on the polymers to activated uronium salts. In another embodiment, carbodiimides and N-hydroxysuccinimide (EDC/NHS coupling chemistry) are used to convert the carboxylic acid groups on the polymers to activated N-hydroxysuccinimide esters.

In one embodiment, the carboxylic acid groups were converted to activated NHS esters by treating the carboxylic acid groups with N-bromo succinimide (NHS) and N-ethyl-N'-(3-diethylaminopropyl) carbodiimide (EDC) under acidic conditions (e.g., pH 2.5 to 6). The activated NHS esters were coupled with the amino groups of the target binding partner forming amide bonds under basic conditions (e.g., pH 7.4 to 11).

The preparation of representative films of the invention is described in Examples 1-3.

Methods for measuring refractive index and swelling ratio for representative films of the invention are described in Examples 4 and 5, respectively.

Methods for Detecting the Presence of an Analyte Using the Film of the Invention In another aspect, the invention provides methods for determining the presence of an analyte in a sample. The method utilizes film of the invention comprising a plurality of recognition elements. In one embodiment, the method includes contacting a sample with a film of the invention comprising a plurality of recognition elements, wherein each recognition element has a specific binding affinity for the analyte; and interrogating the film to determine whether the analyte has bound to the film. The film can include one or more different recognition elements for the detection of one or more analytes. The film can be interrogated by any method that provides an indication of analyte binding to the film.

Representative films and methods for making and using the films are described below.

Representative Polymer Films

In one aspect, the invention provides a polymer film having two layers (i.e., a hierarchical architecture) prepared from two distinct surface-initiated techniques. These "graft from" techniques are based on controlled "living" radical polymerizations and provide polymer brushes having controlled chemical composition, film thickness, and architecture. As shown in FIG. 1, one film was prepared via surface initiated atom transfer radical polymerization (SI-ATRP) and the other film was prepared via surface initiated photoiniferter-mediated polymerization (SI-PIMP). In each film, the first layer was grown in a controlled manner to reach a high surface packing density. The second layer, with a lower surface packing density, was achieved through "termination" or "regeneration" of the living capped species at the polymer chain end for SI-ATRP and SI-PIMP, respectively.

Due to the dual functionality of poly(carboxybetaine) (pCB) films, a surface plasmon resonance (SPR) biosensor with a pCB film was used for demonstrating the novel hierarchical architecture. Surface-tethered pCB brushes formed by both SI-ATRP and SI-PIMP achieve excellent resistance to nonspecific protein adsorption in the presence of complex media, such undiluted human blood serum and plasma, to fouling levels below 5 ng cm$^{-2}$. These fouling levels can be maintained following the immobilization of around 250 ng cm$^{-2}$ of antibody using conventional 1-ethyl-3-(3-dimethylaminopropyl)-carbodiimide and N-hydroxysuccinimide (EDC/NHS) coupling chemistry under biologically friendly conditions. However, this functionalization level only corresponds to an IgG monolayer. The pCB-based polymer films (platforms) of the invention with hierarchical structures on a SPR sensor surface provide sensitive quantification of IgG immobilization, antigen binding, and non-specific protein adsorption.

As shown in FIG. 1, ATRP was combined with a "termination" approach for demonstrating the novel architecture. ATRP involves a dynamic equilibrium between activated propagating radicals and dormant halide end-capped polymer chains, yielding low polydispersity and controlled growth. This "living" characteristic enables re-initiation from macroinitiators for the synthesis of block copolymers.

To achieve hierarchical pCB films possessing ultra low fouling and high loading properties via SI-ATRP, a densely-packed first layer was grown from a gold coated SRP chip modified with an alkyl bromide terminated self-assembled monolayer (SAM). The chips were then submerged in a methanolic solution containing 2,2'-bipyridine, CuBr, and CB monomer under nitrogen protection and allowed to react overnight. The resulting thickness was 7.6±0.3 nm (Table 1). Importantly, these conditions enabled a highly dense yet thin film to be grown. While the high density is key for achieving low fouling, a thin film is desired for many sensing applications, such as SPR, as the signal intensity/sensitivity decays exponentially from surface of the metal substrate. To establish a hierarchically structured pCB film for increasing the binding capacity, the macroinitiator density for re-growth of the second pCB layer was regulated via azide substitution of bromide species thus "terminating" the future growth of the corresponding chains during the second ATRP reaction. The density of the polymer chains can be controlled by the azide concentration and reaction time. A 2 hr submersion using an azide concentration of 0.1 M produced an optimal second layer polymer density for protein immobilization. For the growth of the second pCB layer, water-accelerated polymerization with a solvent consisting of 50% water in methanol was employed to induce a high polydispersity of polymer chains. The resulting thickness of the structured film with azide substitution was higher than that without treatment. This is in agreement with previous reports showing rapid bimolecular termination at high initiator densities using aqueous ATRP whereas more dilute initiators enabled continued linear and controlled polymer growth.

In contrast to SI-ATRP, SI-PIMP releases capped species from the polymer chains during polymerization, primarily due to bimolecular termination. This irreversible termination significantly hampers future polymer growth. Therefore, in order to control the chain density of the second layer via SI-PIMP, a "regeneration" approach was adopted in which the addition of a deactivator, tetraethylthiuram disulfide (TED), was able to preserve the end-capped photoiniferter groups on the grafted polymers for re-growth of the second layer with controlled grafting density. SPR gold substrates were first modified with the photoiniferter (N,N-(diethylamino)-dithiocarbamoylbenzyl(trimethyoxy)-thiol (DTCA)) to form SAMs. Similarly to SI-ATRP, the first layer for SI-PIMP was also synthesized in 100% methanol to form a highly dense and thin film. Reactions were conducted using a 30 min UV irradiation and the resulting film thicknesses are shown in Table 1. The first layer thicknesses prepared with 2 µM TED was comparable to that without TED (11.1±0.6 nm). Subsequently, the films were re-initiated in a 90% water/methanol solution resulting in TED treated films with greater thicknesses than those made without, reflecting the ability of TED for preserving the reactive photoiniferter end groups and thereby maintaining the "living" characteristic of SI-PIMP.

The thicknesses of representative films prepared via SI-ATRP and SI-PIMP with and without treatment to capped species are compared in Table 1.

TABLE 1

Film thickness with and without treatment to capped species.

|  | SI-ATRP Thickness (nm) | SI-PIMP Thickness (nm) |
|---|---|---|
| First Layer | 7.6 ± 0.3 | 10.8 ± 0.8 |
| Re-growth (without treatment) | 13.2 ± 0.3 | 32.1 ± 0.6 |
| Re-growth (with treatment) | 17.5 ± 0.9 | 46.1 ± 1.6 |

Figure 2A:
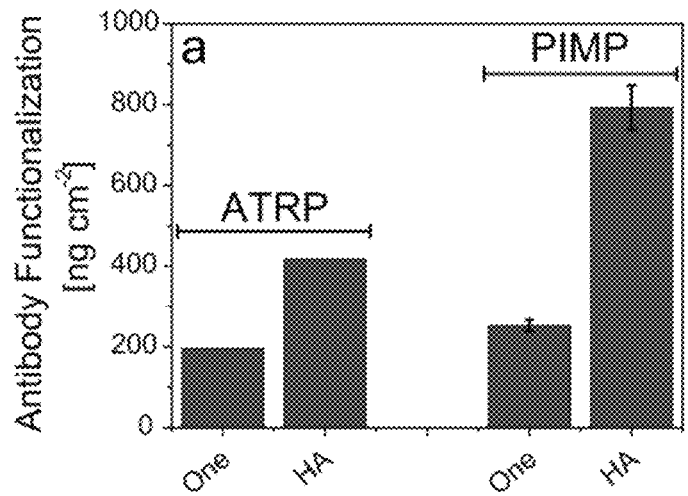
FIGS. 2A-2C compare IgG functionalization levels (2A), fouling levels in the presence of undiluted serum or plasma, before and after IgG functionalization (2B), and antigen detection (2C) on films with one-layer (One) and hierarchical (HA) structures prepared via SI-ATRP and SI-PIMP.
Figure 3:
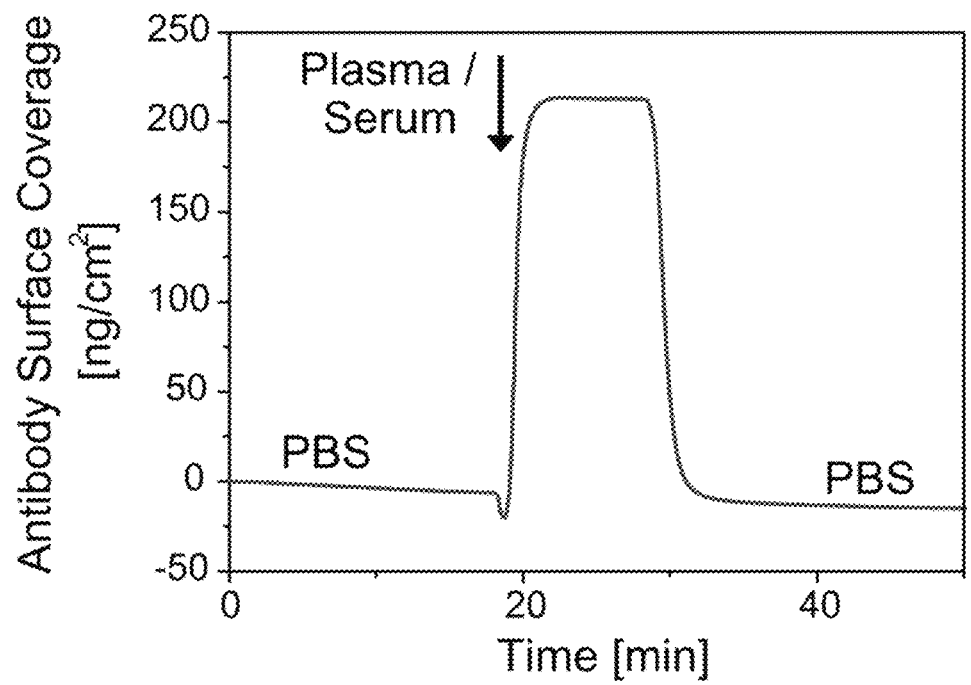
FIG. 3 is an SPR sensorgram for a fouling test in the presence of undiluted blood plasma or serum on a representative hierarchical pCB film of the invention.
Figure 4:
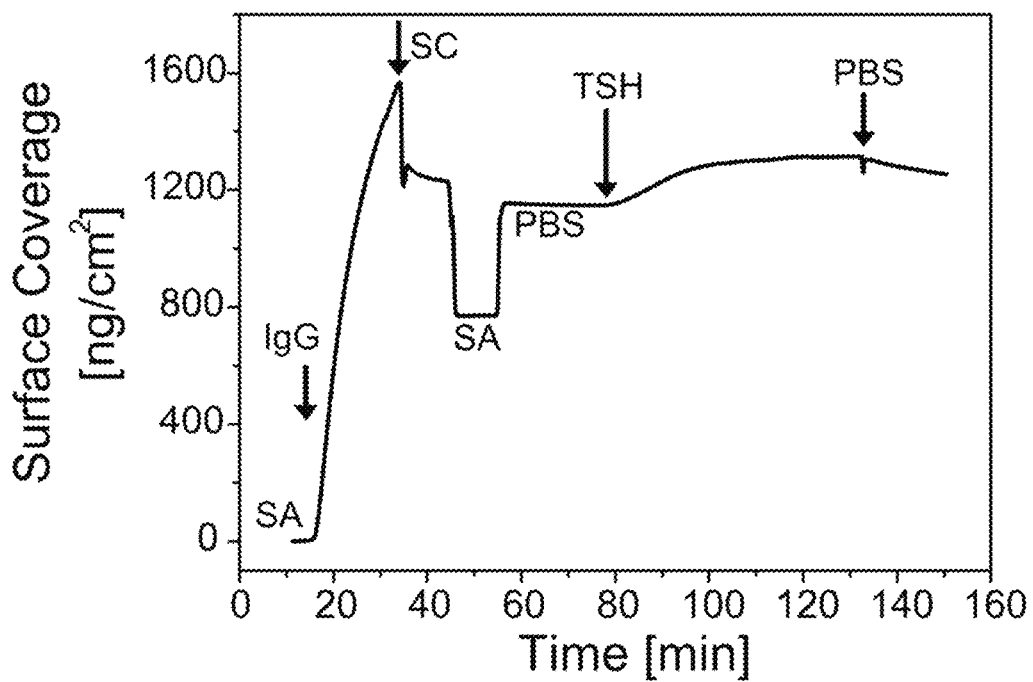
FIG. 4 is an SPR sensorgram for a fouling test on a representative hierarchical pCB film of the invention following modification with TSH IgG, deactivation with SC buffer, and then used for TSH antigen detection.

Functionalization and fouling tests were monitored in situ using a custom-built SPR sensor with wavelength modulation (see representative sensorgrams in FIGS. 3 and 4). For antibody immobilization, the films were activated using EDC/NHS coupling chemistry followed by injecting an anti-human thyroid stimulating hormone (anti-TSH) IgG solution. The unreacted NHS esters were then hydrolyzed back into the original carboxylate groups using 10 mM sodium carbonate buffer with 300 mM NaCl at pH 10. As shown in FIG. 2A, the functionalization levels were estimated as 195.9 ng cm$^{-2}$ and 417.0 ng cm$^{-2}$ for one-layer ("One") and hierarchical ("HA") films prepared via SI-ATRP; 253.0±14.8 and 792.7±54.7 ng cm$^{-2}$ for one-layer and hierarchical films from SI-PIMP. An increase in binding capacities for IgG molecules on pCB films was observed for the hierarchical architecture. For the IgG functionalized one-layer films, the binding capacities were similar to that obtained with carboxyl-terminated SAMs. Although pCB provides abundant carboxyl groups for biomolecule conjugation, highly-packed polymer brushes hamper the penetration of molecules due to steric hindrance and therefore modification only takes place at the accessible functional groups on the topmost layer of the pCB films. However, for the hierarchical films, the chain densities of the second layer were controlled via the termination and regeneration approaches. Constructed from highly dense first layers, the loose second layers allowed diffusion of antibodies thus enabling conjugation with NHS esters throughout the entire second layer. The control experiments using the structured films without treatment of capped species were also conducted. IgG immobilization levels were reduced by 30% and 64% for SI-ATRP and SI-PIMP, respectively, compared to the corresponding treated hierarchical pCB films. This evidence indicates that a sufficient number of accessible binding groups for protein modification, made apparent by the larger second-layer film thicknesses of the treated films, are a determining factor of the ligand loading capacity.

Figure 2B:
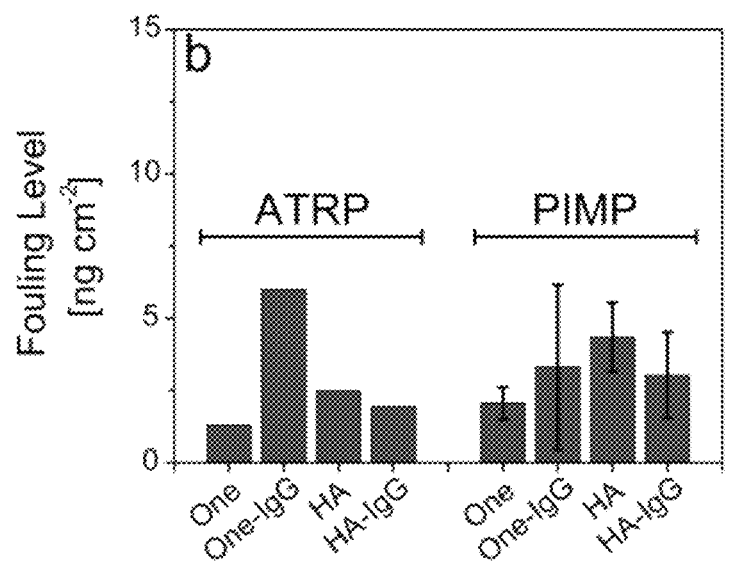

The protein fouling levels on one-layer films and hierarchical pCB films before and after IgG functionalization were tested by flowing undiluted blood serum or plasma (FIG. 2B). All fouling levels were very low as a result of the highly-packed first pCB layers serving as ultra low fouling backgrounds. As a comparison, the fouling level for a loose pCB one-layer film with a thickness of 12.3 nm prepared from 50% water in methanol by SI-PIMP was as high as 54.3 ng cm$^{-2}$ in the presence of serum. These results indicate that the high performance of pCB for effective resistance against non-specific adsorption and high ligand loading is established on the basis of control over the polymer architecture.

Figure 2C:
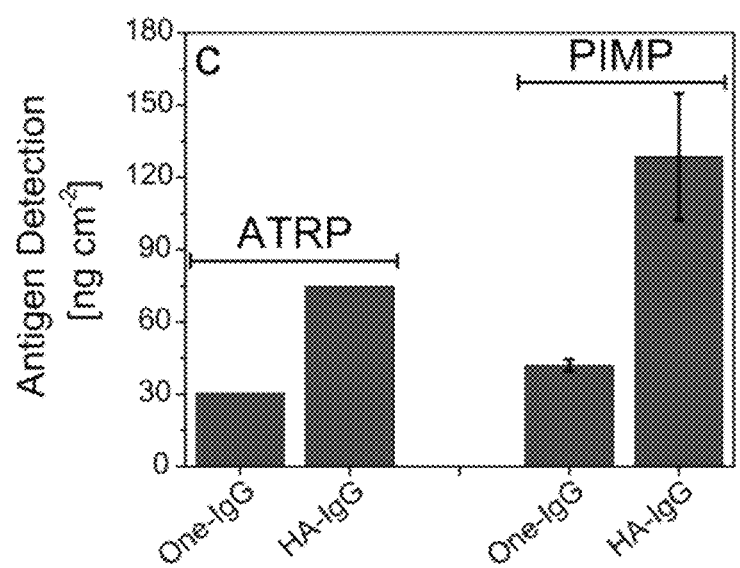

Solutions containing TSH antigen were flowed over the functionalized surfaces to evaluate the antigen detection ability (FIG. 2C) and the bio-activities (molar ratios of antigen to antibody) of the binding platforms. TSH binding capacities were 42.1±2.4 ng cm$^{-2}$ and 128.5±26.2 ng cm$^{-2}$ for one-layer and hierarchical pCB films from SI-PIMP, respectively. The corresponding bio-activities were 0.89 and 0.87. The one-layer and hierarchical pCB films made via SI-ATRP bound 30.4 ng cm$^{-2}$ and 74.7 ng cm$^{-2}$ of TSH, respectively, with bio-activities of 0.80 and 0.93, respectively. Thus, the binding capacity for antigens is well correlated to the degree of antibody immobilization and that the bio-activity of the film is not affected by the pCB hierarchical architecture.

SI-PIMP Methods

In one embodiment, the invention provides a polymer film having two layers (i.e., a high density ultra low fouling first layer and a low density second layer suitable for presenting recognition elements) prepared via surface initiated photoiniferter-mediated polymerization (SI-PIMP) techniques.

Zwitterionic polycarboxybetaine acrylamine (pCB)-based platforms with a two-layer structure for ultra low fouling and high protein loading properties were prepared. The first pCB layer with a high packing density prepared under a water-free condition serves as a protective layer to resist nonspecific adsorption from complex media. The second pCB layer with a low packing density is used to achieve high protein immobilization. Addition of tetraethylthiuram disulfide (TED) and the water content in the reaction were varied to regulate polymer chain density and length, respectively, for the second pCB layer. The in situ modification of pCB films with anti-human thyroid stimulating hormone (TSH) IgG molecules and the detection of TSH antigens were employed to demonstrate high protein immobilization and high antigen detection capabilities of this two-layer structure. Undiluted blood plasma was used to test the nonfouling properties of this system. Nonspecific and specific interactions were monitored by a surface plasmon resonance sensor.

In one embodiment, the two-layer structured pCB film was prepared by (i) growing a densely-packed first pCB brush under a water-free polymerization condition, (ii) adjusting the surface density of the "living" capping moieties on the first pCB layer by adding the TED molecules, and (iii) promoting the chain growth of the second pCB layer via water-accelerated polymerization. The growth of polymer brushes was monitored using ellipsometer. The protein loading on the structured pCB films was investigated by conjugating anti-human thyroid stimulating hormone (TSH) antibodies through EDC/NHS coupling chemistry, followed by flowing the TSH antigens for estimating the bioactivities. The non-fouling properties of the platforms before and after antibody functionalization were realized by challenging with undiluted human blood plasma.

Figure 5A:
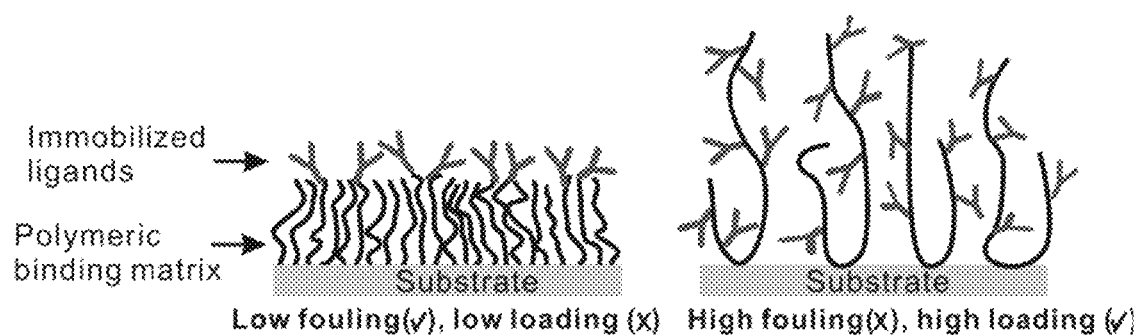
FIGS. 5A and 5B are schematic illustrations of conventional platforms.

Although this pCB platform has shown great success to resist nonspecific protein adsorption from complex media, relatively low antibody loading, similar to all 2-dimensional (2D) surface platforms, limits the sensor response to analyte binding. Owing to the high packing density of the brush film, such surfaces can merely achieve an antibody binding capacity of only 250 ng cm$^{-2}$ (corresponding to an IgG monolayer) (FIG. 5A, left panel). A three-dimensional (3D) carboxymethylated dextran-based SPR chip fabricated via a "graft-to" approach has a high protein binding capacity of more than 1000 ng cm$^{-2}$. However, this high loading accompanies high nonspecific protein adsorption on unprotected substrate surfaces during detection primarily due to the "loose" polymeric structure (FIG. 5B, right panel).

Figure 5B:
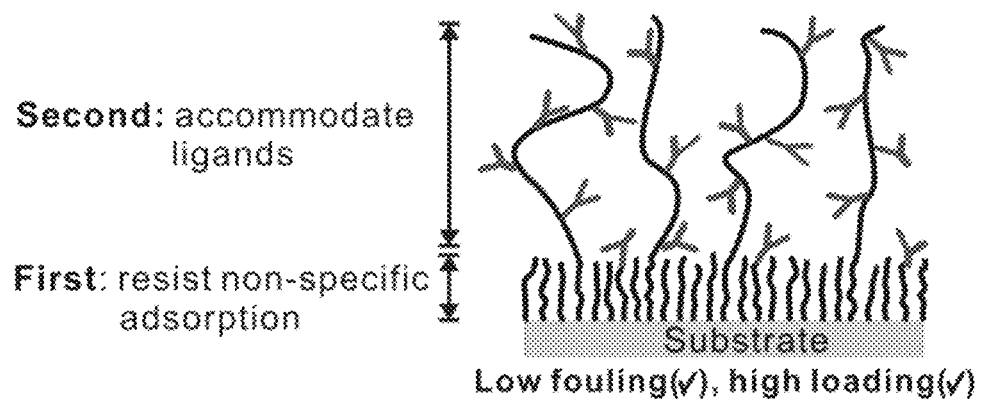

In one embodiment, the present invention provides a two-layer structured binding platform that incorporates a first highly dense pCB layer to achieve ultra-low fouling and a second "loose" pCB layer to achieve a high antibody binding capacity (FIG. 5B).

Figure 6:
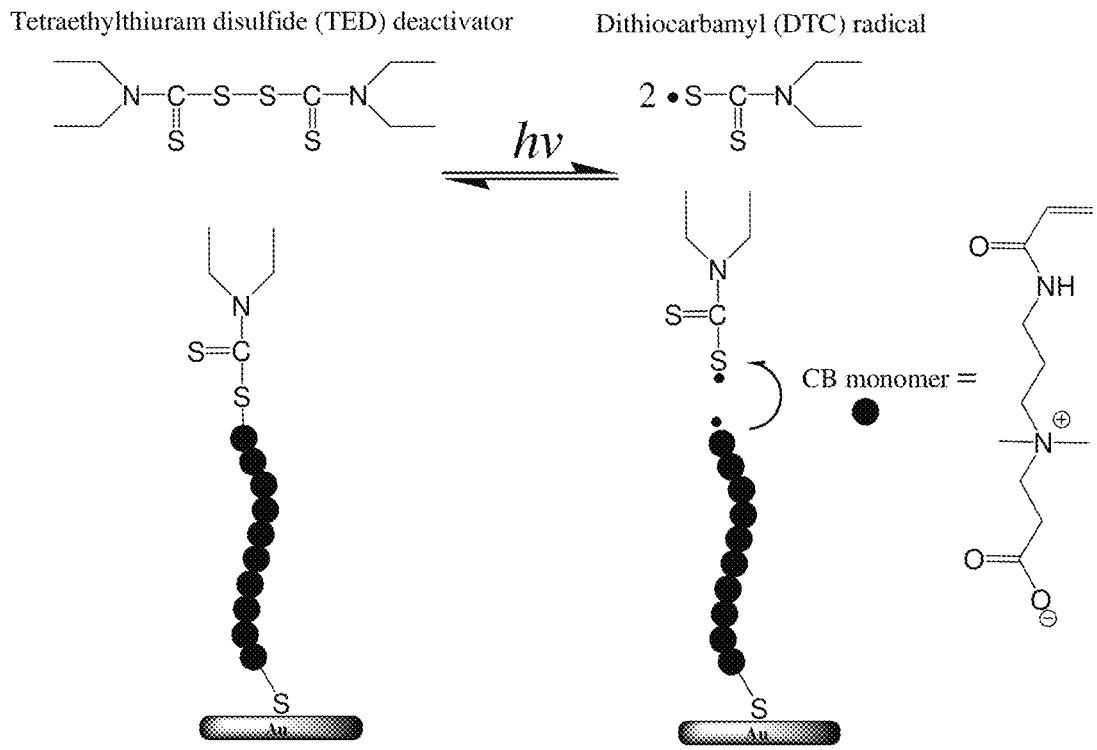
FIG. 6 is a schematic illustration of a photoiniferter-mediated polymerization of surface-tethered pCB brushes in the presence of TED deactivator.

Surface-initiated photoiniferter-mediated polymerization can be used for preparing surface-tethered pCB films. This polymerization technique poses advantages of simple experimental process, fast reaction rate, and large-scaled surface polymerization, which make an attractive approach for tailoring surface properties. In addition, this technique enables to control light exposure spatially and temporally for creating multidimensional structures regardless of types of monomers. The pCB chains were grown from a self-assembled monolayer comprising of thiolated photoiniferter (N,N-(diethylamino)-dithiocarbamoylbenzyl(trimethyoxy) thiol (DTCA)). The photoiniferters provide control over the reaction by maintaining equilibrium between activated propagating chains and dormant chains that are capped by deactivating species, resulting in controlled radical polymerization. However, due to a low concentration of the deactivating radicals, the polymerization favors irreversible termination caused by bimolecular termination. To preserve the "living" capability of the pCB films, the reduction of termination can be accomplished by adding deactivating species, tetraethylthiuram disulfide (TED), to the reaction medium (FIG. 6). While irradiated with UV light, TED undergoes a homolytic cleavage, generating two dithiocarbamyl (DTC) radicals. As the concentration of the deactivating species increases, the capability of re-initiation is enhanced. Representative films of the invention (two-layer pCB films) were prepared by: (i) growing a densely-packed first pCB brush under a water-free polymerization condition; (ii) adjusting the surface density of the "living" capping moieties on the first pCB layer by adding the TED molecules, and (iii) promoting the chain growth of the second pCB layer via water-accelerated polymerization.

Figure 7A:
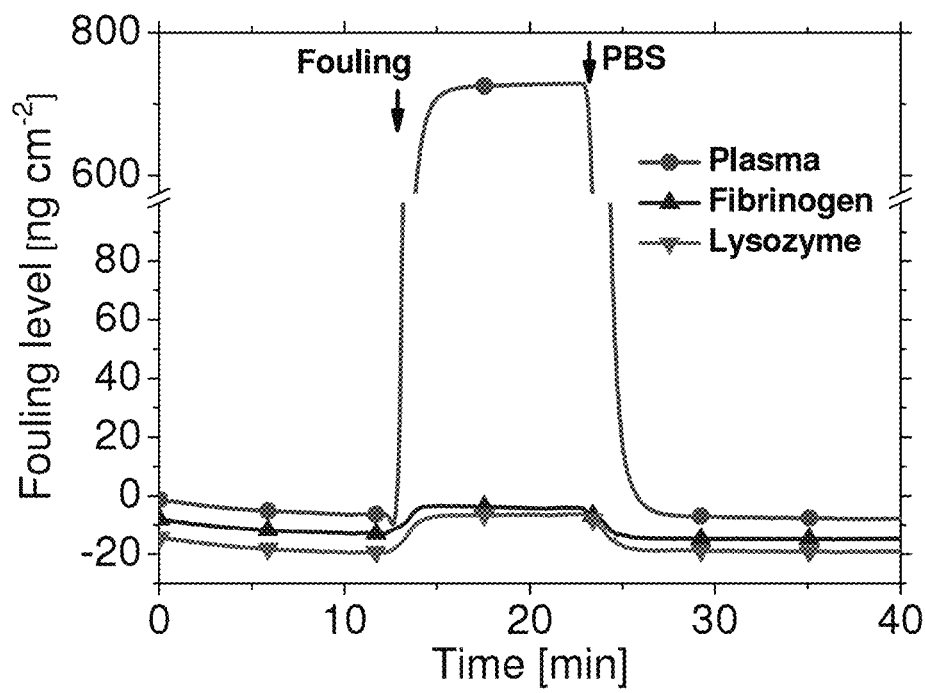
FIG. 7A compares SPR sensorgrams for fouling tests on pCB films prepared from 100% MeOH without TED addition in contact with undiluted plasma (●), fibrinogen (▲), lysozyme (▼).

The densely-packed first pCB layer was fabricated via photoiniferter-mediated polymerization in 100% methanol. After 30 min UV exposure, the resulting thickness of the pCB was d1st=10.9±0.7 nm. In FIG. 7A, the fouling tests with undiluted plasma, 1 mg mL$^{-1}$ fibrinogen and lysozyme dissolved in PBS for the first pCB film were monitored on SPR. After the buffer washing the fouling level was indicated as 3.9±0.8 nm for plasma and for fibrinogen and lysozyme, their fouling levels were both below the detection limit of the SPR sensor which is 0.3 ng cm$^{-2}$. 21 Therefore, the first pCB layer was developed and ensured its efficient protection of the surface from protein adsorption.

Figure 7B:
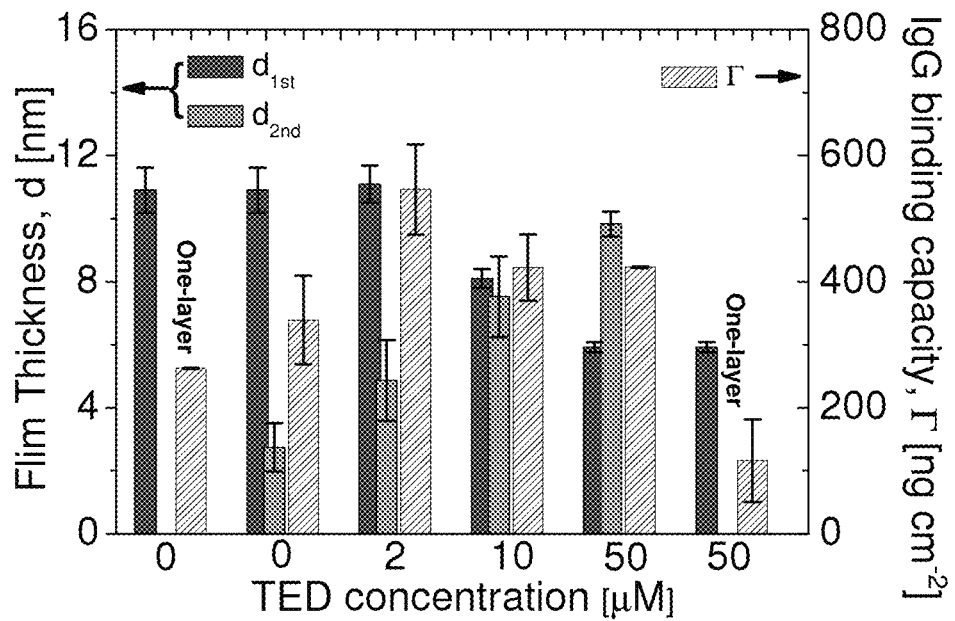
FIG. 7B compares film thickness and IgG binding capacity of pCB films as a function of the TED concentration. The dry film thicknesses were measured using ellipsometer. IgG molecules were chemically conjugated on binding platforms with one- and two-layer pCB structures and their binding capacities were estimated using SPR.

In order to re-initiate the second layer of pCB, TED was added to regenerate the initiator during the polymerization for the growth of the first pCB layer in order to prevent the irreversible termination. The concentration of TED was varied from 0 to 50 μM. The growth of the second layers was accomplished with the CB monomer concentration of 0.15 M in the mixed solvent of MeOH:H$_2$O=50:50 for 30 min. In FIG. 7B, the dry thickness of the first pCB layer deceased with the increased TED concentration. However, the thickness of the second pCB layer increased from d2nd=2.7±0.8 nm to 9.8±0.4 nm. This indicates that the presence of TED in the polymerization shifts the equilibrium of the surface-tethered radicals toward the dormant state as shown by decreased thicknesses in the first pCB layers with the TED concentration. As a result, the TED addition slowed the monomer conversion rate and to inhibit generation of radicals. At the same time, the re-growth of the second pCB layer was promoted due to the high surface concentration of iniferter species.

The IgG modification was conducted through EDC/NHS coupling chemistry and the corresponding binding capacities of surfaces were measured using a SPR sensor. FIG. 7B shows that the maximum binding capacity occurred on the two-layer pCB film prepared from the TED concentration of 2 μM, which was Γ=546.2±71.4 ng cm$^{-2}$. The one-layer pCB films prepared from the TED concentrations of 0 and 50 μM, the binding capacities for IgG molecules were significantly lower than any two-layer structured films. For instance, on the one-layer film prepared from 50 μM TED, the binding capacity was merely Γ=116.0±65.6 ng cm$^{-2}$. The results indicate that for the one-layer films and the two-layer films prepared from high TED concentration, it was difficult for IgG molecules to penetrate through the brushes owing to the steric hindrance and most likely conjugated on the outmost of pCB films.

Figure 8A:
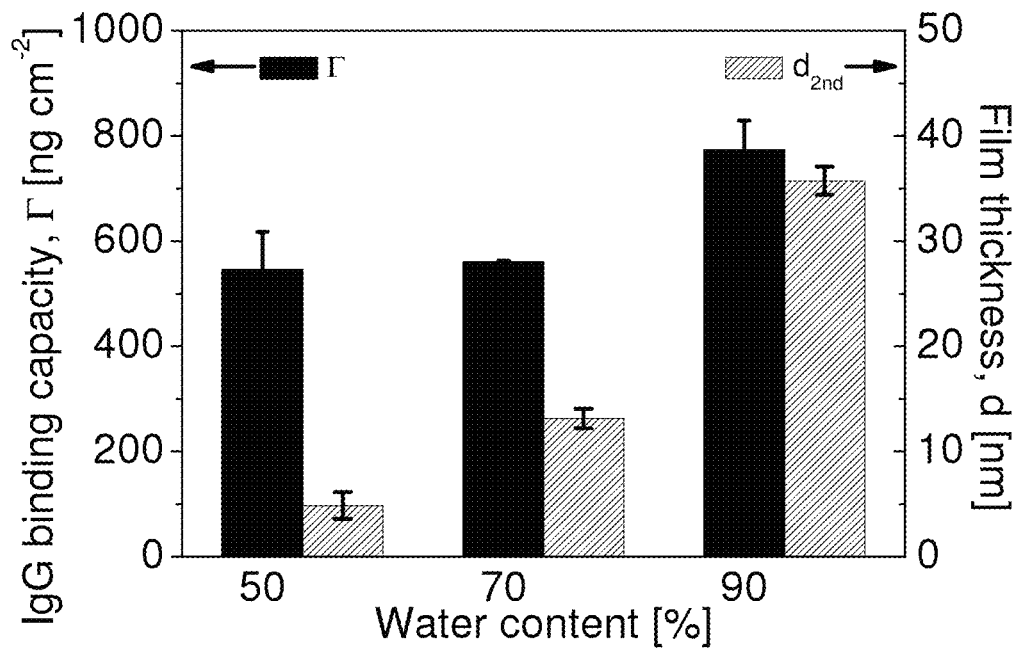
FIG. 8A compares IgG binding capacity and dry thickness of the second layer as a function of the water content in the polymerization for the second layer.
Figure 8B:
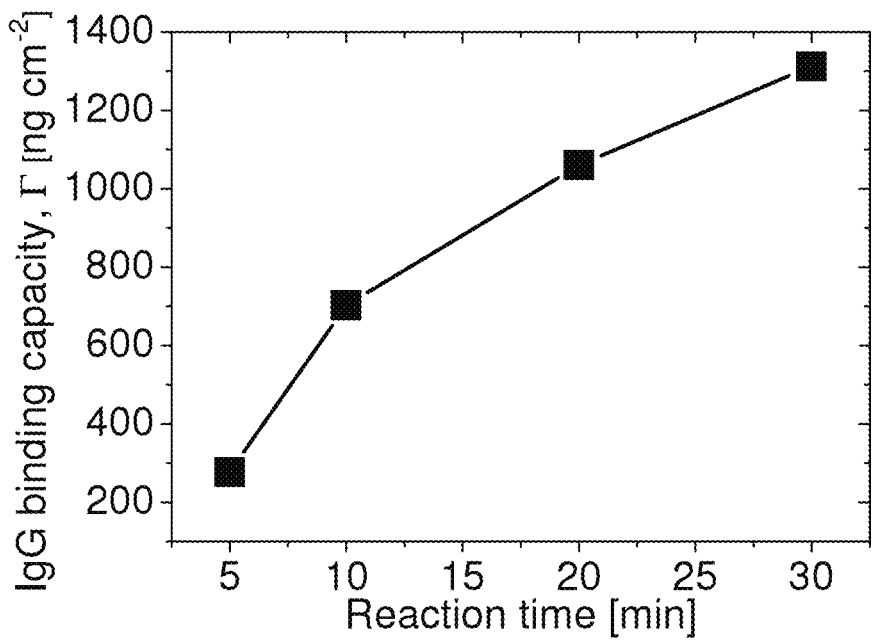
FIG. 8B compares IgG binding capacity versus EDC/NHS activation time.

To further increase the binding capacity, "water-accelerated" polymerization was used to increase the chain length of the second layer for providing large available binding sites for IgG conjugation. As seen in FIG. 8A, after the re-initiation from the first layer prepared from 100% methanol containing 2 μM of TED, the thicknesses of the second layers were measured and found to increase with the water content relative to MeOH in the reaction solvent. The surfaces were subsequently reacted with EDC/NHS mixture for 7 min followed by flowing anti-TSH IgG solution for 20 min. The results show that the binding capacities were dependent on the thicknesses of the second layers (FIG. 8A). Moreover, the degree of conversion from carboxyl groups to NHS esters in pCB brushes was mediated by the EDC/NHS reaction time (FIG. 8B). The binding capacity for IgG on the two-layer structured pCB film increased to 1312.2 ng cm$^{-2}$ after 30 min activation, which is more than five times more than that on the one-layer pCB film.

AFM in the tapping mode was used to examine the surface morphology of the two-layer pCB films before and after IgG functionalization. The image of the pristine pCB film with a scale of 1 μm×1 μm showed featureless morphology, whereas there were enormous bumps observed on the IgG functionalized pCB, as an evidence of the high density of immobilized IgG molecules. Therefore, this approach to build up a hierarchical structure of pCB film enables the accommodation for a large amount of biomolecules through conventional EDC/NHS amine coupling chemistry and possesses possibility to manipulate the chain density of the second pCB layer for customizing specific requirements, such as considerations on ligand and antigen sizes.

Figure 9A:
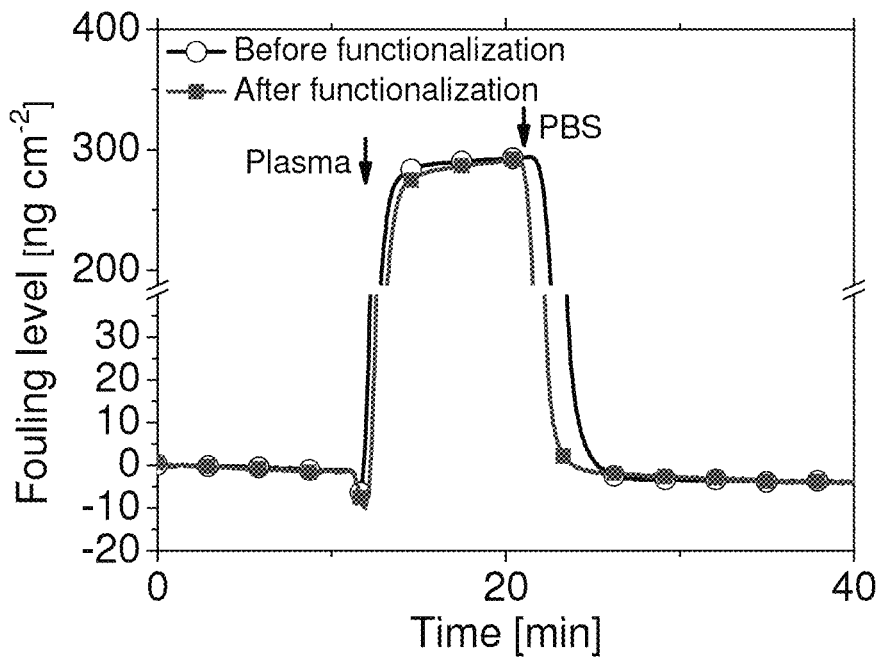
FIG. 9A compares SPR sensorgrams for fouling tests with undiluted blood plasma on the two-layer structured pCB films with and without IgG functionalization.
Figure 9B:
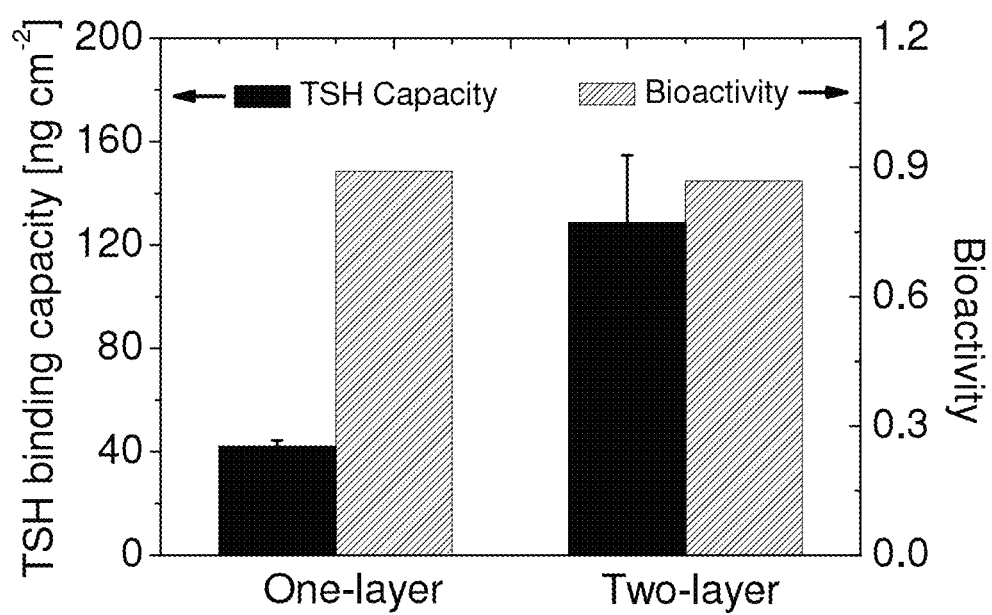
FIG. 9B compares TSH binding capacity and surface bioactivity on pCB films with one-layer and two-layer structures.

For biosensor applications, an appropriate design of biointerfaces should be capable of improving the sensitivity and specificity of detection. In the following description, the film with "one-layer" structure is referred to the one fabricated in 100% MeOH without TED addition (d1st=10.9±0.7 nm; Γ=262.5±0.8 ng cm$^{-2}$, FIG. 7B). For the "two-layer" binding platform, the first layer was prepared from 100% MeOH with 2 μM TED and the second layer was re-grown in the solvent with a volume ratio of MeOH:H$_2$O=10:90 with 30 min UV radiation (d1st=11.1±0.6 nm; d2nd=35.7±1.3 nm; Γ=773.2±55.9 ng cm$^{-2}$, FIG. 8A). Functionalization of TSH IgG on both one-layer and two-layer binding platforms was conducted via EDC/NHS activation for 7 min and allowing the 20 min reaction with IgG molecules. To verify to the performance of the constructed "two-layer" pCB binding platform for biosensing in complex media, the undiluted plasma was flowed over surfaces with and without the IgG functionalization for 10 min and then rinsed with PBS to remove unbound molecules. As shown in FIG. 9A, the fouling levels were both below 5 ng cm$^{-2}$. Again, the fouling resistance of the "two-layer" binding platform can be attributed to the excellent nonfouling capability of the densely packed first pCB layer. The binding capacities of the two-layer pCB films was evaluated for TSH antigens dissolved in PBS at a concentration of 1 μg mL$^{-1}$ and the bioactivity of conjugated IgG molecules, which is defined as the mole ratio of captured TSH antigens to immobilized IgG molecules. The binding platform with "one-layer" structure was present in parallel for a comparison. In FIG. 9B, the TSH binding capacity on "two-layer" pCB films was increased by 3.1 with respect to that on "one-layer" film. The bioactivities on one-layer and two-layer films were quite comparable. This observation reflects the fact that the high surface density of the bound IgG molecules in pCB brushes did not significantly hamper the approach of antigens, which is consistent with works using 3D carboxymethylated dextran-based binding matrix.

SI-ATRP Methods

In another embodiment, the invention provides a polymer film having two layers (i.e., a high density ultra low fouling first layer and a low density second layer suitable for presenting recognition elements) prepared via surface initiated atom transfer radical polymerization (SI-ATRP) techniques.

The two-layer architecture for films of the invention for sensing and detection in complex media is shown in FIG. 10. SI-ATRP was used due to its ability to provide excellent control over polymer growth. Additionally, the "living" characteristic enabled by the reversible equilibrium between active and dormant species allows the formation of block copolymers due to the presence of initiating species, which cap the chain ends once the polymerization is stopped. The use of solvent conditions, which provide high density polymer brushes with minimal chain-chain termination and quenching (spiking the reaction solution with a high concentration of deactivator (e.g. $CuBr_2$), provides the maximum number of re-initiating sites near the outermost surface of the swollen layer, which is highly desired for obtaining sufficient control over the polymer density of the second block.

As shown in FIG. 10, the concentration of re-initiating groups (i.e., bromines) on the surface can be reduced by reacting with an aqueous sodium azide solution. This termination forms a stable azide group, which remains dormant and non-reactive as the second polymerization takes place. Both the concentration and reaction time of sodium azide will affect the degree of termination resulting in surfaces, which are low, moderately, or highly substituted with azide moieties. If the substitution is low then the most chains will just re-initiate and maintain the relative high density resulting in only monolayer antibody coverage. For the chains to grow vertically they need to be close enough together, if they are too dilute, then the chains will preferentially grow laterally in a mushroom configuration. In this highly substituted and very dilute case, the second layer is thin, consisting of a small number of long chains with minimal surface area for antibody immobilization, which also results in low loading. Therefore, in order to achieve high antibody binding capacity, a moderate amount of substitution is desired. In this scenario, the chains will be close enough to be obliged to grow vertically, but dilute enough so as to maximize the surface area for achieving high protein functionalization and enable sufficient diffusion to reactive NHS-esters. It is also important to note that a second layer with moderate substitution can actually grow longer than single layer with low substitution. This is due to a reduction in radical recombination in the former as a result of more space between the growing polymer chains.

Thin (about 10 nm) and highly dense pCB films can be made via SI-ATRP from pure methanol as the solvent can maintain ultra low fouling properties to undiluted serum. The ability to minimize the final thickness of the two-layer film in a swollen in situ environment is crucial for SPR detection. This is due to a rapid decrease in sensitivity as the measured biomolecular interaction gets further from the SPR active gold layer. For this reason, pure methanol was chosen as the condition for the bottom layer. Different reaction times (0.5-24 hrs) were investigated for growing the second block, which used a 50/50 methanol/water solvent. It was found that a 24 hour reaction resulted in the thickest second layer, the highest antibody immobilization, and excellent functionalized and non-functionalized protein resistance to undiluted serum. The response to antigen was similar for all reactions greater than 1 hour, with bioactivity ratios (i.e., the molar ratio of antigen to antibody) all being about 1.0. The 24 hours reaction enabled the same level of antibody immobilization achieved from a single layer grown from a 50% methanol solution. However, the post-functionalized serum non-fouling of the two-layer film ($<5$ ng/cm$^2$) was better than the single layer film (about 15 ng/cm$^2$) proving the effectiveness of the two-layer architecture. A first layer made using 50% water was also prepared. However, this condition was very difficult to control, even with short reaction times on the order of a few minutes, resulting in the final second layer polymer structure being mostly determined by the rapid polymerization of the bottom layer. Furthermore, simply spiking solutions grown from a first layer of either 50% water or in pure methanol with a high concentration of monomer dissolved in pure water was also not found to be effective.

Figure 11:
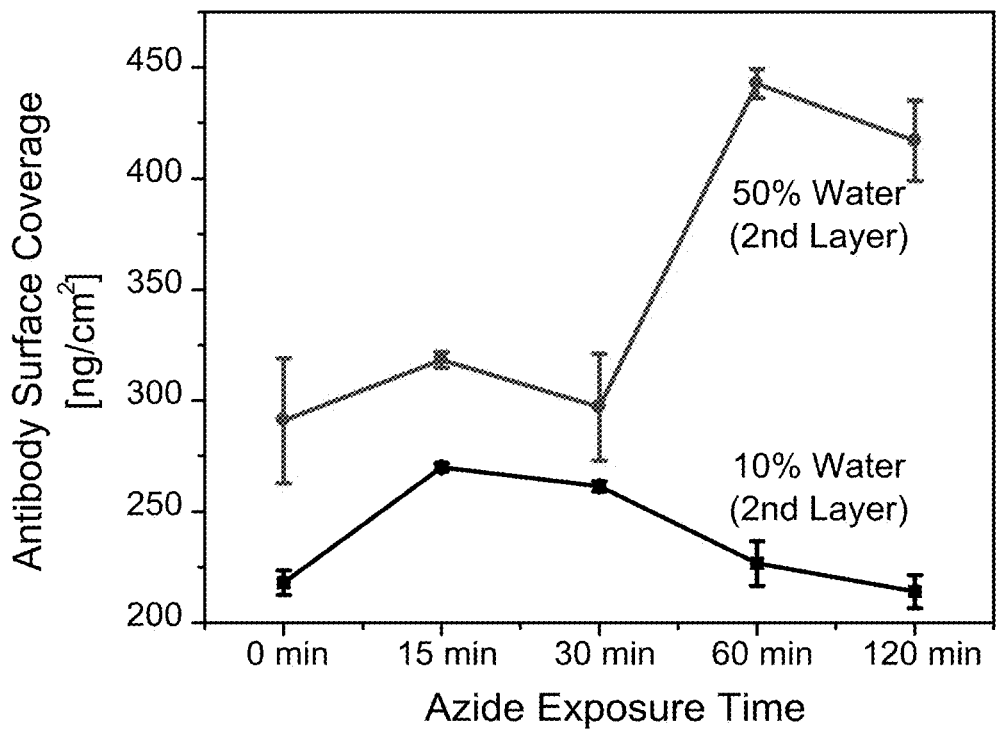
FIG. 11 compares antibody immobilization versus azide exposure time for second layer pCB films grown from 10% and 50% water content.

The affect of azide treatment on the second layer polymer thickness and corresponding antibody immobilization for two different solvent conditions is shown in Table 2 and FIG. 11, respectively. Due to the significant influence of water content on the polymer density of SI-ATRP films, two conditions were used for evaluation of azide exposure time. A 10% and 50% water content was chosen for slower (more controlled) and faster (less controlled but more polydisperse) polymerizations, respectively. Both conditions resulted in the expected trends as discussed above for FIG. 10. Reducing the concentration of re-initiating species lead to an increase in the film thickness which then decreased as the chains became more and more dilute. It was observed that as the second layer thickness increased, the antibody immobilization also increased. This indicates that the moderately diluted second layer has more surface area (i.e. more accessible NHS-esters) for protein attachment. However, as the chains become more dilute, the available surface area decreases along with the immobilization. As shown in the FIG. 11, the highest level of immobilization achieved was about 440 ng/cm$^2$, which was more than twice than that achieved for a single layer film grown from pure methanol (about 200 ng/cm$^2$).

TABLE 2

Effect of azide treatment on the second layer polymer thickness for second blocks grown from 10% and 50% water content.

| Azide Exposure Time [min] | Second Layer Thickness [nm] (10% Water) | Second Layer Thickness [nm] (50% Water) |
| --- | --- | --- |
| 0 | 4.6 ± 1.7 | 5.6 ± 1.1 |
| 15 | 8.8 ± 1.5 | 3.4 ± 0.4 |
| 30 | 3.1 ± 0.5 | 6.8 ± 0.1 |
| 60 | 1.7 ± 0.1 | 13.8 ± 0.4 |
| 120 | 2.5 ± 0.5 | 9.9 ± 0.7 |

Figure 12:
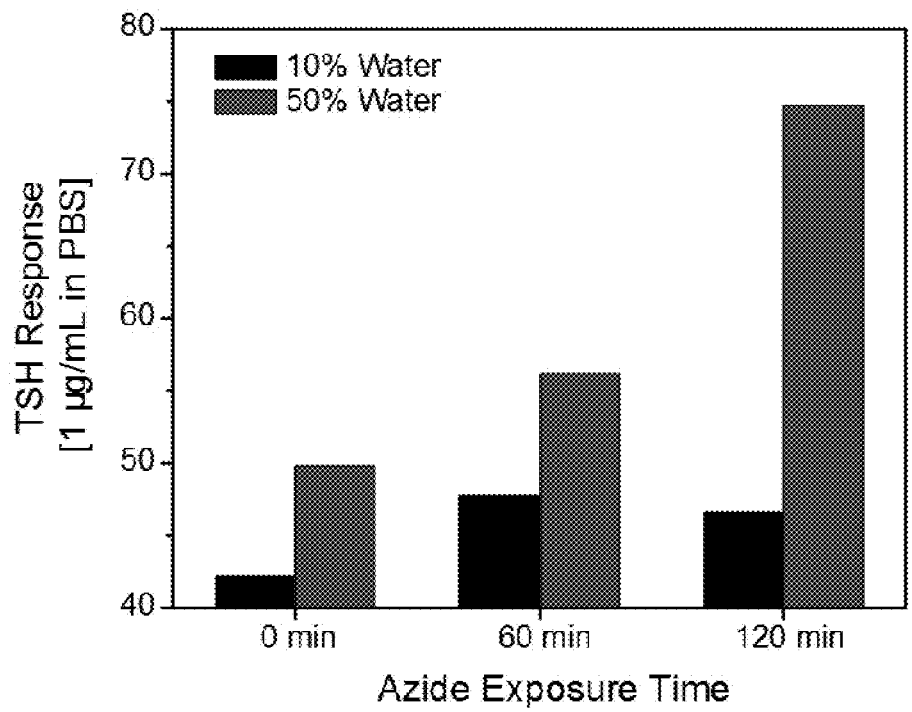
FIG. 12 compares antigen response versus azide exposure time for second layers made using 10% and 50% water content. For 10% SI-ATRP water content, all responses were very similar with surfaces resulting in antigen-antibody saturation. For 50% water content, both the 0 min and the 120 min conditions resulted in saturation. However, despite the 60 min condition having the highest level of antibody immobilization, the response was low due to the restricted ability of the antigen to diffuse through the polymer film thus taking longer to saturate binding. The antigen solution was flowed for a fixed time of 10 min.

The saturated antigen response for azide exposure times of 0, 60, and 120 min for films made using a 10% and 50% water second layer is shown in FIG. 12. The relatively low antibody loading for the 10% water condition for all exposure times resulted in an effective monolayer of antibody and thus gave very similar responses. As expected for the two layer films made using a 50% water content second layer, the lowest level of immobilization also provides the smallest amount of antigen binding. However, the result for 60 min is much less than that for 120 min despite the higher level of antibody binding for the former. For these experiments, PBS spike with 1 μg/mL TSH was flowed over the surface for 10 min. For all experiments except this 60 min one, the 10 min was sufficient to nearly saturate the antigen binding. Thus, while the result for this case shown in FIG. 12 does not represent the saturated value, which would likely be larger, it does indicate that the polymer density of the second block is higher relative to the 120 min exposure time. This indicates that the ability of the antigen to diffuse through the film was more restricted compared to the 120 min film, which would be expected as the azide substitution reaction time increases.

Figure 13:
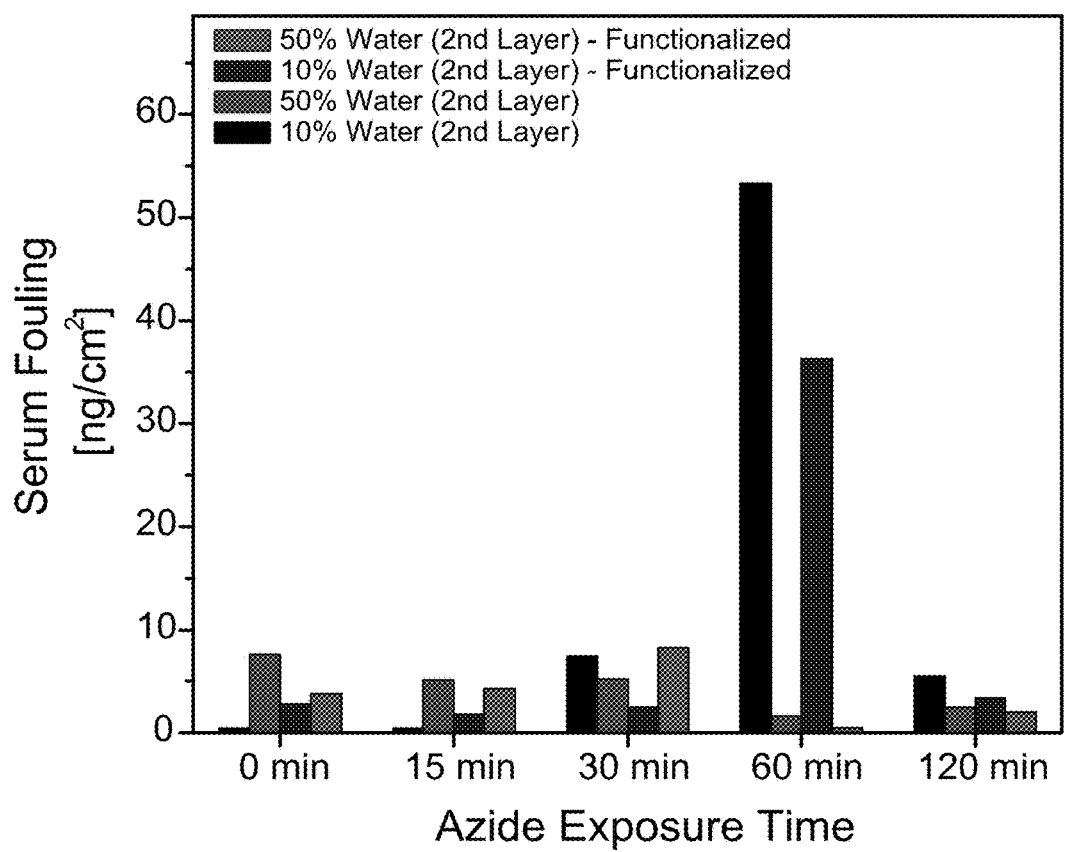
FIG. 13 compares fouling to undiluted human serum versus azide exposure time for second layer films made using 10% and 50% water content.

The non-specific protein adsorption from undiluted human serum as a function of azide exposure time is shown in FIG. 13. All cases except the 1 hour azide time with a second layer grown from a 10% water solvent resulted in excellent functionalized and non-functionalized protein resistant properties with most being at or below ultra low fouling levels. This also indicates that the azide moiety itself does not affect the protein resistant properties of the film. The one exception with high fouling can be explained as a highly substituted film with long polymer chains. The SPR sensor-gram for this film (second layer 10% water content) shows a significant and rapid binding during the antibody immobilization step. However, contrary to the typical SPR sensor-grams for the two-layer films (50% water content), a much larger decrease was observed during the deactivation step. Zwitterionic pCB films take on a slight positive charge following EDC/NHS activation. This would force the long and dilute chains to extend from the surface due to charge-charge repulsion. At a pH of 7.5, anti-TSH maintains a partial negative charge. Thus, the charge interaction between the surface and protein result in an accumulation of antibody near the surface. But, the limited surface area of the dilute polymer chains prevents most of the protein from being covalently bound. Upon deactivation, the surface regains its zwitterionic backbone and as a result the proteins are washed away. This particular conformation of polymer chains can increase the hydrophobicity of the surface by exposure more of the polymer backbone and thereby lead to an increase in fouling. However, these long and dilute chains also lead to very fast antibody saturation of the surface due to the ease of accessibility. Regardless, the combined result of the significant increase in the antigen response for films made using 50% water, with ultra low fouling properties, indicates that this architecture could dramatically positive influence on diagnostic devices.

Figure 14:
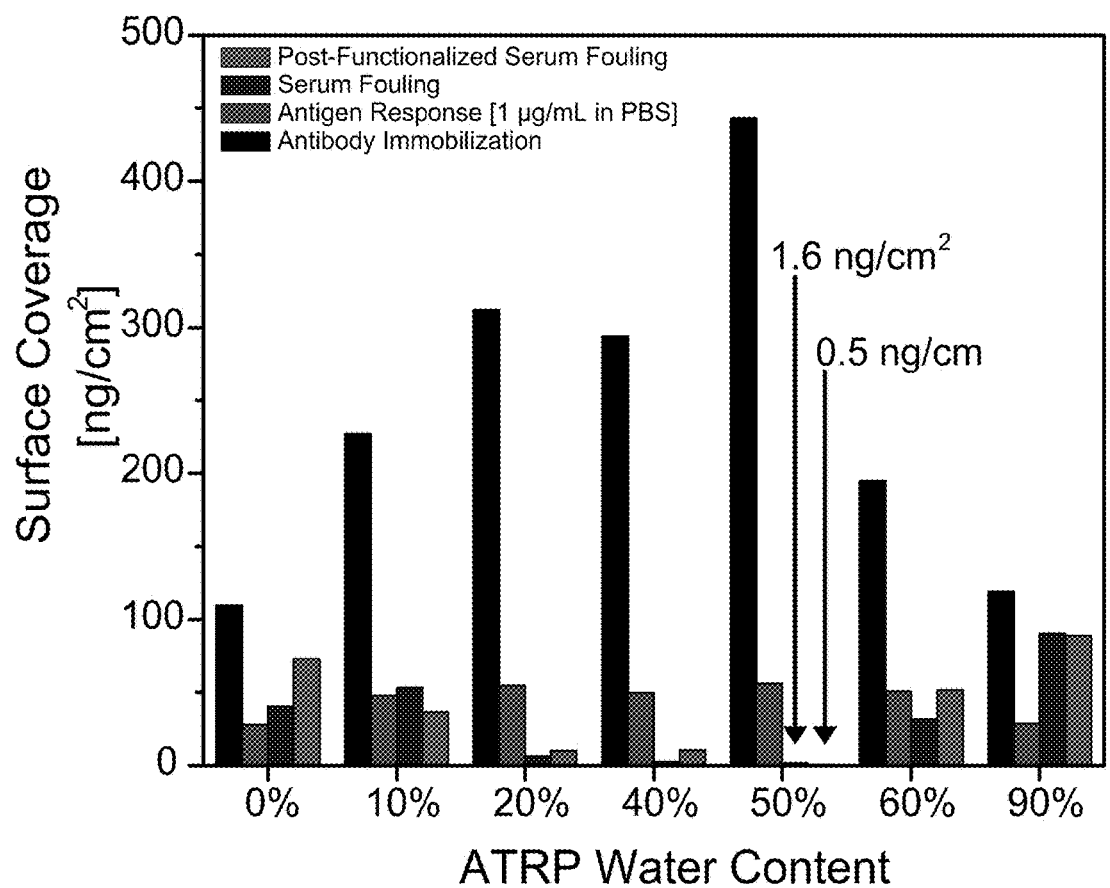
FIG. 14 compares the effect of solvent water concentration on the second layer polymerization using a one hour azide treatment.

Due to the ability of the water concentration to significantly affect the polymer density of the ATRP reaction, the concentration of water was varied from 0-90% for a one hour azide treatment (the condition which enabled the highest antibody immobilization). The functionalized and non-functionalized serum fouling, antibody immobilization, and antigen response are shown in FIG. 14. A peak of the antibody immobilization was found for the 50% water condition. Further investigation of these films by calculating the polymer volume fraction (PVF) in PBS (i.e., the wet polymer density) found that this particular condition had an effective PVF of about 25% where as all others films except for the 0% water second layer, had a PVF of about 43%.

The corresponding second block film thicknesses for each condition are shown in Table 3. The two-layer films made from 20-50% water all resulted in excellent non-fouling properties, had the highest level of immobilization, and also had the highest thickness. It is believed that the two-layer films made from 0% water content grow a very small second layer due to the limited solubility of the highly dense first layer polymer brush in pure methanol resulting in few polymer chains actually being reinitiated. Additionally, the significantly low level of immobilization (about 100 ng/cm$^2$) indicates that very few functionalizable groups are accessible. This could mean that physically absorbed polymer is covering the surface, interacting via charged intermolecular interactions, resulting in a significant presence of the hydrophobic acrylamide backbone being exposed on the surface. The 60% water condition resulted in a similar SPR response as for the 10% water case, thus likely being described by the same phenomena (long and dilute chains), but also with an increase in chain-chain termination reactions which reduced the effective area for immobilization and also lead to exposure of the hydrophobic backbone of the polymer. The 90% water result is likely attributed to a significant presence of radical recombination reactions with the same negative consequences as for the film made using 60% water. With an exception of the two extreme endpoints (0% and 90% water), the similar antigen response for the other water concentrations corresponds with the expected results from 2D surfaces, with the 50% case simply having a low rate of diffusion as discussed above. The two endpoints have the expected response for a 2D surface with low antibody immobilization.

TABLE 3

Second layer films thicknesses as a functional of the polymerization water concentration using a one hour azide treatment.

| ATRP Water Content [%] | Second Layer Thickness [nm] (1 hr Azide) |
| --- | --- |
| 0 | 0.9 ± 0.3 |
| 10 | 1.7 ± 0.1 |
| 20 | 13.2 ± 1.0 |
| 40 | 11.8 ± 1.0 |
| 50 | 13.8 ± 0.4 |
| 60 | 2.9 ± 1.3 |
| 90 | 1.1 ± 0.1 |

In certain embodiments, the films of the invention having two-layer architecture with zwitterionic dual-functional pCB were made via SI-ATRP. Exposing the dense bottom layer to a sodium azide solution to reduce the number of re-initiating sites was effective to double the antibody immobilization all while maintaining ultra low fouling properties to undiluted human serum. Changing the second block polymer density also resulted in a significant increase in the antigen response. These ideal properties of pCB integrated with the two-layer architecture offer the ability to significantly improve detection abilities from undiluted complex media.

Each references cited is incorporated by reference in its entirety.

As used here the term "about" means±5 percent of the recited value.

The following examples are provided for the purpose of illustrating, not limiting, the invention.

EXAMPLES

Example 1

The Preparation, Characterization, and Properties of Representative Polymer Films: Polycarboxybetaine Films by SI-PIMP and SI-ATRP In this example, the preparation, characterization, and properties of representative polymer films of the invention, polycarboxybetaine (pCB) films prepared by SI-ATRP, are described.

Materials.

Copper (I) bromide (99.999%), 2,2'-bipyridine (BPY, 99%), tetrahydrofuran (THF), tetraethylthiuram disulfide (TED), methanol, 4-(2-hydroxyethyl)-1-piperazineethane-sulfonic acid (HEPES), and phosphate buffered saline (PBS, 0.01 M phosphate, 0.138 M sodium chloride, 0.0027 M potassium chloride, pH 7.4) were purchased from Sigma-Aldrich (St. Louis, Mo.). Ethanol (200 Proof) was purchased from Decon Laboratories (King of Prussia, Pa.). Sodium carbonate anhydrous was purchased from EMD Chemicals (Darmstadt, Germany). Sodium chloride (NaCl) and ether were purchased from J. T. Baker (Phillipsburg, N.J.). Sodium acetate anhydrous was purchased from Fluka (subsidiary of Sigma Aldrich, St. Louis, Mo.). 1-Ethyl-3-(3-dimethylaminopropyl) carbodiimide hydrochloride (EDC) and N-hydroxysuccinimide (NHS) were purchased from Acros Organics (Geel, Belgium). Pooled human serum was purchased from Biochemed Services (Winchester, Va.). Antibody to thyroid stimulating hormone (anti-TSH) and the TSH antigen were purchased from ThermoFisher Scientific (Waltham, Mass.). Water used in the experiments was purified using a Millipore water purification system with a minimum resistivity of 18.2 MΩ cm.

Preparation of pCB films via SI-ATRP.

Mercaptoundecyl bromoisobutyrate (SI-ATRP initiator) and carboxybetaine acrylamide (CB) monomer were synthesized as described in J. E. Krause, N. D. Brault, L. Y. Li, H. Xue, Y. B. Zhou, S. Y. Jiang, Macromolecules 2011, 44, 9213-9220, and Z. Zhang, H. Vaisocherova, G. Cheng, W. Yang, H. Xue, S. Y. Jiang, Biomacromolecules 2008, 9, 2686-2692. SAMs on cleaned SPR chips (Z. Zhang, S. F. Chen, Y. Chang, S. Y. Jiang, J. Phys. Chem. B 2006, 110, 10799-10804) of ATRP initiator were formed by soaking overnight in ethanol (0.1 mM). Upon removal, the chips were rinsed with ethanol, THF, ethanol, and then dried and placed in a custom glass tube reactor under nitrogen. In a separate glass tube, CuBr (8.86 mg), 2,2'-bipyridine (57.85 mg), and CB (600 mg) were added and placed under nitrogen. The solids were dissolved in nitrogen purged methanol (4 mL) and transferred to the chips and reacted for 24 hours at 25° C. in a shaker bath. For single layer films, the chips were rinsed with water and stored overnight in PBS. For hierarchical films, the solution was quenched with $CuBr_2$ (275.87 mg) in methanol (4 mL) and then rinsed with methanol, water, and submerged in PBS. The second block was then grown via repeating the above procedure but using a nitrogen purged methanol:water (1:1) and reacting for 3 hours. Termination of bromine groups and replacement with non-reactive azide moieties for reducing the second block polymer density was achieved by submerging the single layer chips in an aqueous azide solution (0.1 M) for 2 hours, removing and rinsing with PBS, water, and then drying for ATRP.

The DTCA photoiniferter was synthesized as described in T. Otsu, Journal of Polymer Science Part a-Polymer Chemistry 2000, 38, 2121-2136. SAMs on cleaned SPR chips (Z. Zhang, S. F. Chen, Y. Chang, S. Y. Jiang, J. Phys. Chem. B 2006, 110, 10799-10804) of the photoiniferter were formed by soaking overnight in THF containing DTCA (2 mM) followed by rinsing with THF and drying with a stream of air. For single layers, the photoiniferter modified chip was transferred to a quartz reaction tube along with 170 mg of CB monomer and placed under nitrogen. Nitrogen purged methanol (5 mL) containing TED (2 μM) was transferred to the reaction tube. The photo-polymerization was then conducted for 30 min using a UV lamp (302 nm) coupled with a 280 nm cutoff filter for preventing deterioration of thiol-gold bonds. Following the reaction, the chips were removed and rinsed with water, PBS, and then submerged in PBS. For the hierarchical films, the single layer film was re-initiated using the identical procedure except for the using nitrogen purged methanol:water (10:90) in the absence of TED.

Ellipsometry.

The thickness of the pCB films were determined using an ellipsometer (Model alpha-SE, J. A. Woollam, Lincoln, Nebr.) using the 380-900 nm wavelength range at an incidence angle of 70°. The results were fitted to a Cauchy module.

Non-Specific Protein Adsorption, Antibody Modification, and Antigen Detection.

The non-specific adsorption, antibody immobilization, and antigen detection was monitored using a four-channel SPR sensor with the Kretschmann configuration and wavelength modulation as described in H. Vaisocherova, W. Yang, Z. Zhang, Z. Q. Cao, G. Cheng, M. Piliarik, J. Homola, S. Y. Jiang, Anal. Chem. 2008, 80, 7894-7901. SPR chips were made of a glass slide coated with titanium (2 nm) followed by gold (48 nm) using an electron beam evaporator. A 1 nm SPR wavelength shift corresponded to a change in the protein surface coverage of 17 ng $cm^{-2}$, which was corrected to account for loss of sensitivity due to the polymer films using previously described methods (W. Yang, H. Xue, W. Li, J. L. Zhang, S. Y. Jiang, Langmuir 2009, 25, 11911-11916; J. Homola, Surface Plasmon Resonance Based Sensors; Springer-Verlag: Berlin, Germany, 2006). For fouling experiments, undiluted human serum or plasma were injected (10 min, 40 μL min-1) and the wavelength shift between PBS baselines was converted to a surface coverage. Anti-TSH was immobilized by first injecting 10 mM sodium acetate (SA, pH 5) followed by EDC/NHS (0.2 M/0.05 M in water) for 7 min at 30 μL min-1. Anti-TSH (50 μg mL-1 in 10 mM HEPES pH 7.5) was injected (20 min, 20 μL min-1) followed by deactivating with 10 mM sodium carbonate containing 300 mM sodium chloride (pH 10) for 10 min and the SA both at 30 μL min-1. Immobilization was calculated as the difference between SA baselines before IgG injection and after deactivation. TSH was antigen binding was then monitored by first injecting PBS and then antigen (1 μg $mL^{-1}$ in PBS at 40 μL $min^{-1}$) following by PBS.

Example 2

The Preparation, Characterization, and Properties of Representative Polymer Films: Polycarboxybetaine Films by SI-PIMP In this example, the preparation, characterization, and properties of representative polymer films of the invention, polycarboxybetaine (pCB) films prepared by SI-PIMP, are described.

Materials.

Solvents including acetone, methanol (MeOH) and tetrahydrofuran (THF) at the highest available purity were obtained from Sigma-Aldrich (Milwaukee, Wis.). CB monomer and photoiniferter (N,N-(diethylamino)-dithiocarbamoylbenzyl(trimethyoxy)thiol (DTCA)) were synthesized by literature methods. Fibrinogen, lysozyme, tetraethylthiuram disulfide (TED), N-hydroxysuccinimide (NHS) and ethyl (dimethylaminopropyl) carbodiimide (EDC) were obtained from Sigma-Aldrich. Human thyroid stimulating hormone (TSH) antibody and antigen were from Thermo Scientific (Waltham, Mass.). Deionized water with minimum resistivity of 18.0 MΩ cm used in the experiment was from a Millipore water purification system (Billerica, Mass.). The buffers including 150 mM phosphate buffered saline (PBS) at pH 7.4, 10 mM sodium acetate buffer (SA) at pH 5.0, 10 mM sodium carbonate buffer (SC) with 300 mM NaCl at pH 10 and 10 mM HEPES at pH 7.5 were prepared for biomolecular conjugation and bioassay. The pH values were adjusted with HCl or NaOH. The buffers were degassed prior to use. Human plasma used for challenging the surface coatings were purchased from BioChemed Services (Winchester, Va.).

Preparation of Polymer Brushes Via Photoiniferter-Mediated Polymerization (PIMP).

The UV-ozone cleaned SPR chip was immersed in THF containing 2 mM DTCA at room temperature for 24 h in order to form a self-assembled monolayer (SAM) of photoiniferter, followed by intensive rinsing with THF and drying with a stream of filtered air. The photoiniferter modified chip was transferred to a quartz reaction tube containing 170 mg of CB monomers and TED molecules with different concentrations for growth of the first pCB layer. The reaction tube was placed under nitrogen protection, sealed with a rubber septum and wrapped with parafilm. The solvents used were deoxygenated with a continuous stream of dry nitrogen for more than 30 min, and then 5 mL of MeOH was transferred to the reaction tube using a syringe under nitrogen protection. The photo-polymerization was conducted by means of a UV lamp emitting light at 302 nm coupled with 280 nm cutoff filter in order to avoid the deterioration of thiol-gold bonds. 31 After the 30 min UV exposure, the chips were removed and rinsed with water and PBS to remove loosely bound polymers. For the regrowth of pCB for the second layer, the preparation method was the same as that for the first layer, but the TED was not needed and the water content in the solvents was adjusted to optimize the thickness of the films.

Ellipsometry.

The dry thicknesses (d) of pCB was determined using an ellipsometer (model alpha-SE, J. A. Woollam, Lincoln, Nebr.) with a light source with wavelengths ranging from 380 to 900 nm at a fixed incident angle of 70°. The thickness measurements were taken on six spots on each sample. The results were analyzed using a Cauchy model. The refractive index of polymer films was around 1.5.

SPR Measurements.

A four-channel SPR sensor was used (H. Vaisocherová, W. Yang, Z. Zhang, Z. Cao, G. Cheng, M. Piliarik, J. Homola, S. Jiang, Analytical Chem., 80, 7894 (2008)). Briefly, the SPR sensor, based on the Kretschman configuration, detects the changes of the refractive index arising from the molecular adsorption at the sensor chip surface. The sensor chip was washed with PBS and water and dried with a stream of air. On the glass side of the chip a drop of the refractive index matching liquid (Cargille, Cedar Grove, N.J.) was placed and then attached onto the base of the prism. The flow cell was mounted on the chip and filled with the buffer by a peristaltic pump (Ismatec, Vernon Hills, Ill.). A baseline signal was established by flowing PBS at a flow rate of 30 µL min$^{-1}$ over the chip surface for 20 min. For the fouling test, undiluted blood serum and plasma were flowed over the chip at a flow rate of 30 µL min$^{-1}$ for 10 min, followed by PBS washing. For quantitative estimation of surface mass coverage with the SPR sensor operating at a resonant wavelength of around 750 nm, a 1 nm SPR wavelength shift represents a change in the protein surface coverage of 17 ng cm$^{-2}$. The signal calibration and the estimation for surface mass coverage (Γ) are described in Yang, W.; Xue, H.; Li, W.; Zhang, J. L.; Jiang, S. Y. Langmuir 2009, 25, 11911; and Vaisocherova, H.; Zhang, Z.; Yang, W.; Cao, Z. Q.; Cheng, G.; Taylor, A. D.; Piliarik, M.; Homola, J.; Jiang, S. Y. Biosens. Bioelectron. 2009, 24, 1924.

Protein Modification and Bioassay for TSH Hormone.

The functionalization of pCB layers with TSH antibodies through EDC/NHS coupling chemistry was in situ monitored by means of the SPR sensor. SA buffer was flowed over the surface to swell the polymer and to establish the baseline for 20 min. The activation reagent, EDC/NHS mixture in water with a molar ratio of 0.2 M/0.05 M, was introduced at a flow rate of 30 µL min$^{-1}$ for 7 min, followed by 5 min flushing of SA buffer to flow away unreacted EDC/NHS chemicals. HEPES buffer spiked with TSH antibodies at a concentration of 50 µg mL$^{-1}$ was flowed through the channel at a flow rate of 20 µL min$^{-1}$ for 20 min. Afterwards, the unreactive groups were hydrolyzed to recover to carboxyl acid groups by washing with basic SC buffer at a flow rate of 30 µL min$^{-1}$ for 10 min, followed by SA buffer. The binding capacity was estimated as the surface mass changes before the IgG injection and after hydrolysis in SA buffer.

The detections for TSH antigens spiked in PBS at a concentration of 1 µg mL$^{-1}$ were performed after TSH IgG functionalization on pCB layers. Prior to and after the assay, PBS buffer was flowed over the polymer surfaces for 20 min. Samples containing TSH antigens were introduced into the channels of the flow cell at a flow rate of 30 µL min$^{-1}$ and flowed until the binding curve reached a plateau.

Atomic Force Microscopy (AFM) Imaging.

The pCB films with and without IgG functionalization on SPR chips were dried with a stream of filter air and attached onto the AFM sample holder. The AFM secondographic images were taken in a taping mode using a Dimension 3100 AFM (Digital Instruments/Veeco, Woodbury, N.Y.). Non-contact silicon cantilevers with a resonant frequency of 315 kHz and a force constant of 48 N m$^{-1}$ (MikroMasch, Tallinn, Estonia) were used.

Example 3

The Preparation, Characterization, and Properties of Representative Polymer Films: Polycarboxybetaine Films by SI-ATRP In this example, the preparation, characterization, and properties of representative polymer films of the invention, polycarboxybetaine (pCB) films prepared by SI-ATRP, are described.

Materials.

Copper (I) bromide (99.999%), 2,2'-bipyridine (BPY, 99%), tetrahydrofuran (THF), methanol, 4-(2-hydroxyethyl)-1-piperazineethanesulfonic acid (HEPES), and phosphate buffered saline (PBS, 0.01 M phosphate, 0.138 M sodium chloride, 0.0027 M potassium chloride, pH 7.4)

were purchased from Sigma-Aldrich (St. Louis, Mo.). Ethanol (200 Proof) was purchased from Decon Laboratories (King of Prussia, Pa.). Sodium carbonate anhydrous and sodium azide were purchased from EMD Chemicals (Darmstadt, Germany). Sodium chloride (NaCl) and ether were purchased from J. T. Baker (Phillipsburg, N.J.). Sodium acetate anhydrous was purchased from Fluka (subsidiary of Sigma Aldrich, St. Louis, Mo.). 1-Ethyl-3-(3-dimethylaminopropyl) carbodiimide hydrochloride (EDC) and N-hydroxysuccinimide (NHS) were purchased from Acros Organics (Geel, Belgium). Pooled human serum was purchased from Biochemed Services (Winchester, Va.). Antibody to thyroid stimulating hormone (anti-TSH) and the TSH antigen were purchased from ThermoFisher Scientific (Waltham, Mass.). Water used in the experiments was purified using a Millipore water purification system with a minimum resistivity of 18.2 MΩ cm.

Synthesis of Carboxybetaine Acrylamide (CBAA) Monomer.

(3-Acryloylamino-propyl)-(2-carboxy-ethyl)-dimethylammonium (CBAA) was synthesized by reacting 48 mL of DMAPA with 25 g of β-propiolactone in 400 mL of anhydrous acetone at 0° C. under nitrogen protection. After removing the ice bath at 20 minutes, the solution was allowed to warm up to room temperature. After 6 hours, the product was filtered, washed with ether, and allowed to dry under vacuum. The rough product, a white precipitate, was re-dissolved in a 30% (v/v) triethylamine in methanol solution and stirred overnight. After concentrating the solution, the CBAA was precipitated with acetone and then filtered. The solids were suspended in acetone and ether, for 1 hour each, dried under vacuum, and then stored at 4° C. Yield: 61%. $^1$H NMR (Bruker 500 MHz, DMSO-d6): 8.61 (t, 1H, N—H), 6.28 (t, 1H, CHH=CH), 6.13 (t, 1H, CHH=CH), 5.61 (t, 1H, CHH=CH), 3.44 (t, 2H, N—CH2-CH2-COO), 3.21 (m, 4H, NH—CH2-CH2-CH2), 2.97 (s, 6H, N—(CH3)2), 2.25 (t, 2H, CH2-COO), 1.87 (t, 2H, NH—CH2-CH2-CH2).

Preparation of Two-Layer PolyCBAA Films.

SPR sensor chips coated with ATRP initiator self-assembled monolayers were prepared by soaking the gold-coated substrates into 1 mM mercaptoundecyl bromoisobutyrate in pure ethanol for 24 hours. The chips were then removed, rinsed with ethanol, THF, and ethanol, and the blown dry using filtered compressed air and placed into a custom glass tube reactor for ATRP. In a separate glass tube, 8.86 mg CuBr, 57.85 mg 2,2'-bipyridine (BPY), and 600 mg of CBAA were added. Both tubes were then placed under nitrogen protection. Nitrogen purged methanol (4 mL) was then added to the solids. Once completely dissolved (about 15 min), the mixture was then transferred to the reactor tube under nitrogen protection and allowed to react for 24 hours at 25° C. in a shaker set to 120 rpm. The reaction was removed and quenched with a solution containing methanol (4 mL) and CuBr$_2$ (275.87) in order to maintain the maximum number of surface terminal bromine grown polymer chains. After mixing for two minutes, the chips were rinsed with methanol, water, and then submerged in PBS.

The second polymer block was then grown by repeating the above ATRP procedure and adjusting only the solvent ratio between nitrogen purged methanol and water in the final reaction mixture. For the re-initiated polymerization was allowed to react for 3 hours at 25° C. in a shaker set to 120 rpm. Following the reaction the chips were rinsed with copious amounts of water and then submerged overnight in PBS. In order to terminate bromine groups on the surface and replace them with non-reactive azide moieties to further reduce the polymer density of the second block, the chips were submerged in an aqueous solution of sodium azide (6.5 mg/mL) and mixed at room temperature. After a specific time, the chips were removed, dipped in PBS, rinsed with water, dried, and the placed into the custom tube reactor for re-initiating ATRP.

SPR Sensor, Chips, and Calibration of the Surface Sensitivity.

A laboratory SPR sensor developed at the Institute of Photonics and Electronics, Prague, Czech Republic was used as described in H. Vaisocherová, W. Yang, Z. Zhang, Z. Cao, G. Cheng, M. Piliarik, J. Homola, S. Jiang, Analytical Chem., 80, 7894 (2008). The SPR is based on the attenuated total reflection method and wavelength modulation. It is equipped with a four-channel flow-cell, temperature control, and uses a peristaltic pump for delivering samples. SPR sensor chips were made of a glass slide coated with an adhesion-promoting titanium film (about 2 mm) followed by a gold film (about 48 nm) using an electron beam evaporator. Because the SPR sensitivity depends on the distance of the binding event from the SPR active surface, the sensor response due to the polymer films was calibrated as described in H. Vaisocherova et al., 2008 (above).

Determination of Polymer Film Thickness, Refractive Index, and Polymer Density.

Dry and wet film thickness and refractive index (RI) measurements were determined using a multi-wavelength ellipsometer (J. A. Woollam Co., Inc., Model alpha-SE). A liquid cell with a volume of 0.5 mL supplied by the manufacturer was used for obtaining the wet measurements. The data was analyzed via fitting a Cauchy model for a bare SPR substrate which enables the film thickness and refractive index to be simultaneously determined without using predetermined or assumed Cauchy coefficients. The wet and dry refractive index measurements were then used with the effective medium approximation for calculating the film polymer volume fraction, PVF, (i.e., the wet polymer density)

Measurements of Non-Specific Protein Adsorption by SPR.

The non-specific protein adsorption of the pCBAA polymer films formed via SI-ATRP was determined with a SPR biosensor using a flow rate of 50 μL/min at 25° C. After first establishing a baseline using PBS, undiluted human serum was flowed for 10 minutes, followed by buffer to reestablish the baseline. Protein adsorption was quantified as the difference between buffer baselines and converted to a surface coverage using the appropriate sensitivity factor.

In Situ Functionalization of pCB Polymer Surfaces.

The functionalization procedure was monitored step-by-step in real time using an SPR sensor at 25° C. Sodium acetate buffer (10 mM) at pH 5.0 (SA) was first injected at 30 μL/min to obtain a stable baseline. The carboxylate groups of the polymer surface were then activated by flowing a freshly prepared solution of 0.05 M NHS and 0.2 M EDC in water for 7 minutes. Followed by a brief injection of SA buffer, a solution of anti-TSH (50 μg/mL) in HEPES buffer (pH 7.5) was flowed over the activated surface for 20 minutes at 20 μL/min. Subsequent washing of the functionalized surface for 10 minutes with 10 mM sodium carbonate (pH 10) containing 0.3 M NaCl (SC) at 30 μL/min removed non-covalently bound ligands and deactivated residual NHS-esters. SA buffer was then used to reestablish a stable baseline. The amount of immobilized antibodies was determined as the different between the SA injection following EDC/NHS activation and the final baseline.

Measurements of Post-Functionalized Non-Fouling and Specific Protein Activity.

Following antibody immobilization, the pCBAA surface was washed with PBS buffer until a steady baseline was established at 50 µL/min and 25° C. For post-functionalized non-fouling, undiluted human blood serum was then injected for 10 minutes followed by PBS for an additional 15 minutes. The net adsorption was calculated as the difference between buffer baselines and converted to a surface coverage. Specific antigen detection was compared by measuring the response at saturation for each polymer film. After establishing an initial buffer baseline, PBS spiked with TSH at 1000 ng/mL was flowed through sensor for 10 minutes followed by buffer. The saturated antigen binding was calculated as the difference between the original buffer baseline and the maximum response which was then converted to a surface coverage.

Example 4

Packing Density of Representative Zwitterionic Polymer Brushes: Refractive Index In this example, the effects of chain packing density on protein resistance properties of surface-initiated polymer brushes as measured by refractive index are described.

Polymer brushes can theoretically be described via chain lengths and chain-to-chain distances. Practically, ellipsometry is often used to measure the film thickness, which has been correlated to ultra low fouling properties of polymer brushes to undiluted human blood plasma and serum. However, ellipsometry also calculates an additional parameter, the film refractive index (RI). This film RI can be used to characterize the polymer density, but is often overlooked in practice. The film RI may be an even more important parameter for identifying nonfouling polymer films. By varying the water content in the surface-initiated atom transfer radical polymerization (SI-ATRP) of zwitterionic carboxybetaine, protein resistance to undiluted human serum was determined to be strongly dependent on the film RI. A minimum value of about 1.5 RI units was necessary to achieve <5 ng/cm$^2$ of protein adsorption, measured using a surface plasmon resonance biosensor.

The swelling behavior of a film, determined as the ratio of wet and dry thicknesses, is one approach to study polymer density. Tightly packed polymer brushes in a good solvent will swell less than lower density brushes. These tightly packed films have high extension in the dry state and significant further extension is limited upon swelling. Ellipsometry also calculates an additional parameter, the film refractive index (RI). This film RI can be used to characterize the polymer density, but is often overlooked in practice. Because the RI measurements of films account for two factors, the medium (e.g., air, RI of about 1.0) as well as the material itself (e.g., proteins, RI of about 1.53), the RI of a polymer film will increase with density. Importantly, the RI can be measured in the dry state, thus offering a convenient and simple approach for film characterization.

SI-ATRP was used to investigate a parameter capable of characterizing and predicting ultra low fouling properties of pCBAA films. SI-ATRP is a controlled radical polymerization that enables the formation of polymer brushes with low polydispersity, high density, and a desired thickness. It is based on the equilibrium reaction between activated propagating chains and those that have been capped by a deactivating complex. The highly localized and low concentration of immobilized initiators in SI-ATRP (relative to solution ATRP) is a major challenge for achieving control due to the low concentration of persistent deactivator which can trap the propagating radical. The rate of polymerization is highly dependent upon the ratio of activator to deactivator; reduction in the latter leads to fast and uncontrolled growth. This increases the film polydispersity as well as the probability of irreversible chain-chain termination events thereby affecting the polymer density. For aqueous ATRP, the water content has been shown to sharply affect the rate of reaction due to a significant loss of deactivator, among other side reactions. This has previously enabled the use of SI-ATRP with 2-hydroxyethylmethacrylate (HEMA) to obtain a peak film thickness at some medium water concentration. Because the polydispersity of a film is related to its polymer density, varying the content of water during SI-ATRP enables a convenient approach for studying the effect of film thickness and polymer density on the nonfouling properties of pCBAA brushes.

Ultra low fouling properties of pCBAA films formed via SI-ATRP was investigated using surface plasmon resonance (SPR) biosensors. Protein resistance to undiluted human serum was studied as a function of the polymer thickness and dry refractive index, the latter representing the polymer density. The results indicated that the nonfouling properties of pCBAA films were not affected much by the polymer thickness, but instead were strongly dependent on the RI.

Materials.

All chemicals were purchased from Sigma-Aldrich (St. Louis, Mo.) and Decon Laboratories (King of Prussia, Pa.). Pooled human serum was purchased from Biochemed Services (Winchester, Va.).

Preparation of pCBAA Films.

UV cleaned SPR sensor chips coated with ATRP initiator self-assembled monolayers were prepared by soaking in 0.1 mM mercaptoundecyl bromoisobutyrate in pure ethanol for 24 hours. The chips were then removed, rinsed with ethanol, THF, and ethanol, and the blown dry using filtered air and placed into a custom glass tube reactor. In a separate glass tube, 8.86 mg CuBr, 57.85 mg 2,2'-bipyridine, and 600 mg of CBAA were added. Both tubes were then placed under nitrogen protection. Appropriate volumes of nitrogen purged methanol and water were then added (total volume was 4 mL) to the solids according to the necessary solvent ratio. After dissolving the solids (about 15 min), the mixture was then transferred to the reactor tube under nitrogen protection and allowed to react for 3 hours at 25° C. in a shaker set to 120 rpm. Following the reaction the chips were rinsed with water and then submerged overnight in PBS.

SPR Sensor, Chips, and Calibration of the Surface Sensitivity.

A laboratory SPR sensor developed at the Institute of Photonics and Electronics, Prague, Czech Republic was used as described above. This custom built SPR is based on the Kretschmann geometry of the attenuated total reflection method with wavelength modulation and is equipped with a four-channel flow-cell, temperature control, and uses a peristaltic pump for delivering samples. SPR sensor chips were made of a glass slide coated with an adhesion-promoting titanium film (about 2 nm) followed by a gold film (about 48 nm) using an electron beam evaporator. Because SPR sensitivity depends on the distance of the binding event from the SPR active surface, the sensor response due to the polymer films was calibrated using methods described above.

Determination of Polymer Film Thickness, Refractive Index, and Polymer Density.

Dry and wet film thickness and refractive index (RI) measurements were determined using a multi-wavelength ellipsometer (J. A. Woollam Co., Inc., Model alpha-SE). A liquid cell with a volume of 0.5 mL supplied by the manufacturer was used for obtaining the wet measurements. The data was analyzed via fitting a Cauchy model for a bare SPR substrate which enables the film thickness and refractive index to be simultaneously determined without using predetermined or assumed Cauchy coefficients. The wet and dry refractive index measurements were then used with the effective medium approximation for calculating the wet polymer density (i.e., film polymer volume fraction (PVF). See Equation 1.

$$PVF = \frac{(n_p^2 - n_b^2)(n_{p\text{-}dry}^2 + 2n_b^2)}{(n_p^2 - 2n_b^2)(n_{p\text{-}dry}^2 + n_b^2)} \quad (1)$$

$n_p$ = RI of polymer brush in PBS $n_{p\text{-}dry}$ = RI of polymer brush in air $n_b$ = RI of PBS, 1.333

The wet polymer density (PVF) in PBS of pCBAA films made via SI-ATRP using 0%, 10%, 50% and 90% water (v/v) was calculated using Equation 1 as described above.

Measurements of Nonspecific Protein Adsorption by SPR.

Nonspecific protein adsorption of the pCBAA polymer films was determined with a SPR biosensor using a flow rate of 50 µL/min at 25° C. After first establishing a baseline using PBS, undiluted human serum was flowed for 10 minutes, followed by buffer. Protein adsorption was quantified as the difference between buffer baselines and converted to a surface coverage using the appropriate sensitivity factor.

Results.

The pCBAA films were achieved by varying the SI-ATRP water content from 0-90% (v/v) using a fixed reaction time. The corresponding dry film thicknesses (8-40 nm), dry RI values (1.48-1.56 RI units (RIU)), and protein adsorption to undiluted human serum indicated a maximum value for both the thickness and RI as the polymerization rate was varied. All films except for those made using 90% water (v/v) enabled ultra low fouling properties. Thus it appears that thickness does not play a significant role in protein resistance. Because the dry film RI is proportional to the polymer density, the relatively high fouling for the films made from 90% water is likely due to its lower polymer density with a correspondingly reduced hydration, the primary mechanism of protein resistance. In the initial stages of polymerization for a given reaction, the thickness as well as the polymer density are simultaneously changing. Thus, the thickness can still serve as an indirect measure for achieving nonfouling surfaces. However, the results here illustrate that the polymer density may be the direct and more important parameter for reflecting protein resistance. This enables one to achieve ultra low fouling with a densely packed thin film.

A minimum RI value (about 1.5) was observed, representing a minimum polymer density for achieving ultra low fouling properties with pCBAA films. The pCBAA film had a peak thickness at about 40 nm using 20% water (v/v). The ATRP reaction rate has been shown to be significantly affected by the concentration of water. As the water content increases, the rate of polymerization increases primarily due to loss of deactivator. For example, polymer films grown using 0% water enable a relatively slow reaction with low polydispersity. Under this condition, the final thickness is likely limited by the maximum solubility of the dense brushes in methanol. Here, the solvation ability of methanol gradually changes from good to bad as the chain length increases and the solubility approaches saturation. This leads to confinement of the growing chain end, limiting the access of free monomer as well as the catalyst complex thus preventing further propagation. Increasing the amount of water leads to both an increase in the accessibility of the chain end due to the super-hydrophilicity of zwitterionic carboxybetaine materials and an increase in the polymerization rate, resulting in larger film thicknesses. However, this comes at the expense of more polydispersity (i.e., loss of control) and more frequent irreversible chain-chain radical termination events. If such recombination events occur too often, as in the case of very high water concentrations, the film thickness can decrease. Therefore, increasing the water content should initially lead to larger film thicknesses until sufficient recombination occurs.

The RI measurements have a similar trend to the film thicknesses. Because the dry film RI is proportional to polymer density, these results indicate that the density initially increases and then rapidly decreases with the rate of the ATRP reaction. The films made from 0% and 90% water had the lowest densities in air, despite the former being made under the most controlled conditions (i.e., water-free) which would be expected to yield a very high density polymer brush. The films made using 10%-60% water had the highest polymer densities. These are attributed to changes in surface morphology and packing structure of the film due to the increased polydispersity allowing for ion-pair interactions of the loose chains, which collapse onto the surface in the presence of air, similar to a multilayer polyelectrolyte film. The low value achieved for the film made from 0% water is due to the highly uniform and monodisperse brush containing few collapsed chains. The result for the film made with 90% water (v/v) was likely caused by excessive radical termination reactions which occur under this condition, thus creating little pockets for air thereby reducing the density. This is supported by the rapid decrease in thickness for films made from high water concentrations.

The wet polymer density (polymer volume fraction (PVF)) in PBS of several films was also studied. A low wet density will have a large amount of solvent relative to polymer material thus enabling a large degree of swelling, corresponding to a "loose" polymer structure. The films made using 0%, 10%, 50%, and 90% water had wet densities of 62%, 48%, 35%, and 73%, respectively. The initial decrease follows the expected increase in polydispersity for the faster polymerizations, such as with high water concentrations. Therefore, because the films made using 90% water elicit widespread termination events, as indicated by the rapid decrease in thickness, it is believed that such significant chain-end recombination restricted the polymer from swelling yielding a high wet density.

In summary, the data revealed a RI range of 1.50-1.56 RIU with wet polymer densities from 62-35% PVF that allowed zwitterionic pCBAA films to achieve <5 ng/cm$^2$ of nonspecific protein adsorption from undiluted human serum.

The results enable a model of the polymer structure as a function of water content (polymerization rate) and protein resistance to be developed. The water free scenario results in thin but uniform and dense polymer brushes with low polydispersity and ultra low fouling properties. As the water concentration increases, the polydispersity increases but the amount of termination is not excessive enough to significantly suppress film growth. The continued propagation enabled by the lack of recombination provides for a similarly dense base-layer to form and thus ultra low fouling properties can be achieved. The scenario for high water content occurs with very fast and uncontrolled reactions in which radical recombination frequently occurs. This restricts polymer growth and reduces the polymer density thereby affecting the film hydration and subsequent protein resistance.

Example 5

Packing Density of Representative Zwitterionic Polymer Brushes: Swell Ratio

In this example, the effects of chain packing density on protein resistance properties of surface-initiated polymer brushes as measured by swelling ratio are described.

Polymer brushes based on dual-function poly(carboxybetaine acrylamide) (pCB) were prepared via surface-initiated photoiniferter-mediated polymerization to determine the effects of the chain packing density on the protein resistant properties of surface-initiated polymer brushes. By adjusting the UV radiation time and solvent polarity, films with different thicknesses and packing densities were characterized via ellipsometry under both dry and wet conditions. Non-specific protein adsorption from undiluted human plasma and serum was then measured with a surface plasmon resonance (SPR) biosensor. The results indicated that the dry film thickness alone is not a sufficient characterization for evaluating non-fouling properties and the chain packing density must be considered. Based on this study, highly-packed and ultra-thin pCB films were developed and applied to the detection of human thyroid stimulating hormone (TSH) in serum by SPR with high sensitivity and specificity.

Previous studies have identified the optimized "dry" thicknesses of pCB brushes for ultra-low fouling properties as being in the range of 20-30 nm. In bio-applications, the films are typically used in an aqueous environment. Hence, the "wet" thickness of the polymer brush films should be taken into account when determining the effects of thickness on non-fouling properties. The ratio of stretched and collapsed polymer film thicknesses was used to determine a swelling ratio as a means to characterize the effects of chain packing density on protein resistance. The packing density and film thickness of tethered pCB brushes prepared via SI photoiniferter-mediated polymerization were varied by adjusting the UV radiation time and solvent polarity. The resulting pCB film thicknesses in air and physiological buffer were measured and correlated with the non-fouling properties to undiluted human serum and plasma. Human thyroid stimulating hormone (TSH) detection using SPR integrated with a highly packed and thin pCB film as a binding platform demonstrated remarkable sensitivity and specificity.

Growth and Non-Fouling Properties of pCB Films.

The SI polymerization was carried out in the mixture of ethanol and water with a volume ratio of 75:25 with a monomer concentration of 0.15 M. The thickness (d) and swelling ratio ($\sigma$) of prepared pCB films was measured using an ellipsometer and analyzed as a function of the UV radiation time. The thicknesses of pCB films in air and PBS increased with the UV radiation time. After 30 min of UV exposure, the film grew to thicknesses of $d_{dry}$=22.1±1.1 nm and $d_{wet}$=62.0±3.1 nm in air and PBS, respectively. However, the swelling ratio showed the opposite trend, declining from 3.6 to 2.8 for the 30 min UV radiation time. For the fouling test with undiluted blood serum and plasma, the fouling level decreased with increasing UV radiation time. As the film grew to $d_{dry}$=22.1±1.1 nm and $\sigma$=2.8, it exhibited ultra-low fouling properties, which is in agreement with those observed on pCB and poly(hydroxypropyl methacrylate) previously prepared via SI-ATRP.

A steep increase in thickness was observed at the beginning of polymerization, which was more pronounced for the "wet" thickness. The non-linear growth rate of pCB provides evidence that surface-tethered free radicals are lost during the course of polymerization. This observation confirms the feature of the initial rapid growth in photoiniferter-mediated photo-polymerization. The stretching of polymers decreased with UV radiation time. The rapid growth and termination of tethered polymers rendered the film sparse and the polymer chains coiled, giving rise to a "mushroom" conformation, manifested in the high swelling ratio. As the "living" polymer chains continue to grow, the chains interact with each other and, hence, stretch to become a "brush" conformation. The film thickness and chain packing density synergistically affect the non-fouling properties.

Solvent Effects on Brush Packing Density and Non-Fouling Properties.

Figure 15A:
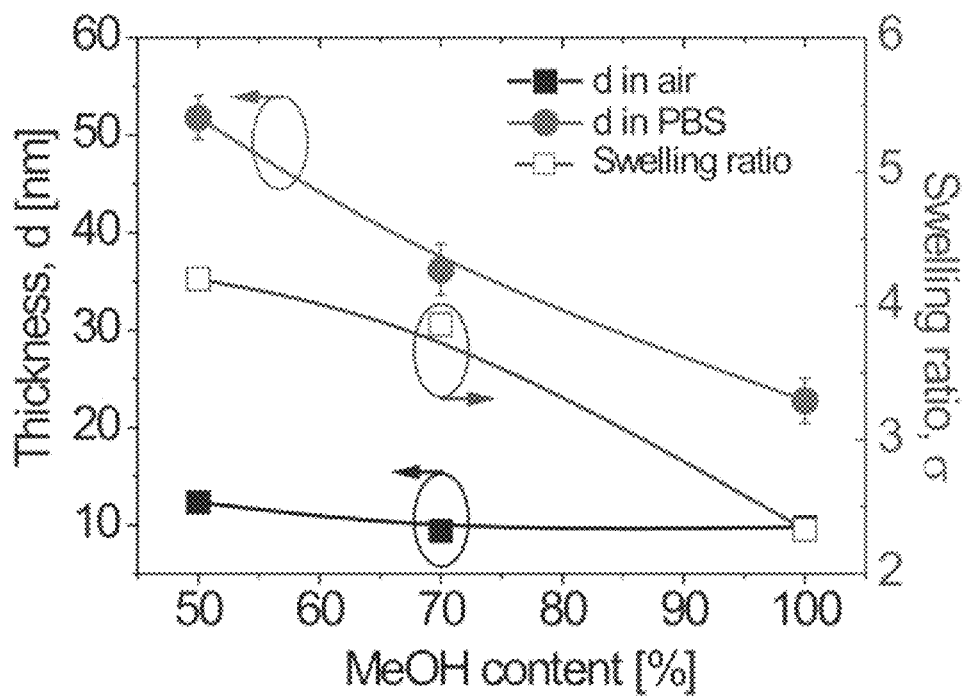
FIG. 15A compares thicknesses and swelling ratios of pCB films with dry thicknesses of about 10 nm. The thicknesses in air (full squares) and PBS (full circles) and the swelling ratio (hollow squares) were measured using an ellipsometer.
Figure 15B:
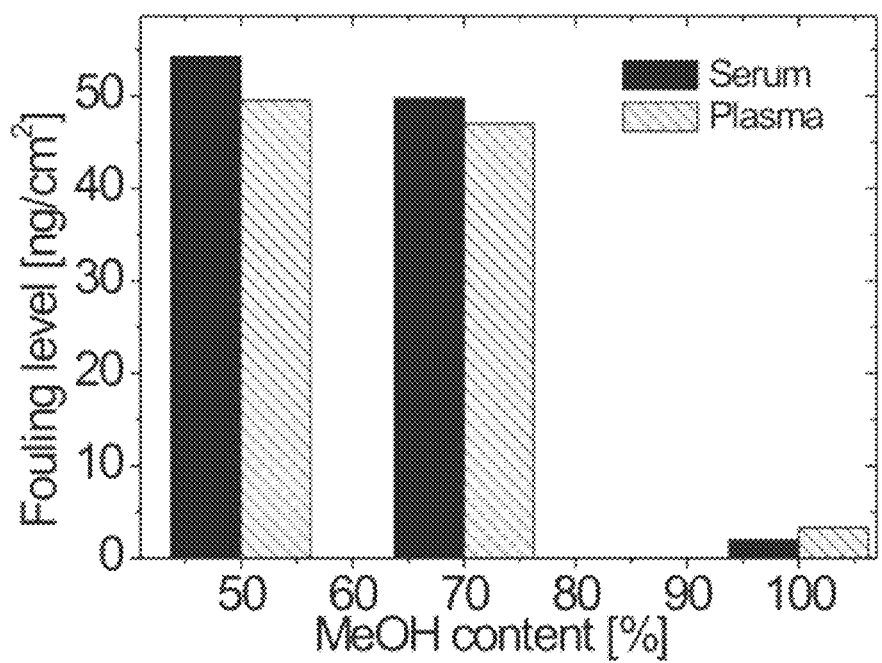
FIG. 15B compares the fouling tests for pCB films from (a) with serum (darker bars) and plasma (lighter bars) were determined using a SPR sensor.
Figure 16:
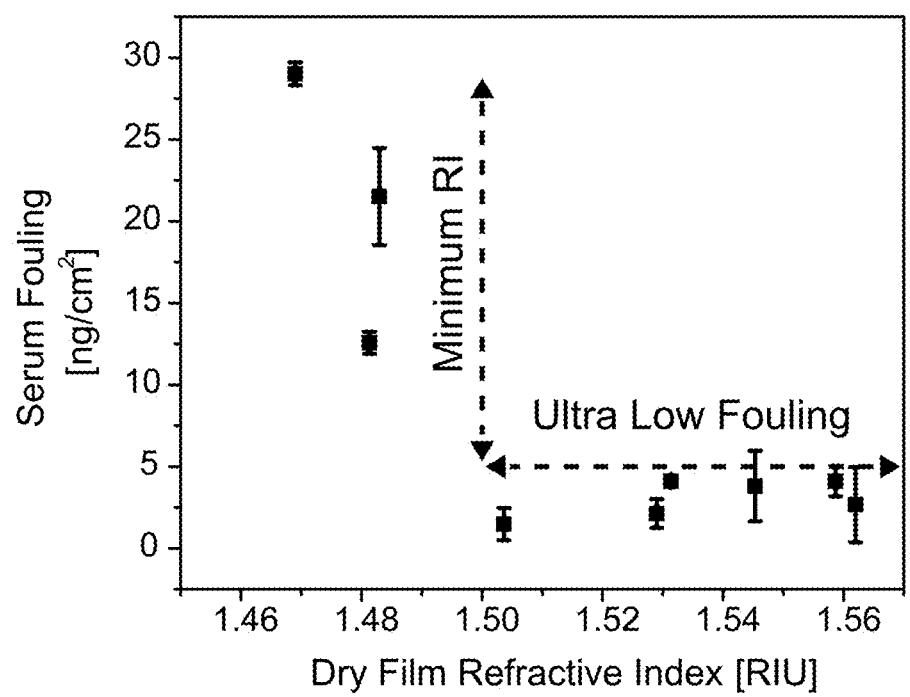
FIG. 16 compares serum fouling versus dry film refractive index and illustrates a minimum packing density that is necessary to achieving ultra low fouling properties.

In order to solidify the correlation between chain packing density and non-fouling properties, a pCB film with a thin thickness and high packing density was prepared through changing the solvent content in the polymerization. The UV radiation time and monomer concentration remained constant at 30 min and 0.15 M, respectively, and the volume ratio of methanol to water in solution was changed from 50% to 100%. Film thicknesses in air and in PBS decreased with the ratio of methanol, as well as their swelling ratio, which dropped from 3.7 to 2.5. The surface resistance to fouling from serum and plasma on pCB samples indicates that with increasing methanol content during photo-polymerization, non-specific adsorption on surfaces tends to decrease, reaching the ultra low fouling level. Furthermore, two samples were prepared from MeOH:H2O ratios of 50:50 and 70:30 for shorter radiation time, which exhibited similar dry film thicknesses but swelling ratios distinct from those prepared by the 100% methanol condition (FIG. 15A). Clearly, although these films have similar film thicknesses, the pCB films with high swelling rations or highly loose chain densities show significantly higher fouling levels than that with low swelling ratio or highly packed density (FIG. 15B). These findings indicate that the high chain packing density namely contributes to excellent non-fouling performance, as long as a sufficient thickness is obtained ($d_{wet}$=about 23 nm in this case).

The solvent effect was taken into consideration for investigating chain packing density and subsequent resistance to protein adsorption. Water and methanol were chosen as solvents for the super hydrophilic CB monomer due to their high polarity indices, which are 9.0 and 5.1, respectively. Higher methanol content leads to more controllable polymerization. These results for the first time reveal the correlation among non-fouling properties, growth rate and packing density of polymer films prepared via SI photo-polymerization approach, and point out the importance of the internal architecture of polymer brush for delicate design of desirable surface properties.

SPR Detection for TSH Hormone Antigen.

Functionalizable pCB was applied to a binding platform in SPR for in situ detection of TSH antigens in undiluted serum. Experiments were performed on pCB films fabricated from the solvents with MeOH:H$_2$O ratios of 50:50, 70:30 and 100:0 under 30 min UV radiation, and the wet thicknesses of resulting films were 93.7±1.5 nm, 67.8±1.2 nm, and 22.8±2.3 nm, respectively. For convenience, those samples were denoted pCB-94, pCB-68, and pCB-23, respectively, according to their wet thicknesses. The surfaces were functionalized with anti-TSH antibodies through EDC/NHS coupling chemistry and the resulting binding capacities were 422.7±8.2 ng cm$^{-2}$, 396.2±13.6 ng cm$^{-2}$, and 262.5±0.8 ng cm$^{-2}$ on pCB-94, pCB-68 and pCB-23, respectively. After the establishment of baseline, undiluted blood serum containing 1 μg mL-1 TSH antigens was flowed over the surfaces in contact with conjugated IgG molecules and, additionally, in the other channel the serum without antigen was parallel tested as a control experiment. In order to compare the net responses upon antigen binding on three surfaces, the signals obtained from TSH-containing channels were subtracted from the signals of control channels. The net sensor responses to TSH binding on pCB films indicated that the strengths of responses increased with decrease in film thicknesses.

The evanescent wave-based biosensor, such as SPR, exhibits a strength profile of a probing field exponentially decaying from the interface. For the regular SPR, the penetration depth of the probing field is typically around 200 nm, beyond which the binding event cannot be detected. pCB-23 with high chain packing density was prepared under a water-free condition. Compared to the films prepared from water-rich solutions, the pCB-23 represents very high sensor responses to TSH binding in complex media due to its ultra-low fouling properties and thin thickness although its antibody loading was the lowest. Therefore, the high resistance to non-specific adsorption and the effective use of probing field allow enhancing dramatically the specificity and sensitivity of biosensors.

While illustrative embodiments have been illustrated and described, it will be appreciated that various changes can be made therein without departing from the spirit and scope of the invention.

The embodiments of the invention in which an exclusive property or privilege is claimed are defined as follows:

1. A surface-anchored polymer assembly, comprising:
   (a) a nonfouling first layer having a first layer density, wherein the first layer is attached to a substrate and comprises a plurality of polycarboxybetaine polymers; and
   (b) a second layer having a second layer density, wherein the second layer comprises a plurality of polycarboxybetaine polymers each having carboxy groups and a plurality of recognition elements attached to the carboxy groups such that the recognition elements are attached throughout the entire second layer, and wherein the second layer is attached to the first layer, wherein the first layer density is greater than the second layer density.

2. The surface-anchored polymer assembly of claim 1, further comprising one or more additional layers attached to the second layer.

3. The surface-anchored polymer assembly of claim 1, wherein the first layer has a fibrinogen binding level less than about 30 ng/cm$^2$.

4. The surface-anchored polymer assembly of claim 1, wherein the first layer has a lysozyme binding level less than about 30 ng/cm$^2$.

5. The surface-anchored polymer assembly of claim 1, wherein the second layer is a crosslinked layer.

6. The surface-anchored polymer assembly of claim 1, wherein the first layer polymers are grafted from the substrate.

7. The surface-anchored polymer assembly of claim 1, wherein the first layer polymers are grafted to the substrate.

8. The surface-anchored polymer assembly of claim 1, wherein the second layer polymers are grafted from the first layer polymers.

9. The surface-anchored polymer assembly of claim 1, wherein the second layer polymers are grafted to the first layer polymers.

10. The surface-anchored polymer assembly of claim 1, wherein the polycarboxybetaine polymers have the formula:

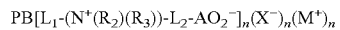

PB[L$_1$-(N$^+$(R$_2$)(R$_3$))-L$_2$-AO$_2^-$]$_n$(X$^-$)$_n$(M$^+$)$_n$ wherein
PB is the polymer backbone having n pendant zwitterionic groups;
R$_2$ and R$_3$ are independently selected from the group consisting of hydrogen, alkyl, and aryl, or taken together with the nitrogen to which they are attached form a cationic center;
L$_1$ is a linker that covalently couples the cationic center [N$^+$(R$_2$)(R$_3$)] to the polymer backbone;
L$_2$ is a linker that covalently couples the anionic center [A(=O)—O$^-$] to the cationic center;
A is C;
M$^+$ is an optional counter ion associated with the (A=O) O$^-$ anionic center;
X$^-$ is an optional counter ion associated with the cationic center; and
n is an integer from 1 to about 10,000.

11. The surface-anchored polymer assembly of claim 1, wherein the substrate is selected from metal and metal oxide surfaces, ceramic surfaces, synthetic and natural polymeric surfaces, glass surfaces, fiber glass surfaces, silicon/silica surfaces, carbon-based material surfaces, cell surfaces, or macromolecule surfaces (protein, DNAs, lipids).

12. The surface-anchored polymer assembly of claim 1, wherein the substrate is the surface of a diagnostic device, a medical device, a separation device, a targeting delivery carrier, a scaffold, or a marine coating.

13. The surface-anchored polymer assembly of claim 1, wherein the recognition element is selected from the group consisting of a peptide, a protein, a nucleic acid, and a small molecule.

14. The surface-anchored polymer assembly of claim 1, wherein the recognition element is selected from the group consisting of an antibody, an antibody fragment, a DNA, and an RNA.

15. A method for determining the presence of an analyte in a sample, comprising:
   (a) contacting a sample with a surface-anchored polymer assembly of claim 1, wherein the recognition element has a specific binding affinity for the analyte; and
   (b) interrogating the surface-anchored polymer assembly to determine whether the analyte has bound to the surface-anchored polymer assembly.

16. A hierarchical surface-anchored polymer assembly, comprising:
   a first layer comprising a plurality of first polycarboxybetaine polymers, wherein each first polycarboxybetaine polymer has a first end and a second end, wherein the first end of each first polycarboxybetaine polymer is attached to a surface;
   a second layer comprising a plurality of second polycarboxybetaine polymers, wherein each second polycarboxybetaine polymer has a first end and a second end, wherein the first end of each second polycarboxybetaine polymer is attached to the second end of a first polycarboxybetaine polymer, and wherein fewer than all of the plurality of first polycarboxybetaine polymers has a second polycarboxybetaine polymer attached to the second end; and a plurality of recognition elements attached to each of the plurality of second polycarboxybetaine polymers such that the recognition elements are attached throughout the entire second layer.

17. A hierarchical surface-anchored polymer assembly produced by a process comprising:

grafting a plurality of first polycarboxybetaine polymers from a surface to provide a plurality of first polymers having a first end attached to the surface and a second end distal from the surface;

capping less than all of the plurality of first polycarboxybetaine polymers at the second ends to prevent further polymerization from the second ends of a portion of the plurality of first polycarboxybetaine polymers, thereby providing a first polycarboxybetaine polymer layer with a first layer density;

grafting a plurality of second polycarboxybetaine polymers from the second end of less than all of the plurality of first polycarboxybetaine polymers grafted from the surface, thereby providing a second polycarboxybetaine polymer layer with a second layer density that is less than the first layer density; and attaching a plurality of recognition elements throughout the second polycarboxybetaine polymer layer.

* * * * *